(12) United States Patent
Duplantier et al.

(10) Patent No.: US 6,355,662 B1
(45) Date of Patent: Mar. 12, 2002

(54) NON-PEPTIDYL INHIBITORS OF A VLA-4 DEPENDENT CELL BINDING USEFUL IN TREATING INFLAMMATORY, AUTOIMMUNE, AND RESPIRATORY DISEASES

(75) Inventors: Allen Jacob Duplantier, Ledyard; Anthony John Milici, Branford; Louis Stanley Chupak, Old Saybrook, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/403,846

(22) PCT Filed: May 31, 1999

(86) PCT No.: PCT/IB99/00973

§ 371 Date: Oct. 26, 1999

§ 102(e) Date: Oct. 26, 1999

(87) PCT Pub. No.: WO00/00477

PCT Pub. Date: Jan. 6, 2000

Related U.S. Application Data

(62) Division of application No. 09/338,832, filed on Jun. 23, 1999
(60) Provisional application No. 60/091,180, filed on Jun. 30, 1998, now abandoned.

(51) Int. Cl.[7] .................... A61K 31/42; A61K 31/17; C07D 263/30
(52) U.S. Cl. .................... 514/374; 514/596; 514/597; 548/235
(58) Field of Search .................... 514/374, 396, 514/397; 548/235, 236

(56) References Cited

FOREIGN PATENT DOCUMENTS

| EP | 529858 | * | 3/1993 |
| WO | 9622966 | * | 3/1993 |

* cited by examiner

Primary Examiner—Richard L. Raymond
Assistant Examiner—Sudhaker B Patel
(74) Attorney, Agent, or Firm—Peter C. Richardson; Paul H. Ginsburg; Raymond M. Speer

(57) ABSTRACT

Compounds of Formula (1.0.0):

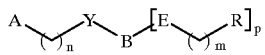

(1.0.0)

are described wherein A is for example aryl, heteroaryl or heterocyclyl, Y is preferably —C(=O)—; B is independently selected from a group of moieties, the most preferred of which are those of partial Formulas (1.1.2) and (1.1.6):

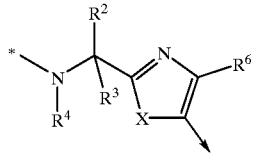

(1.1.2)

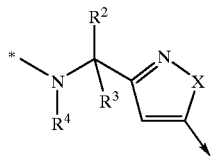

(1.1.6)

and E is a single bond; oxygen; 1,1-cyclopropyl; $C(CH_3)_2$; $CF_2$; or a bridging moiety of partial Formula (1.9.0):

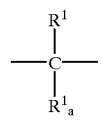

where $R^1_a$ is hydrogen when $R^1$ has the meaning of a mono-valent substituent; and $R^1_a$ is a single bond when $R^1$ has the meaning of a di-valent substituent. Said compounds are useful in methods of treating or preventing an inflammatory, autoimmune or respiratory diseases by inhibiting cell adhesion and consequent or associated pathogenic processes subsequently mediated by VLA-4.

14 Claims, No Drawings

NON-PEPTIDYL INHIBITORS OF A VLA-4 DEPENDENT CELL BINDING USEFUL IN TREATING INFLAMMATORY, AUTOIMMUNE, AND RESPIRATORY DISEASES

REFERENCE TO RELATED APPLICATIONS

This application is a divisional of U.S. Ser. No. 09/338,832 filed Jun. 23, 1999, now U. S. Pat. No. 6,306,887, issued Oct. 23, 2001; which is a continuation of provisional application U.S. Ser. No. 60/091,180 filed Jun. 30, 1998, now abandoned, benefit of which is hereby claimed; and which is a submission pursuant to 35 U.S.C. §371 under International Application No. PCT/IB99/00973 filed May 31, 1999, published as WO 00/00477 on Jan. 6, 2000.

The present invention relates to compounds which are non-peptidyl in structure and active as potent inhibitors of the binding of very late antigen-4 (VLA-4; $\alpha_4\beta_1$; CD49d/CD29) to proteins such as vascular cell adhesion molecule-1 (VCAM-1), the HepII/IIICS domain (CS-1 region) of fibronectin and osteopontin. As such they are useful in the inhibition of cell adhesion and consequent or associated pathogenic processes subsequently mediated by VLA-4. The compounds and pharmaceutical compositions of this invention may be used in the treatment of many inflammatory, autoimmune and respiratory diseases, especially asthma.

BACKGROUND OF THE INVENTION

One of the most fundamental processes necessary for normal host defence is the regulated trafficking of leukocytes out of the vasculature. This system is designed to allow normal recirculation of leukocytes, yet because it enables the rapid extravasation of leukocytes at sites of injury it is one of the central pathogenic mechanisms of inflammatory, respiratory and autoimmune diseases in mammals. Cell adhesion is a key factor in this process, and it is particularly relevant to the present invention regarding the cell/cell and cell/matrix binding of hematopoietic cells containing VLA-4.

VLA-4 is a member of a superfamily of cell surface macromolecular receptors called integrins, which are non-covalent heterodimeric complexes consisting of an $\alpha$ subunit and a $\beta$ subunit (Hemler, Ann. Rev. Immunol., 8, p.365, 1990). Eighteen different $\alpha$ subunits have been identified and labeled $\alpha_1$–$\alpha_{10}$, $\alpha_L$, $\alpha_M$, $\alpha_X$, $\alpha_D$, $\alpha_{LRI}$, $\alpha_{IIB}$, $\alpha_V$ and $\alpha_E$; while nine different $\beta$ subunits have been identified and labeled $\beta_1$–$\beta_9$. Each integrin molecule can be categorized into a subfamily based on the type of its $\alpha$ and $\beta$ subunits.

The $\alpha_4\beta_1$ integrin, VLA-4, is an integrin constitutively expressed by all leukocytes (e.g., monocytes, lymphocytes, basophils, eosinophils, mast cells and macrophages) except polymorphonuclear leukocytes. The binding of this integrin to one of its ligands has a number of known cell adhesion and activation functions (Hemler, Ann. Rev. Immunol., 8, p.365, 1990; Walsh et al., Clin. and Exp. Allergy, 25, p. 1128, 1995; Huhtala et al., J. Cell Biol., 129, p. 867, 1995). In particular, it is a receptor for the cytokine-inducible endothelial cell surface protein known as vascular cell adhesion molecule-1 (VCAM-1), and for the alternatively spliced forms of the extracellular matrix protein fibronectin (FN) containing the CS-1 domain (Ruegg et al., J. Cell Biol., 177, p. 179, 1991; Wayner et al., J. Cell Biol., 105, p. 1873, 1987; Kramer et al., J. Biol. Chem., 264, p.4684, 1989; Gehisen et al., Science, 24, p. 1228, 1988). The importance of VLA-4 cell adhesion interactions has been established by the use of specific monoclonal antibody (mAb) antagonists of the $\alpha$ subunit of VLA-4, which have demonstrated that inhibitors of VLA-4 dependent cell adhesion prevent or inhibit numerous inflammatory, respiratory and autoimmune pathological conditions (Chisholm et al., Eur. J. Immunol., 23, p. 682, 1993; Lobb et al., J. Clin. Invest., 94, p. 1722, 1994; Richards et al., Am. J. Respir. Cell Mol. Biol., 15, p.172, 1996; Soiluhanninen et al., J. Neuroimmunol., 72, p. 95, 1997; Sagara et al., Int. Arch. Allergy Immunol., 112, p.287, 1997; Fryer et al., J. Clin. Invest., 99, p. 2036, 1997). In addition, confirmation that this pathological processes can be inhibited with agents other than antibodies has been observed in animal models following treatment with a synthetic CS-1 peptide or a small molecule peptide inhibitor of VLA-4 (Ferguson et al., Proc. Natl. Acad. Sci., 88, p.8072, 1991; Wahl et al., J. Clin. Invest., 94, p.655, 1994; Molossi et al., J. Clin. Invest., 95, p.2601, 1995; Abraham et al., Am. J. Respir. Crit. Care Med., 156, p. 696, 1997; Jackson et al., J. Med. Chem., 40, p. 3359, 1997).

DESCRIPTION OF THE STATE OF THE ART

The investigation of mAb and peptide VLA-4 antagonists in the art has already been noted above. In defining the binding site for $\alpha_4\beta_1$ it was observed that lymphoid cells can bind to two different sites on fibronectin (Bernardi et al., J. Cell Biol., 105, p. 489, 1987). One component of this cell binding activity has previously been identified as the tripeptide Arg-Gly-Asp (RGD) that binds to the integrin $\alpha_5\beta_1$ (VLA5). Subsequently, the minimum amino acid sequence required to bind and antagonize the activity of VLA-4 on leukocytes to the alternatively spliced site in fibronectin was determined (Humphries et al., J. Biol. Chem., 266, p.6886, 1987; Garcia-Pardo et al., J. Immunol., 144, p.3361, 1990; Komoriya et al., J. Biol. Chem., 266, p. 15075, 1991). It was discovered that the VLA-4 binding domain in the CS-1 region of fibronectin (FN) comprised the octapeptide: Glu-Ile-Leu-Asp-Val-Pro-Ser-Thr, as well as two overlapping pentapeptides: Glu-Ile-Leu-Asp-Val and Leu-Asp-Val-Pro-Ser. All of these peptides inhibited FN-dependent cell adhesion, leading to the early conclusion that the minimal amino acid sequence required for inhibition was Leu-Asp-Val (LDV). In fact the LDV minimal inhibitory sequence was observed to be equally effective as the full length CS-1 fragment in binding the activated form of VLA-4 (Wayner et al., J. Cell Biol., 116, p. 489, 1992).

Various integrins are believed to bind to extracellular matrix proteins at an Arg-Gly Asp (RGD) recognition site. RGD based cyclic peptides have been made that are said to be able to inhibit both $\alpha_4\beta_1$ and $\alpha_5\beta_1$ binding to FN (Nowlin et al., J. Biol. Chem., 268, p. 20352, 1993; PCT/US91/04862) even though the primary recognition on FN for $\alpha_4\beta_1$ is LDV. The cyclic peptide is:

where TPro denotes 4-thioproline.

Other peptidyl inhibitors of VLA-4 are those referred to in Arrhenius, T. S.; Elices, M. J.; Gaeta; F. C. A.; "CS-1 Peptidomimetics", WO 95/15973, wherein a representative compound of the type referred to is the following:

wherein NCy[3] is selected from, inter alia, morpholinamido, thiomorpholinamido, 4-(thiadioxo)piperidinamido, and D-2-(carboxamide)-pyrrolidinamido, piperidinamido, and substituted piperidinamido.

The Leu-Asp-Val tripeptide has been used as the core of a group of inhibitors of VLA-4 dependent cell adhesion of the formula:

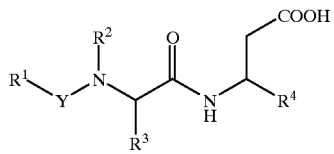

where R¹ may be 4-(N'-(2-methylphenyl)urea)phenylmethyl; Y may be C=O; R² may be H; R³ may be iso-butyl; and R¹⁴ may be 1,3-benzodioxol-5-yl. See Adams, S. P.; Lin, K.-C.; Lee, W.-C.; Castro, A. C.; Zimmerman, C. N.; Hammond, C. E.; Liao, Y.-S.; Cuervo, J. H.; Singh, J.; "Cell Adhesion Inhibitors", WO 96/22966, which refers to compounds such as the following:

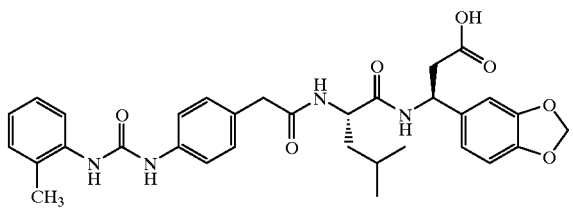

Other peptidyl inhibitors of VLA-4-mediated cell adhesion which have been reported include those of the formula:

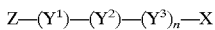

where Z may be 4-(N'-(2-methylphenyl)urea)phenylacetyl; (Y¹)—(Y²)—(Y³)ₙ represents a series of amino acids forming a peptide chain; and X may be OH. See Lin, K.-C.; Adams, S. P.; Castro, A. C.; Zimmerman, C. N.; Cuervo, J. H.; Lee, W.-C.; Hammond, C. E.; Carter, M. B.; Almquist, R. G.; Ensinger, C. L.; "Cell Adhesion Inhibitors", WO 97/03094, which refers to compounds such as the following:

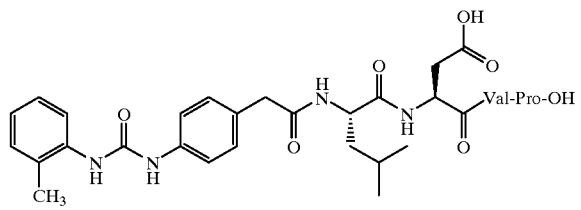

See further Zheng, Z.; Ensinger, C. L.; Adams, S. P.; WO 98/04247 which refers to cell adhesion inhibitors comprising a compound of the formula: A–B, where A comprises a specificity determinant which does not impart significant IIb/IIIa activity, and B comprises an integrin scaffold. The following compound is representative of those referred to:

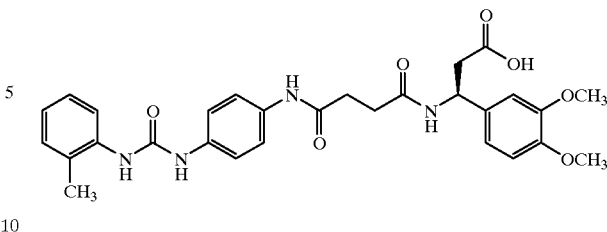

See also Singh, J.; Zheng, Z.; Sprague, P.; Van Vlijmen, H. W. T.; Castro, A.; Adams, S. P.; "Molecular Model for VLA-4 Inhibitors", WO 98/04913, which refers to a three dimensional pharmacophore model of a compound having VLA-4 inhibitory activity, comprising features defined by a table of tolerances and three dimensional coordinates x, y, and z. The following compound is representative of those referred to:

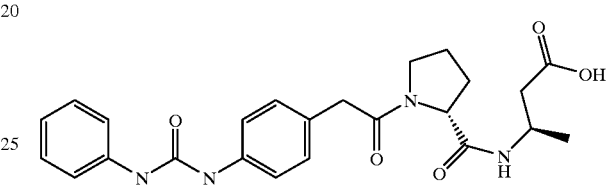

Despite the above-described advances in the art with regard to inhibitors of VLA-4 mediated cell adhesion, the artisan will quickly recognize that these peptidyl inhibitors are prone to poor absorption, poor solubility and are subject to metabolism in vivo (both systemically and locally when administered directly into the lung) diminishing their opportunity to appreciably affect the course of an inflammatory, respiratory or autoimmune disease. Accordingly, there still exists in the art a need for non-peptidyl or semi-peptidyl therapeutic agents which can effectively treat or prevent such pathological conditions.

SUMMARY OF THE INVENTION

The present invention is concerned with compositions which inhibit VLA-4 dependent cell adhesion in a mammal. The present invention thus relates to a compound of Formula (1.0.0):

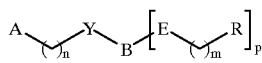

(1.0.0)

and pharmaceutically acceptable salts and other prodrug derivatives thereof, wherein:

A is aryl, heteroaryl, or heterocyclyl as defined herein; where said aryl, heteroaryl, or heterocyclyl is substituted with 0 to 3 R¹⁰; or is a member selected from the group consisting of divalent radicals: —A¹—NHC(=O)NH—A²—, —A¹—NHC(=O)O—A²—, and —A¹—NH(NCN)NH—A²—, where A¹ and A² is each independently selected from the group consisting of hydrogen, aryl, heteroaryl, and heterocyclyl as defined herein, where said aryl, heteroaryl, or heterocyclyl is substituted with 0 to 3 R¹⁰ ;

B is a member independently selected from the group consisting of the following:

(1.1.0) 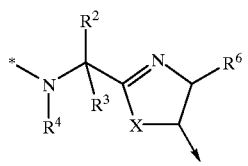

(1.1.1) 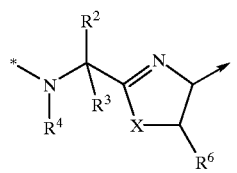

(1.1.2) 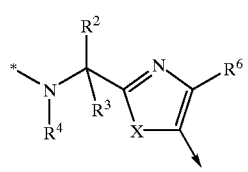

(1.1.3) 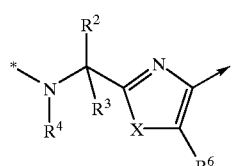

(1.1.4) 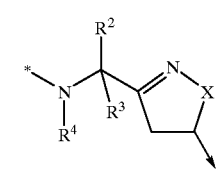

(1.1.5) 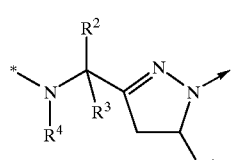

(1.1.6) 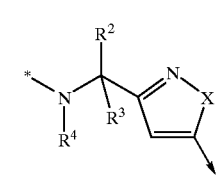

(1.1.7) 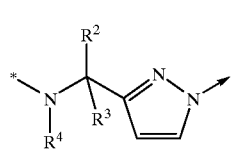

(1.1.8) 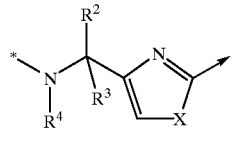

(1.1.9) 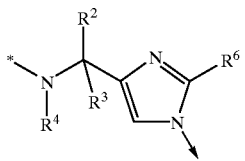

(1.1.10) 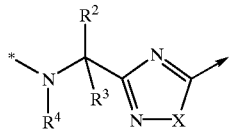

(1.1.11) 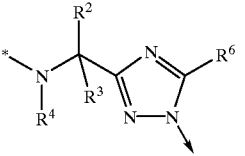

(1.1.12) 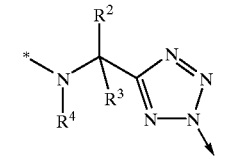

(1.1.13) 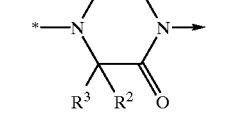

(1.1.14) 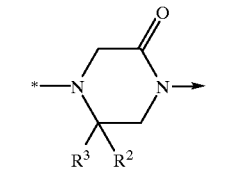

where the symbol "*" indicates the point of attachment of the moiety represented by each partial Formula (1.1.0) through (1.1.14) to the moiety "Y" in Formula (1.0.0); and the symbol "→" indicates the point of attachment of the moiety represented by each partial Formula (1.1.0) through (1.1.14) to the moiety "E" in Formula (1.0.0);

E is a single bond; —O—; —CH=CH—; or a moiety of Formula (1.9.0):

(1.9.0) 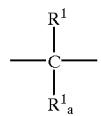

where $R^1_a$ is hydrogen when $R^1$ has the meaning of a mono-valent substituent; and $R^1_a$ is a single bond when $R^1$ has the meaning of a di-valent substituent;

X is —O—; —S(=O)$_q$—; or —N(R$^{14}$)—;

Y is —C(=O)—; —C(=S)—; —S(=O)$_2$—; or —CH(R$^a$)—;

m is an integer independently selected from 0, 1 and 2;

n is an integer independently selected from 1 and 2;

p is an integer independently selected from 1 and 2, provided that p must be selected as 1 where B is selected as partial Formula (1.1.2), (1.1.3), (1.1.5); (1.1.6), (1.1.7), (1.1.8), (1.1.9), (1.1.10), (1.1.11), (1.1.12), (1.1.13) or (1.1.14);

q is an integer independently selected from 0 and 2;

R is independently selected from the group consisting of -tetrazolyl; —C(=O)—OR$^5$; —C(=O)(CH$_2$)$_k$C(=O) OR$^5$; —C(=O)NO•; —C(=O)—NH—S(=O)$_2$R$^5$; —S(=O)$_2$—NR$^{14}$R$^5$; —C(=O)NHS(=O)$_2$R$^6$; and a moiety of partial Formula (3.0.0):

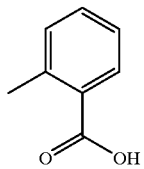

(3.0.0)

where:

k is an integer independently selected from 0, 1 and 2;

R$^1$ is independently selected from the group consisting of hydrogen; =O; =S; F; (C$_1$–C$_6$) alkyl substituted with 0 to 3 R$^{10}$; (C$_2$–C$_6$) alkenyl substituted with 0 to 3 R$^{10}$; (C$_2$–C$_6$) alkynyl substituted with 0 to 3 R$^{10}$; a (C$_3$–C$_{14}$) carbocyclic ring system substituted with 0 to 3 R$^{12}$; aryl substituted with 0 to 3 R$^{12}$; and aryl(C$_1$–C$_4$) alkyl wherein said aryl and alkyl are substituted with 0 to 3 R$^{12}$; heterocyclyl as defined herein, substituted with 0 to 3 R$^{12}$; and heterocyclyl(C$_1$–C$_4$) alkyl as defined herein, wherein said heterocyclyl and alkyl are substituted with 0 to 3 R$^{12}$; C(=O)NR$^8$R$^9$; and C(=O)R$^8$;

R$^2$ and R$^3$ are each independently selected from the group consisting of hydrogen; (C$_1$–C$_4$) alkyl substituted with 0 to 3 R$^{13}$; (C$_2$–C$_6$) alkenyl substituted with 0 to 3 R$^{13}$; a (C$_3$–C$_{14}$) carbocyclic ring system substituted with 0 to 3 R$^{13}$; (C$_1$–C$_4$) alkoxycarbonylamino-(C$_1$–C$_4$) alkyl-; (C$_1$–C$_4$) alkylthio-(C$_1$–C$_4$)alkyl-; (C$_1$–C$_4$) alkylsulfonyl-(C$_1$–C$_4$)alkyl-; hydroxy(C$_1$–C$_4$) alkylthio-(C$_1$–C$_4$)alkyl-; (C$_1$–C$_4$) alkylcarbonylamino-(C$_1$–C$_4$)alkyl-; (C$_1$–C$_4$) alkylsulfonylamino-(C$_1$–C$_4$) alkyl-; (C$_1$–C$_4$) alkylsulfonylaminocarbonyl-(C$_1$–C$_4$) alkyl-; and a heterocyclyl ring as defined herein, substituted with 0 to 3 R$^{13}$; provided that R$^2$ and R$^3$ are each defined as above; or they are taken together as defined below; or one of them is taken together with R$^4$ as defined below, in which case the other has the meaning of hydrogen or methyl;

R$^2$ and R$^3$ are taken together to form a spirocyclic (C$_3$–C$_{14}$) carbocyclic ring substituted With 0 to 3 R$^{13}$; or R$^2$ or R$^3$ is taken together with R$^4$ and the carbon and nitrogen atoms to which they are respectively attached to form a heteroaryl or heterocyclyl group as defined herein, substituted with 0 to 3 R$^{12}$;

R$^5$ is hydrogen; (C$_1$–C$_4$) alkyl; (C$_3$–C$_6$) cycloalkyl; or aryl;

R$^6$ is hydrogen; (C$_1$–C$_4$) alkyl; (CH$_2$)$_r$—(C$_3$–C$_6$) cycloalkyl; or (CH$_2$)$_s$-aryl; where:

r and s are each independently an integer selected from 0, 1, and 2;

R$^8$ and R$^9$ are each independently selected from the group consisting of hydrogen; (C$_1$–C$_4$) alkyl substituted with 0 to 3 R$^{10}$; a (C$_3$–C$_{14}$) carbocyclic ring system substituted with 0 to 3 R$^{12}$; aryl substituted with 0 to 3 R$^{12}$; and aryl-(C$_1$–C$_4$) alkyl wherein said aryl and alkyl are substituted with 0 to 3 R$^{12}$; heterocyclyl as defined herein substituted with 0 to 3 R$^{12}$; and heterocyclyl-(C$_1$–C$_4$) alkyl as defined herein, wherein said heterocyclyl and alkyl are substituted with 0 to 3 R$^{12}$;

R$^{10}$ is independently selected from the group consisting of F; Cl; —C(=O)OR$^{14}$; —OH; nitro; cyano; amino; di(C$_1$–C$_4$) alkylamino; (C$_1$–C$_4$) alkyl; (C$_1$–C$_4$) alkoxy; (C$_1$–C$_4$) alkylthio; phenoxy; trifluoromethoxy; (C$_3$–C$_6$) cycloalkyl; (C$_3$–C$_6$) cycloalkoxy; (C$_3$–C$_6$) cycloalkoxycarbonyl; (C$_1$–C$_4$) alkylcarbonylamino; (C$_1$–C$_4$) alkylsulfonylamino; (C$_1$–C$_4$) alkylurea; and (C$_1$–C$_4$) alkyl and (C$_1$–C$_4$) alkoxy each substituted with 1 to 3 substituents independently selected from F and Cl;

R$^{12}$ when a substituent on a carbon atom, is independently selected from the group consisting of F; Cl; (C$_1$–C$_4$) alkyl; (C$_3$–C$_6$) cycloalkyl; (C$_1$–C$_4$) alkoxy; —C(=O) OR$^{14}$; —OH; (C$_1$–C$_4$) alkyl and (C$_1$–C$_4$) alkoxy each substituted with 1 to 3 substituents independently selected from F and Cl; (C$_1$–C$_4$) alkoxycarbonyl; (C$_1$–C$_4$) alkylcarbonyl; (C$_1$–C$_4$) alkylcarbonyloxy; and a heteroaryl or heterocyclyl group as defined herein which is 5- or 6-membered; or R$^{12}$ when two R$^{12}$ groups are attached to adjacent carbons of a carbocyclic, aryl, heteroaryl, or heterocyclic ring, may be a 3- or 4-carbon chain which forms a fused 5- or 6-membered ring, said 5- or 6-membered ring being optionally mono- or di-substituted on the aliphatic carbon atoms thereof with F, Cl, (C$_1$–C$_4$) alkyl, (C$_1$–C$_4$) alkoxy, or hydroxy; or R$^{12}$ when R$^{12}$ is attached to a saturated carbon atom, may be =O or =S; or when R$^{12}$ is attached to a sulfur atom, may be =O;

R$^{12}$ when a substituent on a nitrogen atom, is independently selected from the group consisting of hydroxy; hydroxy(C$_1$–C$_4$) alkyl; (C$_1$–C$_4$) alkoxy; (C$_3$–C$_6$) cycloalkyl; (C$_1$–C$_4$) alkylcarbonyl; and aryl;

R$^{13}$ is independently selected from the group consisting of aryl; heteroaryl; heterocyclyl; (C$_1$–C$_4$) alkoxy; (C$_3$–C$_6$) cycloalkyl; (C$_2$–C$_6$) alkynyl; —OR$^{14}$; heterocyclylcarbonyl; (C$_1$–C$_4$) alkylthio; —NR$^6$R$^5$; and —C(=O) NR$^{14}$R$^5$; and R$^{14}$ is hydrogen; hydroxy; (C$_1$–C$_4$) alkyl; (C$_3$–C$_6$) cycloalkyl; or aryl The present invention is also concerned with pharmaceutical compositions comprising one or more of the compounds of the present invention as described above together with a pharmaceutically acceptable carrier for said compound(s), wherein the amount of said compound(s) present is effective for preventing, inhibiting, suppressing or reducing cell adhesion and consequent or associated pathogenic processes subsequently mediated by VLA-4. The present invention is further concerned with pharmaceutical compositions which in addition to containing a compound of the present invention, additionally comprise one or more therapeutic agents selected from the group consisting essentially of anti-inflammatory corticosteroids, nonsteroidal anti-inflammatory agents, bronchodilators, anti-asthmatic agents, and immunosuppressant agents.

The present invention is still further concerned with a method of treating or preventing an inflammatory, autoimmune or respiratory diseases by inhibiting cell adhesion and consequent or associated pathogenic processes subsequently mediated by VLA-4, comprising administering to a mammal in need of such treatment a therapeutically effective amount of a pharmaceutical composition of the present invention. The pharmaceutical compositions of the present invention may be used in the treatment of many inflammatory, autoimmune and respiratory diseases, including but not limited to asthma, multiple sclerosis, rheumatoid arthritis, osteoarthritis, inflammatory bowel disease, psoriasis, host rejection following organ transplantation, atherosclerosis, and other diseases mediated by or associated with VLA-4.

DETAILED DESCRIPTION OF THE INVENTION

The present invention relates to compounds which inhibit cell adhesion and subsequent pathogenic processes mediated by VLA-4. These compounds, which are thus useful in the treatment of many inflammatory, autoimmune amd respiratory diseases, may be illustrated by Formula (1.0.0):

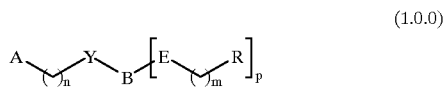

(1.0.0)

For compounds of Formula (1.0.0), the terminal group identified as A has the meaning aryl, heteroaryl, or heterocyclyl substituted with 0 to 3 $R^{10}$, or is a member selected from the group consisting of divalent radicals: —$A^1$—NHC(=O)NH—$A^2$—, —$A^1$—NHC(=O)O—$A^2$—, and —$A^1$—NH(NCN)NH—$A^2$—, where $A^1$ and $A^2$ is each independently selected from the group consisting of hydrogen, aryl, heteroaryl, and heterocyclyl, where said aryl, heteroaryl, or heterocyclyl is substituted with 0 to 3 $R^{10}$.

The term "aryl" as used with reference to "A", as well as in other contexts throughout the instant specification, is intended to refer to a carbocyclic aromatic group which is a member selected from the group consisting essentially of phenyl, naphthyl, indenyl, indanyl, and fluorenyl. It is preferred, however, that where "A" is "aryl", that it is phenyl.

The term "heteroaryl" as used with reference to "A", as well as in other contexts throughout the instant specification, is intended to refer to a heterocyclic aromatic group which is a member selected from the group consisting essentially of furyl, thienyl, pyrrolyl, oxazolyl, isoxazolyl, thiazolyl, isothiazolyl, imidazolyl, imidazolinyl, pyrazolyl, pyrazolinyl, oxadiazolyl, thiadiazolyl, triazolyl, pyridyl, pyrazinyl, pyridazinyl, pyrimidinyl, triazinyl, pyranyl, parathiazinyl, indolyl, isoindolyl, 3H-indolyl, indolinyl, benzo[b]furanyl, 2,3-dihydrobenzofuranyl, benzo[b] thiophenyl, 1H-indazolyl, benzimidazolyl, benzthiazolyl, purinyl, quinolinyl, isoquinolinyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, and pyrazolo[1,5-c]triazinyl.

It is preferred, however, that where "A" is "heteroaryl" that it is furyl, thienyl, pyrrolyl, oxazolyl, isoxazolyl, thiazolyl, imidazolyl, pyridyl, pyrimidinyl, indolyl, benzo [b]furanyl, benzimidazolyl, or quinolinyl. More preferably, "A" is pyridyl.

The terms "heterocylic" and "heterocyclyl" as used with reference to "A", as well as in other contexts throughout the instant specification, are both intended to refer to a non-aromatic 3- to 10-membered carbocyclic ring in which at least one of the carbon atoms of the ring has been replaced by a heteroatom selected from N, O or S. Preferably two, and more preferably one heteroatom is present, except that in the case of nitrogen, as many as four N heteroatoms may be present. The heterocyclyl group may comprise one or two fused rings, and further may include an aryl-fused ring. In a prefered meaning, "heterocyclyl" refers to a member selected from the group consisting essentially of oxiranyl, pyrrolidinyl, pyrazolidinyl, imidazolidinyl, tetrazolidinyl, piperidinyl, piperazinyl, morpholinyl, thiomorpholinyl, and benzodioxolane, especially 1,3-benzodioxol-5-yl.

It is preferred, however, that where "A" is "heterocyclyl" that it is pyrrolidinyl, piperidinyl, piperazinyl, or morpholinyl.

Where "A" is defined as a moiety selected from the above-defined aryl, heteroaryl, or heterocyclyl groups, said moiety may be substituted with 0 to 3 $R^{10}$. The choice of "0" merely denotes that there are no substituents, substitution being optional. Where substitution occurs, preferably there are two substituents, and more preferably there is only one substituent.

Where a substituent $R^{10}$ is used, it will be independently selected from the group consisting essentially of F; Cl; —C(=O)$OR^{14}$; —OH; nitro; cyano; amino; di($C_1$–$C_4$) alkylamino; ($C_1$–$C_4$) alkyl; ($C_1$–$C_4$) alkoxy; ($C_3$–$C_6$) cycloalkyl; ($C_3$–$C_6$)cycloalkoxy; ($C_1$–$C_4$) alkylthio; phenoxy; trifluoromethoxy; ($C_3$–$C_6$) cycloalkoxycarbonyl; ($C_1$–$C_4$) alkylcarbonylamino; ($C_1$–$C_4$) alkylsulfonylamino; ($C_1$–$C_4$) alkylurea; and ($C_1$–$C_4$)alkyl and ($C_1$–$C_4$)alkoxy each substituted with 1 to 3 substituents independently selected from F and Cl; where $R^{14}$ is as further defined herein. Preferably, however, there is a single substituent and it is F, Cl, OH, methyl, methoxy, cyclohexyl, cyclopropyloxy, or $F_3C$—.

The term "alkyl" as used with reference to the substituents "$R^{10}$" on the group "A", as well as in other contexts throughout the instant specification, and whether used alone or in combination, refers to a straight-chain or branched chain alkyl radical containing the indicated number of carbon atoms, usually from 1 to 6 but often from 1 to 4, carbon atoms. Examples of such radicals include, but are not limited to, methyl, ethyl, n-propyl, iso-propyl, n-butyl, iso-butyl, sec-butyl, tert-butyl, pentyl, iso-amyl, and hexyl.

The term "alkoxy" as used with reference to the substituents "$R^{10}$" on the group "A", as well as in other contexts throughout the instant specification, and whether used alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, and tert-butoxy.

The term "cycloalkyl" as used with reference to the substituents "$R^{10}$" on the group "A", as well as in other contexts throughout the instant specification, and whether used alone or in combination, refers to a cyclic alkyl radical containing from 3 to 6 carbon atoms. Examples of such cycloalkyl radicals include, but are not limited to, cyclopropyl, cyclobutyl, cyclopentyl, and cyclohexyl.

The term "cycloalkyloxy" as used with reference to the substituents "$R^{10}$" on the group "A", as well as in other contexts throughout the instant specification, and whether used alone or in combination, refers to a cycloalkyl ether radical wherein the term "cycloalkyl" is as defined above. Examples of such cycloalkyloxy radicals include, but are not limited to, cyclopropyloxy, cyclobutyloxy, cyclopentyloxy, and cyclohexyloxy.

A preferred meaning of "A" is that of a ureido radical, more preferably a divalent radical which is a member selected from the group consisting of —A$^1$—NHC(=O)NH—A$^2$—, —A$^1$—NHC(=O)O—A$^2$—, and —A$^1$—NH(NCN)NH—A$^2$—, where A$^1$ and A$^2$ is each independently selected from the group consisting of hydrogen, aryl, heteroaryl, and heterocyclyl, where said aryl, heteroaryl, or heterocyclyl is substituted with 0 to 3 R$^{10}$. The aryl, heteroaryl or heterocyclyl group which is bonded to one or both sides of the ureido radical is selected in accordance with the definitions set out above, as are the 0 to 3 substituents R$^{10}$. It is preferred that an aryl group be covalently bonded to the both sides of the ureido radical, and it is further preferred that this aryl group be phenyl. It is most preferred that said phenyl group have a single substituent which is preferably F, Cl, methyl, methoxy, or F$_3$C—. Examples of the preferred meanings of "A" are shown in partial Formulas (4.0.0) though (4.0.11):

(4.0.0)

(4.0.1)

(4.0.2)

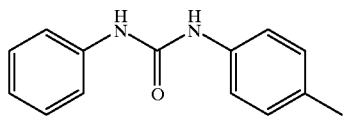

(4.0.3)

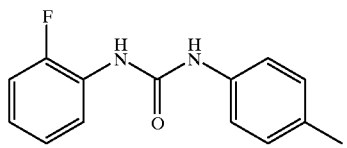

(4.0.4)

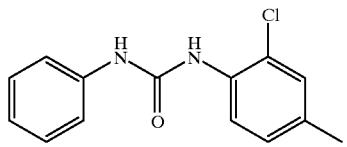

(4.0.5)

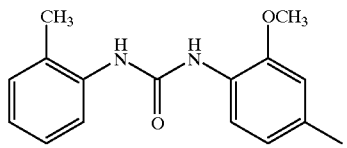

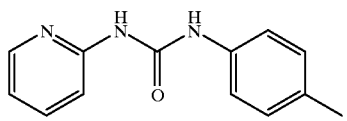

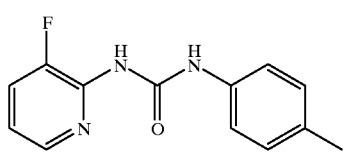

(4.0.6)

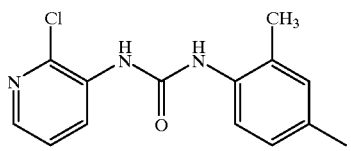

(4.0.7)

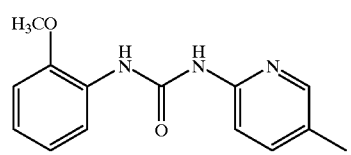

(4.0.8)

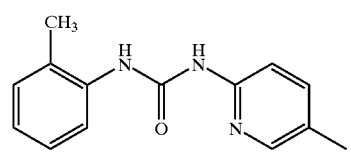

(4.0.9)

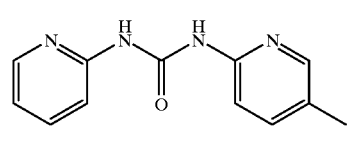

(4.0.10)

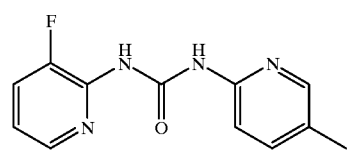

(4.0.11)

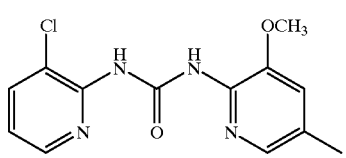

The component of the compounds of Formula (1.0.0) which is immediately adjacent to the "A" component, is the methylene or ethylene bridging element where n=1 or 2, respectively. It is preferred that n=1 and that there be a methylene bridge. Accordingly, within the context of the above-stated preferences for the meaning of the "A" component, and adding the methylene bridge, the following most preferred termini which include the component "A", may be represented by the following partial Formulas (4.1.0) through (4.1.23):

| | | |
|---|---|---|
| 4-hydroxyphenyl- |  | (4.1.0) |
| 3-methoxy-4-(N'-phenylurea)-phenylmethyl- | 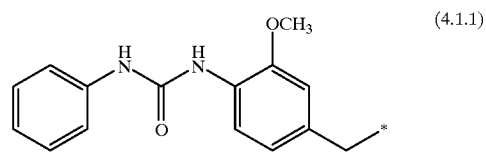 | (4.1.1) |
| 4-(n'-phenylurea)-phenylmethyl- | 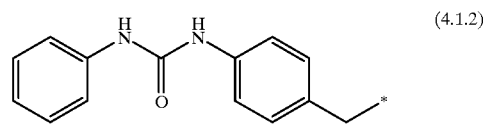 | (4.1.2) |
| 4-[N'-(2-methylphenyl)-urea]-phenylmethyl- | 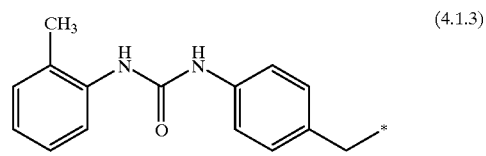 | (4.1.3) |
| 4-[N'-(2-methoxyphenyl)-urea]-phenylmethyl- | 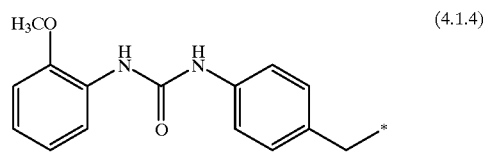 | (4.1.4) |
| 3-methoxy-4-[N'-(2-methylphenyl)-urea]-phenylmethyl- | 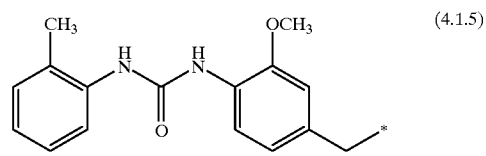 | (4.1.5) |
| 4-[N'-(2-pyridyl)-urea]-phenylmethyl- | 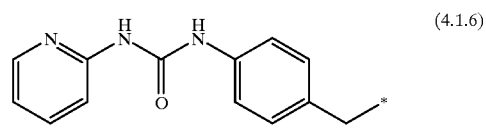 | (4.1.6) |
| 6-methoxy-5-[N'-(2-methylphenyl)-urea]-2-pyridylmethyl- | 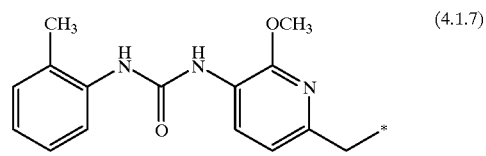 | (4.1.7) |
| 4-[N'-(3-methyl-2-pyridyl)-urea]-phenylmethyl- | 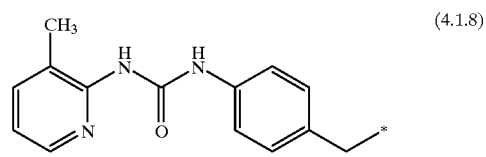 | (4.1.8) |
| 3-methoxy-4-[N'-(3-methyl-2-pyridyl)-urea]-phenylmethyl- | 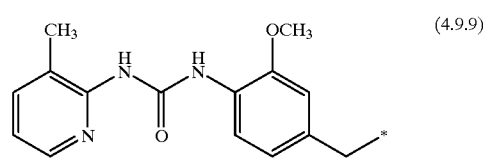 | (4.9.9) |

| | | |
|---|---|---|
| 3-methoxy-4-[N'-(2-pyridyl)-urea]-phenylmethyl- | 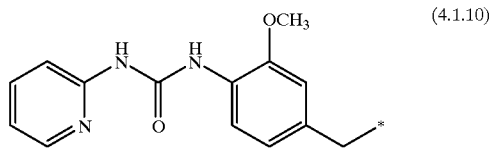 | (4.1.10) |
| 4-[N'-(2-pyridyl)-urea]-phenylmethyl- | 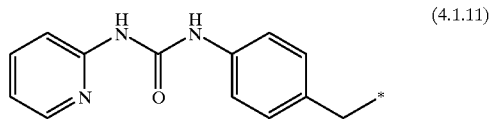 | (4.1.11) |
| 4-[N'-(2-fluorophenyl)-urea]-phenylmethyl- | 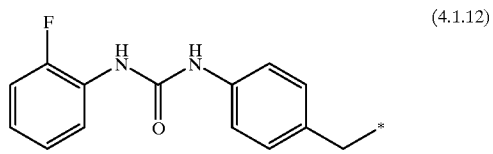 | (4.1.12) |
| 4-[N'-(2-chlorophenyl)-urea]-phenylmethyl- | 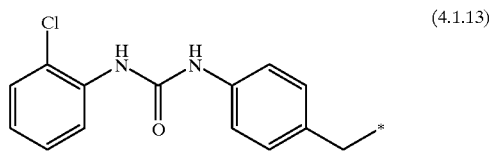 | (4.1.13) |
| 4-[N'-(2-chlorophenyl)-urea]-3-methoxyphenylmethyl- | 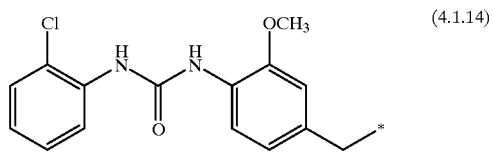 | (4.1.14) |
| 4-[N'-(4-iso-propylphenyl)-urea]-phenylmethyl- | 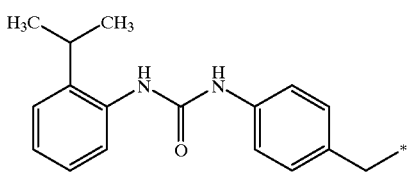 | (4.1.15) |
| 6-methoxy-5-[N'-(o-toluyl)-urea]-2-pyridylmethyl- | 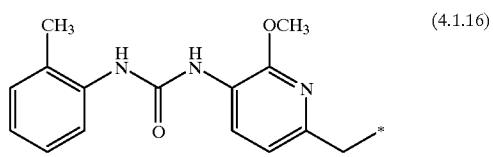 | (4.1.16) |
| 4-[N'-(3-cyclopentyl-2-pyridyl)-urea]-phenylmethyl- | 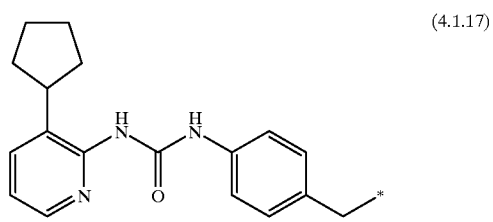 | (4.1.17) |
| 4-[N'-(2-cyclopentyl)-urea]-phenylmethyl- | 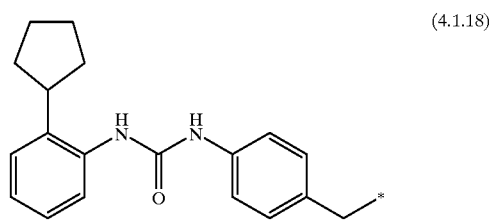 | (4.1.18) |

-continued

| | | |
|---|---|---|
| 4-[N'-(3-cyclopropyloxy-2-pyridyl)-urea]-phenylmethyl- | 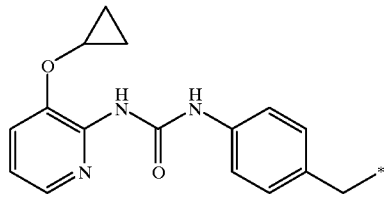 | (4.1.19) |
| 4-[N'-(o-toluyl)-urea]-pyrid-5-ylmethyl- | 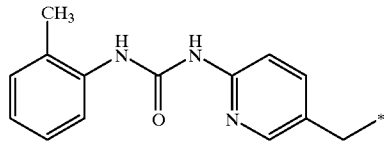 | (4.1.20) |
| 4-[3-(4-methyl-pyridin-3-yl)-ureido]-phenylmethyl- | 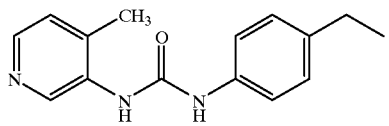 | (4.1.21) |
| 4-[3-(2,6-dichloro-phenyl)-ureido]-phenylmethyl- | 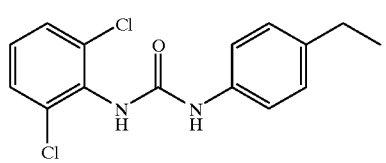 | (4.1.22) |
| 4-[3-(2,6-dimethyl-phenyl)-ureido]-phenylmethyl- | 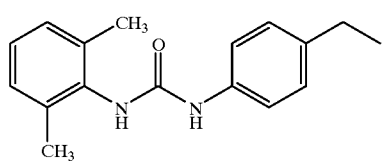 | (4.1.23) |

It will be further noted partial structural formulas that the preferred methylene bridge is also preferably attached to the N,N'-diphenylureido group in a para relationship to the point of attachment of the divalent ureido group to the phenyl group involved.

The "Y" component of Formula (1.0.0) may be —C(=O)—, —C(=S)—; —S(=O)$_2$—; or —CH(R$^a$)—; where R$^a$ has the meaning of hydrogen or (C$_1$–C$_4$) alkyl. Where "Y" is the moiety —CH(R$^a$)—, it is preferred that R$^a$ have the meaning of hydrogen or methyl. Overall, however, it is most preferred that "Y" be a carbonyl moiety, ie., that "Y" is the moiety —C(=O)—.

The next component, the "B" group of the compounds of Formula (1.0.0) is one of the more important portions of the molecule and is a key element in providing the unexpectedly good biological properties possessed by the compounds of the present invention. The "B" group comprises a member selected from the group consisting of partial Formulas (1.1.0) through (1.1.14):

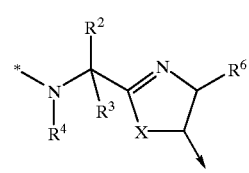

(1.1.0)

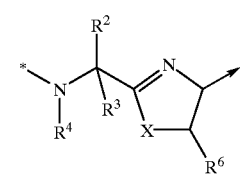

(1.1.1)

-continued (1.1.2) 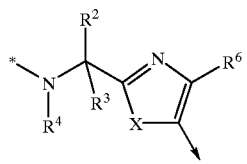

(1.1.3) 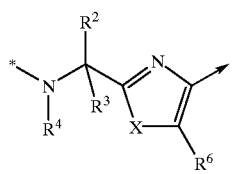

(1.1.4) 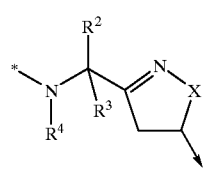

(1.1.5) 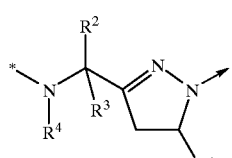

(1.1.6) 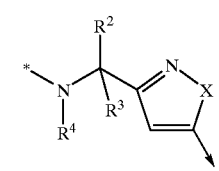

(1.1.7) 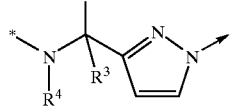

(1.1.8) 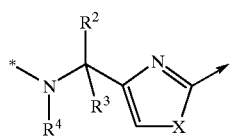

(1.1.9) 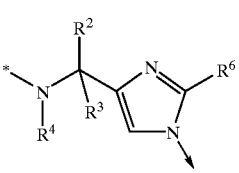

(1.1.10) 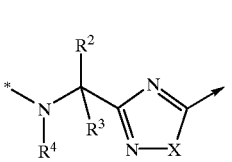

-continued (1.1.11) 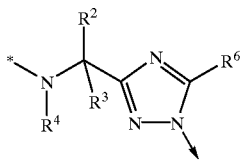

(1.1.12) 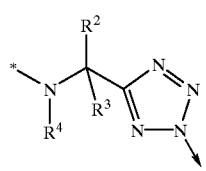

(1.1.13) 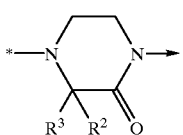

(1.1.14) 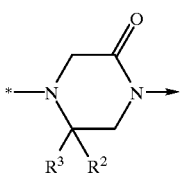

where the symbol "*" indicates the point of attachment of the moiety represented by each partial Formula (1.1.0) through (1.1.14) to the moiety "Y" in Formula (1.0.0); and the symbol "→" indicates the point of attachment of the moiety represented by each partial Formula (1.1.0) through (1.1.14) to the moiety "E" in Formula (1.0.0).

All of the above partial Formulas (1.1.0) through (1.1.14) inclusive are illustrated as fragments in the manner above-described, wherein the points of attachment at either end of a particular fragment are indicated by the symbols "*" and "→".

In the above partial formulas defining the B component of the compounds of Formula (1.0.0), the moiety "X" may be oxygen; sulfur (q=0) and sulfur to which two oxygen atoms is attached (q=2), ie., sulfonyl; or nitrogen ($R^{14}$=hydrogen) or nitrogen which is substituted ($R^{14}$=($C_1$–$C_4$)alkyl; ($C_3$–$C_6$) cycloalkyl; or aryl). It is preferred, however, that "X" be simply oxygen, sulfur or nitrogen.

In the above partial formulas defining the B component of the compounds of Formula (1.0.0), $R^2$ and $R^3$ are independently selected from the group consisting of hydrogen; ($C_1$–$C_4$) alkyl substituted with 0 to 3 $R_{13}$; ($C_2$–$C_6$) alkenyl substituted with 0 to 3 $R^{13}$; a ($C_3$–$C_{14}$) carbocyclic ring system substituted with 0 to 3 $R^{13}$; ($C_1$–$C_4$) alkoxycarbonylamino-($C_1$–$C_4$)alkyl-; ($C_1$–$C_4$)alkylthio-($C_1$–$C_4$)alkyl-; ($C_1$–$C_4$)alkyl-sulfonyl-($C_1$–$C_4$)alkyl-; hydroxy($C_1$–$C_4$)alkylthio-($C_1$–$C_4$)alkyl-; ($C_1$–$C_4$) alkylcarbonylamino-($C_1$–$C_4$)alkyl-; ($C_1$–$C_4$) alkylsulfonylamino-($C_1$–$C_4$)alkyl-; ($C_1$–$C_4$) alkylsulfonylaminocarbonyl-($C_1$–$C_4$)alkyl-; and a heterocyclyl ring substituted with 0 to 3 $R^{13}$; provided that $R^2$ and $R^3$ are not both hydrogen at the same time. This proviso is also satisfied where $R^2$ and $R^3$ are taken together in accordance with an optional definition of $R^2$ and $R^3$, in which case they form a spirocyclic ($C_3$–$C_{14}$) carbocyclic ring substituted with 0 to 3 $R^{13}$. For example, where $R^2$ and $R^3$ are taken together to form a spirocyclic cyclopropyl, cyclobutyl, or cyclopentyl group, the resulting compounds of the present invention will include moieties such as those of partial Formulas (1.2.0) through (1.2.2):

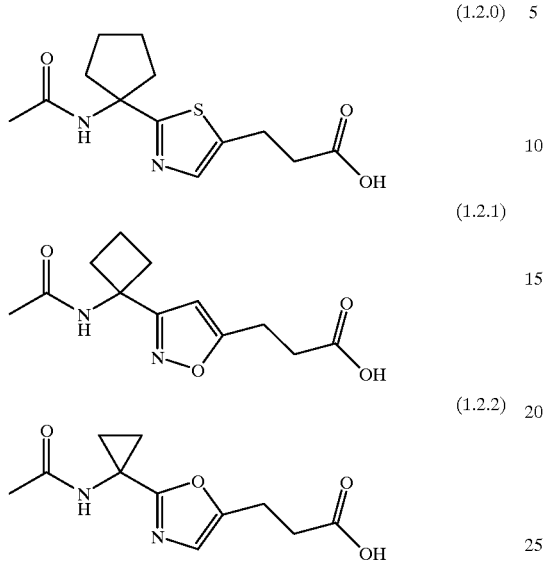

Another preferred sub-group of compounds of the present invention is that formed when either $R^2$ or $R^3$ is taken together with $R^4$ and the carbon and nitrogen atoms to which they are respectively attached to form a heteroaryl or heterocyclyl group as defined herein. Said heteroaryl or heterocyclycl group may, in turn, be substituted with 0 to 3 $R^{12}$. In accordance with the above-mentioned proviso, when either $R^2$ or $R^3$ is taken together with $R^4$, the other must be hydrogen or methyl. The sub-group may be represented by partial Formula (1.3.0) as follows:

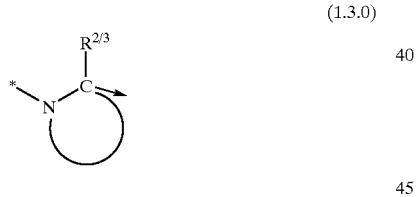

where the symbol "*" indicates the point of attachment of the moiety represented by partial Formula (1.3.0) to the moiety "Y" in Formula (1.0.0); and the symbol "→" indicates the point of attachment of the moiety represented by partial Formula (1.3.0) to the remaining portion of the moiety "B" in Formula (1.0.0), defined by partial Formulas (1.1.0) through (1.1.14). The substituent "$R^{2/3}$" indicates the presence of either the $R^2$ substituent or the $R^3$ substituent. They both may not be present, since one or the other has already been selected to be taken together with $R^4$ to form the heteroaryl or heterocyclyl group of partial Formula (1.3.0), represented as follows:

It will be understood that whether $R^2$ or $R^3$ is present, it will have the meaning of hydrogen or methyl.

Accordingly, this sub-group of the group "B" represented by partial Formula (1.3.0) includes, but is not limited to, the embodiments which are represented by partial Formulas (1.3.1) through (1.3.20):

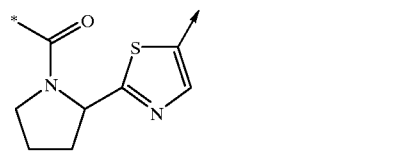

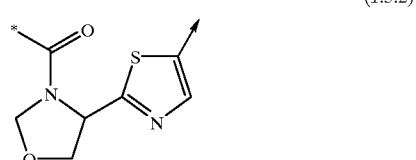

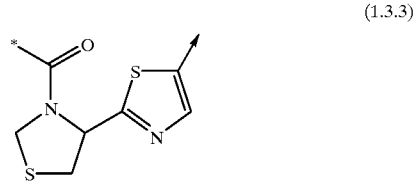

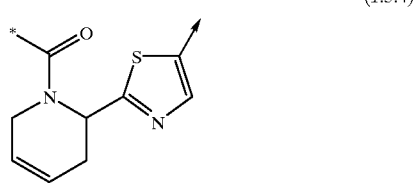

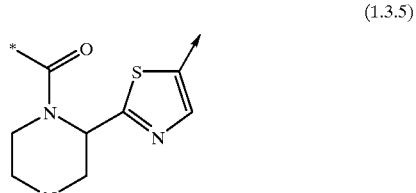

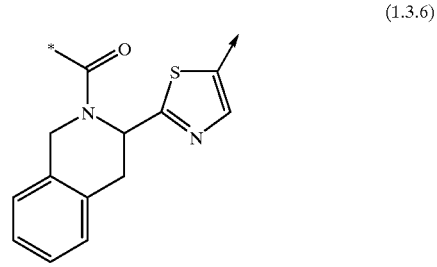

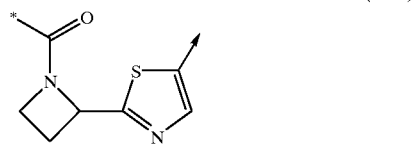

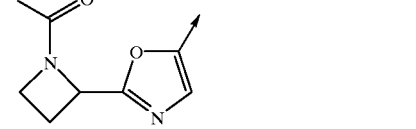

(1.3.9) 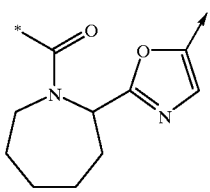

(1.3.10) 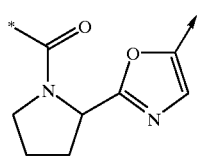

(1.3.11) 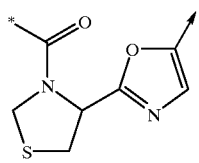

(1.3.12) 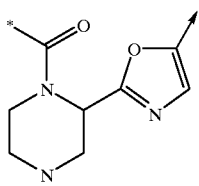

(1.3.13) 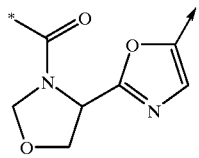

(1.3.14) 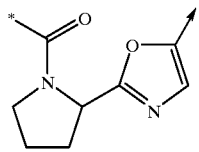

(1.3.15) 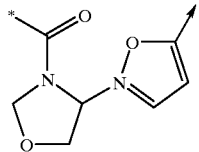

(1.3.16) 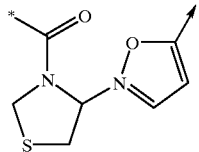

(1.3.17) 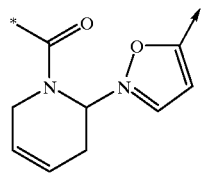

(1.3.18) 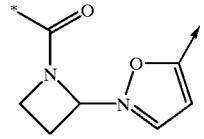

(1.3.19) 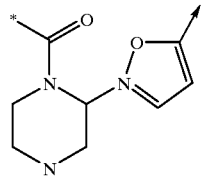

(1.3.20) 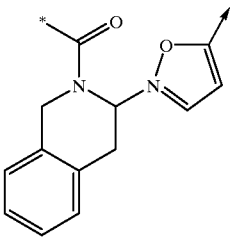

where the symbol "*" indicates the point of attachment of the moiety represented by each partial Formula (1.3.1) through (1.3.20) to the moiety "Y" in Formula (1.0.0); and the symbol "→" indicates the point of attachment of the moiety represented by each partial Formula (1.3.1) through (1.3.20) to the moiety "E" in Formula (1.0.0).

With reference to the optional substituent $R^{13}$ which may be present on the $R^2$ and $R^3$ substituents of the B component, $R^{13}$ is absent when "0" is selected. It is preferred that $R^{13}$ either be absent or be present as a single substituent selected from aryl; heteroaryl; heterocyclyl; $(C_1-C_4)$alkoxy; $(C_3-C_6)$ cycloalkyl; $(C_2-C_6)$alkynyl; —$OR^{14}$; heterocyclyl-carbonyl; $(C_1-C_4)$alkylthio; —$NR^{14}R^5$; and —C(=O)$NR^{14}R^{14'}$. With reference to the optional substituent $R^{13}$, but also with reference to the remainder of the instant specification, the term "alkynyl" alone or in combination, refers to a straight-chain or branched-chain alkynyl radical containing from 2 to 6, preferably 2 to 4 carbon atoms. Examples of such radicals include, but are not limited to, ethynyl (acetylenyl), propynyl, propargyl, butynyl, hexynyl, decynyl and the like.

The term "alkylthio", alone or in combination with other terms, is used herein to refer to a thioether radical of the formula alkyl-S—, where the alkyl component thereof is a straight-chain or branched-chain alkyl radical containing from 1 to 4 carbon atoms, and preferably from 1 to 2 carbon atoms. Thus, an example of such an alkylthio substituent includes, but is not limited to, methylthio and iso-butylthio.

Regarding the definitions of the substituents $R^2$ and $R^3$ on component B, the term "alkoxycarbonylaminoalkyl", alone or in combination, refers to a radical of formula alkyl-OC(=O)NH-alkyl-, wherein both of the terms "alkyl" are as defined above. The term "alkylthioalkyl", used alone or in combination, refers to a thioether radical joined to the B component by an alkyl moiety, of the formula alkyl-S-alkyl-, wherein both of the terms "alkyl" are as defined above. The term "alkylsufonylalkyl", alone or in combination, refers to a radical of the formula alkyl-S(=O)$_2$-alkyl-, wherein both of the terms "alkyl" are as defined above. The term "alkylcarbonylamino", alone or in combination, refers to a radical of formula alkyl-C(=O)NH-alkyl-, wherein both of the terms "alkyl" are as defined above. The term "alkylsulfonylaminoalkyl", alone or in combination, refers to a radical of formula alkyl-S(=O)$_2$—NH-alkyl-, wherein both of the terms "alkyl" are as defined above. The term "(C$_1$–C$_4$) alkylsulfonylaminocarbonyl-(C$_1$–C$_4$) alkyl-", alone or in combination, refers to a radical of formula alkyl-S(=O)$_2$—NH—C(=O)-alkyl, wherein both of the terms "alkyl" are as defined above.

With reference to component "B" of the compounds of Formula (1.0.0), the term "alkenyl", used in this as well as in other contexts throughout the instant specification, used alone or in combination, is intended to refer to a straight-chain or branched-chain alkenyl radical containing from 2 to 6 carbon atoms, preferably from 2 to 4 carbon atoms. Examples of such radicals include, but are not limited to, ethenyl, E- and Z-propenyl, iso-propenyl, E- and Z-butenyl, E- and Z-iso-butenyl, and E- and Z-pentenyl.

The term "(C$_3$–C$_{14}$)carbocyclic ring system" as used with reference to "B", as well as in other contexts throughout the instant specification, used alone or in combination, is intended to refer to cycloalkyl and cycloalkenyl groups consisting of one, two or three fused rings containing a total of from three to fourteen carbon atoms. The term "cycloalkyl" in turn, means a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl and the like. The term "cycloalkenyl" on the other hand, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, and cyclopentadienyl.

Where two or three fused rings are present, one of the rings may be a cycloalkyl ring system while the other one or two rings may be cycloalkenyl ring systems.

It is preferred that when one of R$^2$ and R$^3$ is hydrogen that the other be selected from the group consisting essentially of iso-propyl, sec-butyl, iso-butyl, and tert-butyl; E- and Z-iso-butenyl, and E- and Z-pentenyl; cyclopentyl and cyclohexyl; cyclohexenyl, and cyclopentadienyl; phenyl, indenyl and indanyl; 2-(methylthio)ethyl; 3-(hydroxypropylthio)methyl; 2-(methylsulfonyl)ethyl; 4-(acetylamino)butyl; 4-(methylsulfonylamino)butyl; and 4-ethoxycarbonyl-amino)butyl.

Attached to component B in the compounds of Formula (1.0.0) are the remaining structural elements which may be represented by partial Formula (1.4.0):

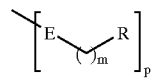

(1.4.0)

It will be noted first that the moiety represented by partial Formula (I) is directly attached to component B in the overall compound of Formula (1.0.0), and that p is an integer independently selected from 1 and 2, so that either one or two of the moieties of Formula (1.4.0) may be attached to component B. Ordinarily, in the preferred embodiments of the compounds of Formula (1.0.0) "p" will be selected as the integer 1. Moreover, certain partial Formula (1.1.2) etc. definitions of B do not permit "p" to be selected as the integer 2. Accordingly, the definition of "p" carries with it the proviso that "p must be selected as 1 where B is selected as partial Formula (1.1.2), (1.1.3), (1.1.5); (1.1.6), (1.1.7), (1.1.8), (1.1.9), (1.1.10), (1.1.11), (1.1.12), (1.1.13) or (1.1.14). Nevertheless, there are embodiments of the compounds of Formula (1.0.0) in which "p" will be selected as the integer 2. An example of such a compound is represented by Formula (1.6.0):

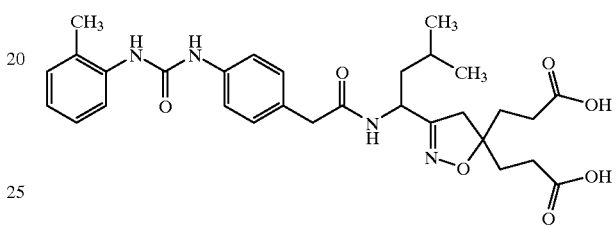

E is a single bond; oxygen; 1,1-cyclopropyl; C(CH$_3$)$_2$; CF$_2$; or is a bridging moiety of partial Formula (1.9.0):

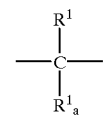

(1.9.0)

Where E is defined as a single bond, a particular group of compounds of Formula (1.0.0) is provided for which is characterized by a carboxylic acid or carboxylic acid fragment terminus of reduced size. Thus, where "m" is selected as the integer 0, the terminus attached to component B comprises the moiety: [—R]$_p$ in which "p" would preferably be selected as the integer 1.

In most of the preferred embodiments of the present invention, however, E is defined as the bridging moiety of partial Formula (1.9.0) above. This bridging moiety comprises a substituted methylene group to which is attached substituent R$^1$ and R$^1_a$, where R$^1_a$ is hydrogen when R$^1$ has the meaning of a mono-valent substituent; and R$^1_a$ is a single bond when R$^1$ has the meaning of a di-valent substituent. In the most preferred embodiments when R$^1$ is a di-valent substituent, it has the meaning =O. A representative compound of the present invention in which E has the meaning of partial Formula (1.9.0), R$^1_a$ is a single bond, and R$^1$ has the meaning of the di-valent substituent =O, is that represented by Formula (1.4.2):

(1.4.2)

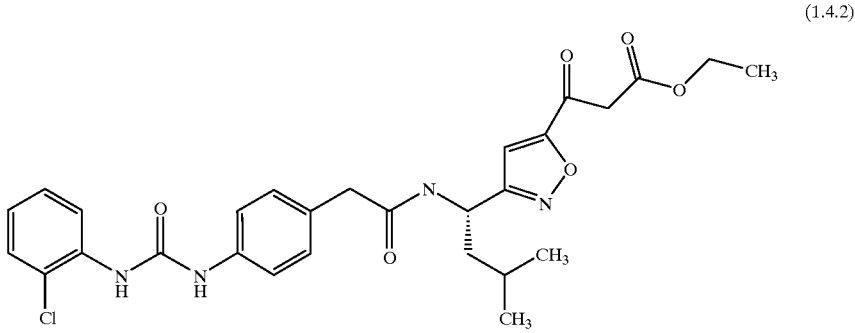

In the portions of the compounds of the present invention represented by partial Formula (1.4.0) above, the moiety E is followed by an optional methylene or ethylene bridge: $(-CH_2-)_m$ where m is an integer independently selected from 0, 1 and 2. It is preferred that an ethylene bridge be present, and it is even more preferred that a methylene bridge be present. In effect the preferred compounds of the present invention thus have an ethylene or propylene bridge between the "B" and "R" components of Formula (1.0.0) and substituent $R^1$ is therefore attached at the α-position of this ethylene or propylene bridge. It is possible for the $R^1$ substituent to be absent, i.e., for $R^1$ to be hydrogen, and this is the preferred structure in many of the compounds of Formula (1.0.0). Nevertheless, there are a number of other compounds of Formula (1.0.0) in which it is preferred that the $R^1$ substituent be present.

Accordingly, $R^1$ is selected from, in addition to hydrogen, the following: =O; =S; F; $CF_3$; $(C_1-C_6)$alkyl substituted with 0 to 3 $R^{10}$; $(C_2-C_6)$alkenyl substituted with 0 to 3 $R^{10}$; $(C_2-C_6)$alkynyl substituted with 0 to 3 $R^{10}$; a $(C_3-C_{14})$ carbocyclic ring system substituted with 0 to 3 $R^{12}$; aryl substituted with 0 to 3 $R^{12}$, and aryl$(C_1-C_4)$alkyl wherein said aryl and alkyl are substituted with 0 to 3 $R^{12}$; heterocyclyl substituted with 0 to 3 $R^{12}$; and heterocyclyl$(C_1-C_4)$ alkyl wherein said heterocyclyl and alkyl are substituted with 0 to 3 $R^{12}$; and $C(=O)NR^8R^9$, and $C(=O)R^8$.

The groups $(C_1-C_6)$alkyl and $(C_2-C_6)$alkenyl have already been defined in detail above. Within the meaning of these groups it is preferred that $R^1$ be methyl, ethyl, isopropyl, tert-butyl, 2-propenyl, or 1-, 2-, or 3-butenyl.

$R^1$ may also be $(C_2-C_6)$alkynyl. The term "alkynyl" as used with reference to "$R^1$", as well as in other contexts throughout the instant specification, used alone or in combination, refers to a straight-chain or branched-chain alkynyl radical containing from 2 to 6 carbon atoms. Examples of such radicals include, but are not limited to, ethynyl (acetylenyl), 1-propynyl, propargyl (2-propynyl), butynyl and hexynyl. Where $R^1$ is alkynyl, it is preferred that it be ethynyl or propargyl $R^1$ may also be a $(C_3-C_{14})$carbocyclic ring system substituted with 0 to 3 $R^{12}$. The meaning of "$(C_3-C_{14})$ carbocyclic ring system" has already been described in detail above, but it is preferred that where $R^1$ is selected from this group, that it be cyclopropyl or cyclopentyl.

$R^1$ may further be aryl substituted with 0 to 3 $R^{12}$; or aryl$(C_1-C_4)$alkyl wherein said aryl and alkyl are substituted with 0 to 3 $R^{12}$. The meaning of "aryl" and of "$(C_1-C_4)$ alkyl" have already been described in detail above, but it is preferred that where $R^1$ is selected from this group, that it be phenyl, phenylmethyl or phenylethyl. Preferred embodiments within these definitions are those which include one or two $R^{12}$ groups as substituents.

The choice of $R^{12}$ substituent depends on the location of the $R^{12}$ substituent. In this case the $R^{12}$ substituent is located on an aryl or arylalkyl group, and thus will be attached to a carbon atom. When $R^{12}$ is a substituent on a carbon atom, it is independently selected as a member from among several groups, one of which consists essentially of F; Cl; $(C_1-C_4)$ alkyl; $(C_3-C_6)$cycloalkyl; $(C_1-C_4)$alkoxy; $-C(=O)OR^{14}$; $-OH$; $(C_1-C_4)$alkyl and $(C_1-C_4)$alkoxy, each substituted with 1 to 3 substituents independently selected from F and Cl; $(C_1-C_4)$alkoxycarbonyl; $(C_1-C_4)$alkylcarbonyl; and $(C_1-C_4)$alkylcarbonyloxy. Particularly preferred substituents from this group are methyl, methoxy, F, Cl, and —OH.

Another group whose members may define $R^{12}$ when attached to a carbon atom consists essentially of a 5- or 6-membered heteroaryl or heterocyclic ring containing from 1 to 4 heteroatoms independently selected from oxygen, nitrogen and sulfur; and a 3- or 4-carbon chain attached to adjacent carbons where an aryl ring to form a fused 9- or 10-membered ring, said 9- or 10-membered fused ring being optionally mono- or di-substituted on the aliphatic carbon atoms thereof with F, Cl, $(C_1-C_4)$alkyl, $(C_1-C_4)$alkoxy, or hydroxy. Preferred heteroaryl substituents comprising $R^{12}$ in this group are furyl, thienyl, pyrrolyl, oxazolyl, isoxazolyl, thiazolyl, imidazolyl, pyridyl, pyrazinyl, pyrazolyl, pyrimidinyl, oxadiazolyl, thiadiazolyl, parathiazinyl, indolyl, benzo[b]furanyl, benzimidazolyl, benzthiazolyl, quinolinyl, and isoquinolinyl. More preferably, $R^{12}$ is pyrrolyl, imidazolyl, oxazolyl or indolyl. Preferred heterocyclyl substituents comprising $R^{12}$ in this group are oxiranyl, pyrrolidinyl, pyrazolidinyl, imidazolidinyl, tetrazolidinyl, piperidinyl, piperazinyl, morpholinyl, thiomorpholinyl, and benzodioxolane, especially 1,3-benzodioxol-5-yl. It is more preferred that where $R^{12}$ is heterocyclyl that it is pyrrolidinyl, piperidinyl, piperazinyl, or morpholinyl.

When $R^{12}$ is attached to a saturated carbon atom, it may be =O or =S; or when $R^{12}$ is attached to a sulfur atom, it may be =O. Especially preferred are ketones formed from hetercyclyl substituents, e.g., the pyrrolidinones, pyrazolidinones, imidazolidinones, tetrazolidinones, piperidinones, and piperazinones. Where $R^{12}$ is attached to a sulfur atom and is defined as $(=O)_{1\ or\ 2}$, it is preferred that there be two (=O), affording a sulfonyl group.

When $R^{12}$ is a substituent on a nitrogen atom, it is independently selected from the group consisting essentially of hydroxy; hydroxy$(C_1-C_4)$alkyl; $(C_1-C_4)$alkoxy; $(C_3-C_6)$ cycloalkyl; $(C_1-C_4)$alkylcarbonyl; and aryl.

Above-mentioned substituent $R^1$ in partial Formula (1.9.0), which in turn represents one of the meanings of basic component E of the compounds of Formula (1.0.0), may be further defined as heterocyclyl substituted with 0 to 3 $R^{12}$; and heterocyclyl($C_1$–$C_4$)alkyl wherein said heterocyclyl and alkyl are substituted with 0 to 3 $R^{12}$. The optional $R^{12}$ substituents on these heterocyclyl and heterocyclylalkyl groups are as described further above. A particular and preferred meaning of heterocyclyl is that of a benzo-fused ring system comprising a dioxolane, for example where $R^1$ is 1,3-benzodioxol-5-yl. This particular heterocyclyl group is viewed as being structurally analogous to a 3,4-dimethoxyphenyl group, a 3,4-difluorophenyl group, or a benzo-1,4-dioxanyl group, as illustrated by their respective partial Formulas (3.1.0), (3.1.1), (3.1.2), and (3.1.3):

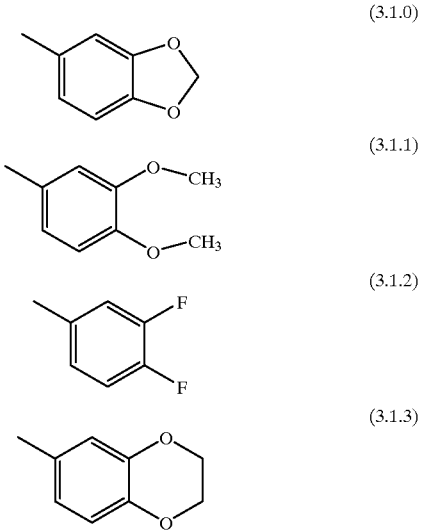

The $R^1$ basic component of the compounds of Formula (1.0.0) may also be C(=O)$NR^8R^9$ or C(=O)$R^8$, where $R^8$ and $R^9$ are independently selected from hydrogen; ($C_1$–$C_4$) alkyl substituted with 0 to 3 $R^{10}$; a ($C_3$–$C_{14}$)carbocyclic ring system substituted with 0 to 3 $R^{12}$; aryl substituted with 0 to 3 $R^{12}$; and aryl($C_1$–$C_4$)alkyl wherein said aryl and alkyl are substituted with 0 to 3 $R^{12}$; heterocyclyl substituted with 0 to 3 $R^{12}$; and heterocyclyl($C_1$–$C_4$)alkyl wherein said heterocyclyl and alkyl are substituted with 0 to 3 $R^{12}$. The $R^{10}$ and $R^{12}$ substituents are as described further above.

Finally, the "R" component of Formula (1.0.0) is independently selected from the group consisting of -tetrazolyl; —C(=O)—$OR^5$; —C(=O)($CH_2$)$_k$C(=O)$OR^5$; —C(=O) NO•; —C(=O)—NH—S(=O)$_2R^5$; —S(=O)$_2$—$NR^{14}R^5$; —C(=O)NHS(=O)$_2R^6$; and a moiety of partial Formula (3.0.0):

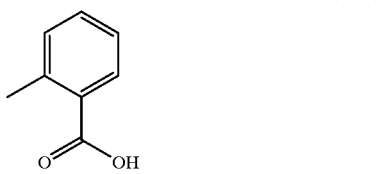

It is preferred that R is C(=O)—OH. However, in addition to such simple carboxylic acids, other preferred embodiments of R include α-, β- and γ-keto acids included within the scope of the partial formula: —C(=O)($CH_2$)$_k$C(=O) $OR^5$. Where k is 0, an α-keto acid such as pyruvic acid is included. Where k is 1, a β-keto acid such as acetoacetic acid is included. Where k is 2, a γ-keto acid such as levulinic acid is included.

The R component also includes moieties derived from sulfamic acid, $H_2NSO_3H$, defined by the partial formula: —S(=O)$_2$—$NR^{14}R^5$, as well as sulfonamidocarbonyl moieties defined by the partial formulas: —C(=O)—NH—S (=O)$_2R^5$ and —C(=O)NHS(=O)$_2R^6$.

Included within the scope of the present invention are the pharmaceutically acceptable derivatives of the compounds of Formula (1.0.0). The expression "pharmaceutically acceptable derivative" as used in the instant specification denotes any pharmaceutically acceptable salt of a compound of Formula (1.0.0). Further included within the scope of the present invention is any other compound which, upon administration to a patient, is capable of directly or indirectly providing a compound of Formula (1.0.0). Such compounds are recognized as prodrugs, and a number of established procedures are available for preparing such prodrug forms of the compounds of Formula (1.0.0).

The term "patient" as used above and throughout the instant specification, refers to mammals, including humans. And where the term "cell" is used it refers to mammalian cells, including human cells, unless otherwise specified.

Further included within the scope of the present invention are metabolites or residues of the compounds of Formula (1.0.0) which possess biological activity such that they are able to inhibit cell adhesion and consequent or associated pathogenic processes subsequently mediated by VLA-4. Once synthesized, the inhibitory activities and VLA-4 specificities of the compounds of Formula (1.0.0) according to this invention may be determined using in vitro and in vivo assays which are described in detail further below.

The desirable biological activity of the compounds of Formula (1.0.0) may also be improved by appending thereto appropriate functionalities which will function to enhance existing biological properties of the compound, improve the selectivity of the compound for the existing biological activities, or add to the existing biological activities further desirable biological activities. Such modifications are known in the art and include those which increase biological penetration into a given biological system, e.g., blood, the lymphatic system, and central nervous system; increase oral availability; increase solubility to allow administration by injection; alter metabolism; and alter the rate of excretion of the compound of Formula (1.0.0).

In view of the above definitions and others throughout the instant specification, other chemical and biological terms used herein can be easily understood by those of skill in the art. The defined terms may be used alone or in any combination thereof. The preferred and more preferred chain lengths of the radicals which have been specified herein apply to all such combinations.

Further pursuant to the descriptions above of certain preferred subgeneric and more preferred subgeneric definitions of the compounds of Formula (1.0.0), there follows an enumeration of preferred and more preferred species in order to provide a further illustration of the present invention.

Compounds which include the moiety of partial Formula (1.1.0):
3-[2-(3-Methyl-1-{2-[4-(3-o-tolyl-ureido)-phenyl]-acetylamino}-butyl)4,5-dihydro-oxazol-5-yl]-propionic acid;
3-[2-(3-Methyl-1-{2-[4-(3-{2-fluorophenyl}-ureido)-phenyl]-acetylamino}-butyl)-4,5-dihydro-oxazol-5-yl]-propionic acid;
2-[2-(3-Methyl-1-{2-[4-(3-{2-cyclopentylphenyl}-ureido)-phenyl]-acetylamino}-butyl)-4,5-dihydro-oxazol-5-yl]-acetic acid;

4-[2-(3-Methyl-1-{2-[4-(3-{3-methylpyrid-2-yl}-ureido)-phenyl]-acetylamino}-butyl)-4,5-dihydro-oxazol-5-yl]-butyric acid;

3-[2-(3-Methyl-1-{2-[4-(3-{3-cyclopentylpyrid-2-yl}-ureido)-phenyl]-acetylamino}-butyl)-4,5-dihydro-oxazol-5-yl]-propionic acid;

3-[2-(3-Methyl-1-{2-[3-methoxy-4-(3-o-tolyl-ureido)-phenyl]-acetylamino}-butyl)-4,5-dihydro-oxazol-5-yl]-propionic acid;

3-[2-(3-Methyl-1-{2-[3-methyl-4-(3-{pyrid-2-yl}-ureido)-phenyl]-acetylamino}-butyl)-4,5-dihydro-thiazol-5-yl]-propionic acid;

2-[2-(3-Methyl-1-{2-[3-fluoro-4-(3-{pyrid-2-yl}-ureido)-phenyl]-acetylamino}-butyl)-4,5-dihydro-thiazol-5-yl]-acetic acid;

3-[2-(3-Methyl-1-{2-[3-methoxy-4-(3-{3-methoxypyrid-2-yl}-ureido)-phenyl]-acetylamino}-butyl)-1,1-dioxo-4,5-dihydro-thiazol-5-yl]-propionic acid;

3-[2-(3-Methyl-1-{2-[3-methyl-4-(3-{3-methylpyrid-2-yl}-ureido)-phenyl]--acetylamino}-butyl)-4,5-dihydro-imidazol-5-yl]-propionic acid;

4-[2-(3-Methyl-1-{2-[3-fluoro-4-(3-{3-methylpyrid-2-yl}-ureido)-phenyl-acetylamino}-butyl)-4,5-dihydro-imidazol-5-yl]-butyric acid;

3-[2-(3-Methyl-1-{2-[3-methyl-4-(3-{3-cyclopentylpyrid-2-yl}-ureido)-phenyl]-acetylamino}-butyl)-4,5-dihydro-imidazol-5-yl]-propionic acid;

2-[2-(3-Methyl-1-{2-[3-fluoro-4-(3-{3-cyclopentylpyrid-2-yl}-ureido)-phenyl]-acetylamino}-butyl)-4,5-dihydro-imidazol-5-yl]-acetic acid;

3-{2-[1-(2-{4-[3-(2-Chloro-phenyl)-ureido]-phenyl}-acetylamino)-3-methyl-butyl]-thiazol-5-yl}-propionic acid;

3-{2-[1-(2-{4-[3-(2-Methoxy-phenyl)-ureido]-phenyl}-acetylamino)-3-methyl-butyl]-thiazol-5-yl}-propionic acid;

3-{2-[1-(2-{4-[3-(2-Fluoro-phenyl)-ureido]-phenyl}-acetylamino)-3-methyl-butyl]-thiazol-5-yl}-propionic acid;

3-{2-[1-(2-{4-[3-(2,6-Dichloro-phenyl)-ureido]-phenyl}-acetylamino)-3-methyl-butyl]-thiazol-5-yl}-propionic acid;

3-{2-[1-(2-{4-[3-(2,6-Dimethyl-phenyl)-ureido]-phenyl}-acetylamino)-3-methyl-butyl]-thiazol-5-yl}-propionic acid;

3-{2-[1-(2-{4-[3-(2-Chloro-6-methyl-phenyl)-ureido]-phenyl}-acetylamino)-3-methyl-butyl]-thiazol-5-yl}-propionic acid;

3-[2-(3-Methyl-1-{2-[4-(3-phenyl-ureido)-phenyl]-acetylamino}-butyl)-thiazol-5-yl]-propionic acid;

N-Hydroxy-3-[2-(3-methyl-1-{2-[4-(3-o-tolyl-ureido)-phenyl]-acetylamino}-butyl)-thiazol-5-yl]-propionamide;

3-[2-(1-{2-[4-(3-o-Tolyl-ureido)-phenyl]-acetylamino}-but-3-enyl)-thiazol-5-yl]-propionic acid, 3-[2-(1-{2-[4-(3-o-Tolyl-ureido)-phenyl]-acetylamino}-butyl)-thiazol-5-yl]-propionic acid;

N-{1-[5-(3-Methanesulfonylamino-3-oxo-propyl)-thiazol-2-yl]-3-methyl-butyl}-2-[4-(3-o-tolyl-ureido)-phenyl]-acetamide;

2-{4-[3-(2-Chloro-phenyl)-ureido]-phenyl}-N-{1-[5-(3-methanesulfonylamino-3-oxo-propyl)-thiazol-2-yl]-3-methyl-butyl}-acetamide;

3-[2-({2-[4-(3-o-Tolyl-ureido)-phenyl]-acetylamino}-methyl)-thiazol-5-yl]-propionic acid; and 3-{2-[((2-{4-[3-(2-Chloro-phenyl)-ureido]-phenyl}-acetylamino)-methyl]-thiazol-5-yl}-propionic acid.

Compounds which include the moiety of partial Formula (1.1.1):

3-[2-(3-Methyl-1-{2-[4-(3-o-tolyl-ureido)-phenyl]-acetylamino}-butyl)4,5-dihydro-oxazol-4-yl]-propionic acid;

4-[2-(3-Methyl-1-{2-[4-(3-{3-methylpyrid-2-yl}-ureido)-phenyl]-acetylamino}-butyl)4,5-dihydro-oxazol-4-yl]-butyric acid;

3-[2-(3-Methyl-1-{2-[3-methoxy-4-(3-o-tolyl-ureido)-phenyl]-acetylamino}-butyl)-4,5-dihydro-oxazol-4-yl]-propionic acid;

3-[2-(3-Methyl-1-{2-[3-methyl-4-(3-{pyrid-2-yl}-ureido)-phenyl]-acetylamino}-butyl)-4,5-dihydro-thiazol-4-yl]-propionic acid;

3-[2-(3-Methyl-1-{2-[3-methoxy-4-(3-{3-methoxypyrid-2-yl}-ureido)-phenyl]-acetylamino}-butyl)-1,1-dioxo-4,5-dihydro-thiazol-4-yl]-propionic acid;

3-[2-(3-Methyl-1-{2-[3-methyl-4-(3-{3-methylpyrid-2-yl}-ureido)-phenyl]-acetylamino}-butyl)-4,5-dihydro-imidazol-4-yl]-propionic acid; and 2-[2-(3-Methyl-1-{2-[3-fluoro-4-(3-{3-cyclopentylpyrid-2-yl}-ureido)-phenyl]-acetylamino}-butyl)-4,5-dihydro-imidazol-4-yl]-acetic acid.

Compounds which include the moiety of partial Formula (1.1.2):

3-[2-(3-Methyl-1-{2-[4-(3-o-tolyl-ureido)-phenyl]-acetylamino}-butyl)-oxazol-5-yl]-propionic acid;

3-[2-(3-Methyl-1-{2-[4-(3-o-tolyl-ureido)-phenyl]-acetylamino}-butyl)-oxazol-5-yl]-propionic acid;

3-[2-(3-Methyl-1-{2-[4-(3-{2-methoxyphenyl}-ureido)-phenyl]-acetylamino}-butyl)-oxazol-5-yl]-propionic acid;

3-[2-(3-Methyl-1-{2-[4-(3-{pyrid-2-yl}-ureido)-phenyl]-acetylamino}-butyl)-oxazol-5-yl]-propionic acid;

4-[2-(3-Methyl-1-{2-[4-(3-{3-methoxypyrid-2-yl}-ureido)-phenyl]-acetylamino}-butyl)-oxazol-5-yl]-butyric acid;

2-[2-(3-Methyl-1-{2-[3-methyl-4-(3-o-tolyl-ureido)-phenyl]-acetylamino}-butyl)-oxazol-5-yl]-acetic acid;

3-[2-(3-Methyl-1-{2-[3-fluoro-4-(3-o-tolyl-ureido)-phenyl]-acetylamino}-butyl)-oxazol-5-yl]-propionic acid;

3-[2-(3-Methyl-1-{2-[3-methoxy-4-(3-[pyrid-2-yl}-ureido)-phenyl]-acetylamino}-butyl)-thiazol-5-yl]-propionic acid;

3-[2-(3-Methyl-1-{2-[3-methyl-4-(3-{3-methoxypyrid-2-yl}-ureido)-phenyl]-acetylamino}-butyl)-1,1-dioxo-thiazol-5-yl]-propionic acid;

4-[2-(3-Methyl-1-{2-[3-fluoro-4-(3-{3-methoxypyrid-2-yl}-ureido)-phenyl]-acetylamino}-butyl)-thiazol-5-yl]-butyric acid;

3-[2-(3-Methyl-1-{2-[3-methoxy-4-(3-{3-methylpyrid-2-yl}-ureido)-phenyl]-acetylamino}-butyl)-imidazol-5-yl]-propionic acid;

3-[2-(3-Methyl-1-{2-[3-cyclopentyl-4-(3-{3-methylpyrid-2-yl}-ureido)-phenyl]-acetylamino}-butyl)-imidazol-5-yl]-propionic acid;

3-[2-(3-Methyl-1-{2-[3-methoxy-4-(3-{3-cyclopentylpyrid-2-yl}-ureido)-phenyl]-acetylamino}-butyl)-imidazol-5-yl]-propionic acid;

3-[2-(3-Methyl-1-{2-[3-trifluoromethyl-4-(3-{3-cyclopentylpyrid-2-yl}-ureido)-phenyl]-acetylamino}-butyl)-imidazol-5-yl]-propionic acid;

3-{2-[1-(2-{4-[3-(2-Chloro-phenyl)-ureido]-phenyl}-acetylamino)-3-methyl-butyl]-thiazol-5-yl}-propionic acid;

3-{2-[1-(2-{4-[3-(2,6-Dichloro-phenyl)-ureido]-phenyl}-acetylamino)-3-methyl-butyl]-thiazol-5-yl}-propionic acid;

3-{2-[1-(2-{4-[3-(2-Fluoro-phenyl)-ureido]-phenyl}-acetylamino)-3-methyl-butyl]-thiazol-5-yl}-propionic acid;

3-[2-(1-{2-[4-(3-o-tolyl-ureido)-phenyl]-acetylamino}-3-methyl-butyl)-thiazol-5-yl]-propionic acid;

3-{2-[1-(2-{4-[3-(2-Dimethyl-phenyl)-ureido]-phenyl}-acetylamino)-3-methyl-butyl]-thiazol-5-yl}-propionic acid;

3-{2-[1-(2-{4-[3-(2-Chloro-6-methyl-phenyl)-ureido]-phenyl}-acetylamino)-3-methyl-butyl]-thiazol-5-yl}-propionic acid;

3-{2-[1-(2-{4-[3-(2-Methoxy-phenyl)-ureido]-phenyl}-acetylamino)-3-methyl-butyl]-thiazol-5-yl}-propionic acid;

3-{2-[1-(2-{4-[3-(Phenyl)-ureido]-phenyl}-acetylamino)-3-methyl-butyl]-thiazol-5-yl}-propionic acid;

3-[2-(1-{2-[4-(3-o-tolyl-ureido)-phenyl]-acetylamino}-3-butenyl)-thiazol-5-yl]-propionic acid;

3-{2-[1-(2-{4-[3-(2-Methyl-phenyl)-ureido]-phenyl}-acetylamino)-3-methyl-butyl]-thiazol-5-yl}-prop-2-enoic acid;

3-{2-[1-(2-{4-[3-(2-Methyl-phenyl)-ureido]-phenyl}-acetylamino)-3-methyl-butyl]-thiazol-5-yl}-1-hydroximino-propionic acid;

3-{2-[1-(2-{4-[3-(2-Methyl-phenyl)-ureido]-phenyl}-acetylamino)-n-butyl]-thiazol-5-yl}-propionic acid; and 3-{2-[1-(2-{4-[3-(2-Methyl-phenyl)-ureido]-phenyl}-acetylamino)-3-methyl-butyl]-thiazol-5-yl}-1-methylsulfonyl-propionamide.

Compounds which include the moiety of partial Formula (1.1.3):

3-[2-(3-Methyl-1-{2-[4-(3-o-tolyl-ureido)-phenyl]-acetylamino}-butyl)-oxazol-4-yl]-propionic acid;

4-[2-(3-Methyl-1-{2-[4-(3-{3-methylpyrid-2-yl}-ureido)-phenyl]-acetylamino}-butyl)-oxazol-4-yl]-butyric acid;

3-[2-(3-Methyl-1-{2-3-methoxy-4-(3-o-tolyl-ureido)-phenyl]-acetylamino}-butyl)-oxazol-4-yl]-propionic acid;

3-[2-(3-Methyl-1-{2-[3-methyl-4-(3-{pyrid-2-yl}-ureido)-phenyl]-acetylamino}-butyl)-thiazol-4-yl]-propionic acid;

3-[2-(3-Methyl-1-{2-[3-methoxy-4-(3-{3-methoxypyrid-2-yl}-ureido)-phenyl]-acetylamino}-butyl)-1,1-dioxo-thiazol-4-yl]-propionic acid;

3-[2-(3-Methyl-1-{2-[3-methyl-4-(3-{3-methylpyrid-2-yl}-ureido)-phenyl]-acetylamino}-butyl)-imidazol-4-yl]-propionic acid; and 2-[2-(3-Methyl-1-{2-[3-fluoro-4-(3-{3-cyclopentylpyrid-2-yl}-ureido)-phenyl]-acetylamino}-butyl)-imidazol-4-yl]-acetic acid.

Compounds which include the moiety of partial Formula (1.1.4):

3-[3-(3-Methyl-1-{2-[4-(3-o-tolyl-ureido)-phenyl]-acetylamino}-butyl)-4,5-dihydro-isoxazol-5-yl]-propionic acid;

3-[3-(3-Methyl-1-{2-[4(3-{2-fluorophenyl}-ureido)-phenyl]-acetylamino}-butyl)4,5-dihydro-isoxazol-5-yl]-propionic acid;

2-[3-(3-Methyl-1-{2-[4-(3-{2-cyclopentylphenyl}-ureido)-phenyl]-acetylamino}-butyl)-4,5-dihydro-isoxazol-5-yl]-acetic acid;

4-[3-(3-Methyl-1-{2-[4-(3-{3-methylpyrid-2-yl}-ureido)-phenyl]-acetylamino}-butyl)-4,5-dihydro-isoxazol-5-yl]-butyric acid;

3-[3-(3-Methyl-1-{2-[4-(3-{3-cyclopentylpyrid-2-yl}-ureido)-phenyl]-acetylamino}-butyl)-4,5-dihydro-isoxazol-5-yl]-propionic acid; and 3-[3-(3-Methyl-1-{2-[3-methoxy-4-(3-o-tolyl-ureido)-phenyl]-acetylamino}-butyl)-4,5-dihydro-isoxazol-5-yl]-propionic acid.

Compounds which include the moiety of partial Formula (1.1.5):

3-[3-(3-Methyl-1-{2-[4-(3-o-tolyl-ureido)-phenyl]-acetylamino}-butyl)4,5-dihydro-pyrazol-1-yl]-propionic acid;

3-[3-(3-Methyl-1-{2-[4-(3-{2-methoxyphenyl}-ureido)-phenyl]-acetylamino}-butyl)-4,5-dihydro-pyrazol-1-yl]-propionic acid;

3-[3-(3-Methyl-1-{2-[4-(3-{pyrid-2-yl}-ureido)-phenyl]-acetylamino}-butyl)-4,5-dihydro-pyrazol-1-yl]-propionic acid;

4-[3-(3-Methyl-1-{2-[4-(3-{3-methoxypyrid-2-yl}-ureido)-phenyl]-acetylamino}-butyl)-4,5-dihydro-pyrazol-1-yl]-butyric acid;

2-[3-(3-Methyl-1-{2-[3-methyl-4-(3-o-tolyl-ureido)-phenyl]-acetylamino}-butyl)-4,5-dihydro-pyrazol-1-yl]-acetic acid;

3-[3-(3-Methyl-1-{2-[3-fluoro-4-(3-o-tolyl-ureido)-phenyl]-acetylamino}-butyl)-4,5-dihydro-pyrazol-1-yl]-acid;

3-[3-(3-Methyl-1-{2-[3-methoxy-4-(3-{pyrid-2-yl}-ureido)-phenyl]-acetylamino}-butyl)-4,5-dihydro-pyrazol-1-yl]-propionic acid;

4-[3-(3-Methyl-1-{2-[3-fluoro-4-(3-{3-methoxypyrid-2-yl}-ureido)-phenyl]-acetylamino}-butyl)-4,5-dihydro-pyrazol-1-yl]-butyric acid;

3-[3-(3-Methyl-1-{2-[3-methoxy-4-(3-{3-methylpyrid-2-yl}-ureido)-phenyl]-acetylamino}-butyl)-4,5-dihydro-pyrazol-1-yl]-propionic acid;

3-[3-(3-Methyl-1-{2-[3-cyclopentyl-4-(3-{3-methylpyrid-2-yl}-ureido)-phenyl]-acetylamino}-butyl)-4,5-dihydro-pyrazol-1-yl]-propionic acid;

3-[3-(3-Methyl-1-{2-[3-methoxy-4-(3-{3-cyclopentylpyrid-2-yl}-ureido)-phenyl]-acetylamino}-butyl)-4,5-dihydro-pyrazol-1-yl]-propionic acid; and 3-[3-(3-Methyl-1-{2-[3-trifluoromethyl-4-(3-{3-cyclopentylpyrid-2-yl}-ureido)-phenyl]-acetylamino}-butyl)-4,5-dihydro-pyrazol-1-yl]-propionic acid;

Compounds which include the moiety of partial Formula (1.1.6):

3-[3-(3-Methyl-1-{2-[4-(3-o-tolyl-ureido)-phenyl]-acetylamino}-butyl)-isoxazol-5-yl]-propionic acid;

3-[3-(3-Methyl-1-{2-[4-(3-{2-fluorophenyl}-ureido)-phenyl]-acetylamino}-butyl)-isoxazol-5-yl]-propionic acid;

2-[3-(3-Methyl-1-{2-[4-(3-{2-cyclopentylphenyl}-ureido)-phenyl]-acetylamino}-butyl)-isoxazol-5-yl]-acetic acid;

4-[3-(3-Methyl-1-{2-[4-(3-{3-methylpyrid-2-yl}ureido)-phenyl]-acetylamino}-butyl)-isoxazol-5-yl]-butyric acid;

3-[3-(3-Methyl-1-{2-[4-(3-{3-cyclopentylpyrid-2-yl}-ureido)-phenyl]-acetylamino}-butyl)-isoxazol-5-yl]-propionic acid;

3-[3-(3-Methyl-1-{2-[3-methoxy-4-(3-o-tolyl-ureido)-phenyl]-acetylamino}-butyl)-isoxazol-5-yl]-propionic acid;

3-{3-[3-Methyl-1-(2-{4-[3-(4-methyl-pyridin-3-yl)-ureido]-phenyl}-acetylamino)-butyl]-isoxazol-5-yl}-propionic acid;

3-[3-(3-Methyl-1-{2-[4-(3-o-tolyl-ureido)-phenyl]-acetylamino}-butyl)-isoxazol-5-y]-acrylic acid;

3-{3-[1-(2-{4-[3-(2-Chloro-phenyl)-ureido]-phenyl}-acetylamino)-3-methyl-butyl]-isoxazol-5-yl}-propionic acid;

3-{3-[1-(2-{4-[3-(2-Chloro-phenyl)-ureido]-phenyl}-acetylamino)-3-methyl-butyl]-isoxazol-5-yl}-3-oxo-propionic acid ethyl ester;

3-[3-(3-Methyl-1-{2-[4-(3-o-tolyl-ureido)-phenyl]-acetylamino}-butyl)-isoxazol-5-yl]-2-oxo-propionic acid ethyl ester; and 3-[3-(3-Methyl-1-{2-[4-(3-o-tolyl-ureido)-phenyl]-acetylamino}-butyl)-isoxazol-5-yl]-prop-2-enoic acid.

Compounds which include the moiety of partial Formula (1.1.7):

3-[3-(3-Methyl-1-{2-[4-(3-o-tolyl-ureido)-phenyl]-acetylamino}-butyl)-pyrazol-1-yl]-propionic acid;

3-[3-(3-Methyl-1-{2-[4-(3-{2-methoxyphenyl}-ureido)-phenyl]-acetylamino}-butyl)-pyrazol-1-yl]-propionic acid;

3-[3-(3-Methyl-1-{2-[4-(3-{pyrid-2-yl}-ureido)-phenyl]-acetylamino}-butyl)-pyrazol-1-yl]-propionic acid;

4-[3-(3-Methyl-1-{2-[4-(3-{3-methoxypyrid-2-yl}-ureido)-phenyl]-acetylamino}-butyl)-pyrazol-1-yl]-butyric acid;

2-[3-(3-Methyl-1-{2-[3-methyl-4-(3-o-tolyl-ureido)-phenyl]-acetylamino}-butyl)-pyrazol-1-yl]-acetic acid;

3-[3-(3-Methyl-1-{2-[3-fluoro-4-(3-o-tolyl-ureido)-phenyl]-acetylamino}-butyl)-pyrazol-1-yl]-acid;

3-[3-(3-Methyl-1-{2-[3-methoxy-4-(3-{pyrid-2-yl}-ureido)-phenyl]-acetylamino}-butyl)-pyrazol-1-yl]-propionic acid;

4-[3-(3-Methyl-1-{2-[3-fluoro-4-(3-{3-methoxypyrid-2-yl}-ureido)-phenyl]-acetylamino}-butyl)-pyrazol-1-yl]-butyric acid;

3-[3-(3-Methyl-1-{2-[3-methoxy-4-(3-{3-methylpyrid-2-yl}-ureido)-phenyl]-acetylamino}-butyl)-pyrazol-1-yl]-propionic acid;

3-[3-(3-Methyl-1-{2-[3-cyclopentyl-4-(3-{3-methylpyrid-2-yl}-ureido)-phenyl]-acetylamino}-butyl)-pyrazol-1-yl]-propionic acid;

3-[3-(3-Methyl-1-{2-[3-methoxy-4-(3-{3-cyclopentylpyrid-2-yl}-ureido)-phenyl]-acetylamino}-butyl)-pyrazol-1-yl]-propionic acid;

3-[3-(3-Methyl-1-{2-[3-trifluoromethyl-4-(3-{3-cyclopentylpyrid-2-yl}-ureido)-phenyl]-acetylamino}-butyl)-pyrazol-1-yl]-propionic acid.

Compounds which include the moiety of partial Formula (1.1.8):

3-[4-(3-Methyl-1-{2-[4-(3-o-tolyl-ureido)-phenyl]-acetylamino}-butyl)-oxazol-2-yl]-propionic acid;

3-[4-(3-Methyl-1-{2-[4-(3-o-tolyl-ureido)-phenyl]-acetylamino}-butyl)-oxazol-2-yl]-propionic acid;

3-[4-(3-Methyl-1-{2-[4-(3-{2-methoxyphenyl}-ureido)-phenyl]-acetylamino}-butyl)-oxazol-2-yl]-propionic acid;

3-[4-(3-Methyl-1-{2-[4-(3-{pyrid-2-yl}-ureido)-phenyl]-acetylamino}-butyl)-oxazol-2-yl]-propionic acid;

4-[4-(3-Methyl-1-{2-[4-(3-{3-methoxypyrid-2-yl}-ureido)-phenyl]-acetylamino}-butyl)-oxazol-2-yl]-butyric acid;

2-[4-(3-Methyl-1-{2-[3-methyl-4-(3-o-tolyl-ureido)-phenyl]-acetylamino}-butyl)-oxazol-2-yl]-acetic acid;

3-[4-(3-Methyl-1-{2-[3-fluoro-4-(3-o-tolyl-ureido)-phenyl]-acetylamino}-butyl)-oxazol-2-yl]-propionic acid;

3-[4-(3-Methyl-1-{2-[3-methoxy-4-(3-{pyrid-2-yl}-ureido)-phenyl]-acetylamino}-butyl-thiazol-2-yl]-propionic acid;

3-[4-(3-Methyl-1-{2-[3-methyl-4-(3-{3-methoxypyrid-2-yl}-ureido)-phenyl]-acetylamino}-butyl)-1,1-dioxo-thiazol-2-yl]-propionic acid;

4-[4-(3-Methyl-1-{2-[3-fluoro-4-(3-{3-methoxypyrid-2-yl}-ureido)-phenyl]-acetylamino}-butyl)-thiazol-2-yl]-butyric acid;

3-[4-(3-Methyl-1-{2-[3-methoxy-4-(3-{3-methylpyrid-2-yl}-ureido)-phenyl]-acetylamino}-butyl)-imidazol-2-yl]-propionic acid;

3-[4-(3-Methyl-1-{2-[3-cyclopentyl-4-(3-{3-methylpyrid-2-yl}-ureido)-phenyl]-acetylamino}-butyl)-imidazol-2-yl]-propionic acid;

3-[4-(3-Methyl-1-{2-[3-methoxy-4-(3-{3-cyclopentylpyrid-2-yl}-ureido)-phenyl]-acetylamino}-butyl)-imidazol-2-yl]-propionic acid;

3-[4-(3-Methyl-1-{2-[3-trifluoromethyl-4-(3-{3-cyclopentylpyrid-2-yl}-ureido)-phenyl]-acetylamino}-butyl)-imidazol-2-yl]-propionic acid.

Compounds which include the moiety of partial Formula (1.1.9):

3-[4-(3-Methyl-1-{2-[4-(3-o-tolyl-ureido)-phenyl]-acetylamino}-butyl)-imidazo-1-yl]-propionic acid;

3-[4-(3-Methyl-1-{2-[4-(3-{2-methoxyphenyl}-ureido)-phenyl]-acetylamino}-butyl)-imidazol-1-yl]-propionic acid;

3-[4-(3-Methyl-1-{2-[4-(3-{pyrid-2-yl}-ureido)-phenyl]-acetylamino}-butyl)-imidazol-1-yl]-propionic acid;

4-[4-(3-Methyl-1-{2-[4-(3-{3-methoxypyrid-2-yl}-ureido)-phenyl]-acetylamino}-butyl)-imidazol-1-yl]-butyric acid;

2-[4-(3-Methyl-1-{2-[3-methyl-4-(3-o-tolyl-ureido)-phenyl]-acetylamino}-butyl)-imidazol-1-yl]-acetic acid;

3-[4-(3-Methyl-1-{2-[3-fluoro-4-(3-o-tolyl-ureido)-phenyl]-acetylamino}-butyl)-imidazol-1-yl]-acid;

3-[4-(3-Methyl-1-{2-[3-methoxy-4-(3-{pyrid-2-yl}-ureido)-phenyl]-acetylamino}-butyl)-imidazol-1-yl]-propionic acid;

4-[4-(3-Methyl-1-{2-[3-fluoro-4-(3-{3-methoxypyrid-2-yl}-ureido)-phenyl]-acetylamino}-butyl)-imidazol-1-yl]-butyric acid;

3-[4-(3-Methyl-1-{2-[3-methoxy-4-(3-{3-methylpyrid-2-yl}-ureido)-phenyl]-acetylamino}-butyl)-imidazol-1-yl]-propionic acid;

3-[4-(3-Methyl-1-{2-[3-cyclopentyl-4-(3-{3-methylpyrid-2-yl}-ureido)-phenyl]-acetylamino}-butyl)-imidazol-1-yl]-propionic acid;

3-[4-(3-Methyl-1-{2-[3-methoxy-4-(3-{3-cyclopentylpyrid-2-yl}-ureido)-phenyl]-acetylamino}-butyl)-imidazol-1-yl]-propionic acid;

3-[4-(3-Methyl-1-{2-[3-trifluoromethyl-4-(3-{3-cyclopentylpyrid-2-yl}-ureido)-phenyl]-acetylamino}-butyl)-imidazol-1-yl]-propionic acid Compounds which include the moiety of partial Formula (1.1.10):

3-[3-(3-Methyl-1-{2-[4-(3-o-tolyl-ureido)-phenyl]-acetylamino}-butyl)-1,2,4-oxadiazol-5-yl]-propionic acid;

3-[3-(3-Methyl-1-{2-[4-(3-{2-fluorophenyl}-ureido)-phenyl]-acetylamino}-butyl)-1,2,4-oxadiazol-5-yl]-propionic acid;

2-[3-(3-Methyl-1-{2-[4-(3-{2-cyclopentylphenyl}-ureido)-phenyl]-acetylamino}-butyl)-1,2,4-oxadiazol-5-yl]-acetic acid;

4-[3-(3-Methyl-1-{2-[4-(3-{3-methylpyrid-2-yl}-ureido)-phenyl]-acetylamino}-butyl)-1,2,4-oxadiazol-5-yl]-butyric acid;

3-[3-(3-Methyl-1-{2-[4-(3-{3-cyclopentylpyrid-2-yl}-ureido)-phenyl]-acetylamino}-butyl)-1,2,4-oxadiazol-5-yl]-propionic acid;

3-[3-(3-Methyl-1-{2-[3-methoxy-4-(3-o-tolyl-ureido)-phenyl]-acetylamino}-butyl)-4,5-1,2,4-oxadiazol-5-yl]-propionic acid.

Compounds which include the moiety of partial Formula (1.1.11):

3-[4-(3-Methyl-1-{2-[4-(3-o-tolyl-ureido)-phenyl]-acetylamino}-butyl)-1H-1,2,4-triazol-1-yl]-propionic acid;

3-[4-(3-Methyl-1-{2-[4-(3-{2-methoxyphenyl}-ureido)-phenyl]-acetylamino}-butyl)-1H-1,2,4-triazol-1-yl]-propionic acid;

3-[4-(3-Methyl-1-{2-[4-(3-{pyrid-2-yl}-ureido)-phenyl]-acetylamino}-butyl)-1H-1,2,4-triazol-1-yl]-propionic acid;

4-[4-(3-Methyl-1-{2-[4-(3-{3-methoxypyrid-2-yl}-ureido)-phenyl]-acetylamino}-butyl)-1H-1,2,4-triazol-1-yl]-butyric acid;

2-[4-(3-Methyl-1-{2-[3-methyl-4-(3-o-tolyl-ureido)-phenyl]-acetylamino}-butyl)-1H-1,2,4-triazol-1-yl]-acetic acid;

3-[4-(3-Methyl-1-{2-[3-fluoro-4-(3-o-tolyl-ureido)-phenyl]-acetylamino}-butyl)-1H-1,2,4-triazol-1-yl]-acid;

3-[4-(3-Methyl-1-{2-[3-methoxy-4-(3-{pyrid-2-yl}-ureido)-phenyl]-acetylamino}-butyl)-1H-1,2,4-triazol-1-yl]-propionic acid;

4-[4-(3-Methyl-1-{2-[3-fluoro-4-(3-{3-methoxypyrid-2-yl}-ureido)-phenyl]-acetylamino}-butyl)-1H-1,2,4-triazol-1-yl]-butyric acid;

3-[4-(3-Methyl-1-{2-[3-methoxy-4-(3-{3-methylpyrid-2-yl}-ureido)-phenyl]-acetylamino}-butyl)-1H-1,2,4-triazol-1-yl]-propionic acid;

3-[4-(3-Methyl-1-{2-[3-cyclopentyl-4-(3-{3-methylpyrid-2-yl}-ureido)-phenyl]-acetylamino}-butyl)-1H-1,2,4-triazol-1-yl]-propionic acid;

3-[4-(3-Methyl-1-{2-[3-methoxy-4-(3-{3-cyclopentylpyrid-2-yl}-ureido)-phenyl]-acetylamino}-butyl)-1H-1,2,4-triazol-1-yl]-propionic acid;

3-[4-(3-Methyl-1-{2-[3-trifluoromethyl-4-(3-{3-cyclopentylpyrid-2-yl}-ureido)-phenyl]-acetylamino}-butyl)-1H-1,2,4-triazol-1-yl]-propionic acid.

Compounds which include the moiety of partial Formula (1.1.12):

3-[4-(3-Methyl-1-{2-[4-(3-o-tolyl-ureido)-phenyl]-acetylamino}-butyl)-1H-1,2,3,4-tetrazol-1-yl]-propionic acid;

3-[4-(3-Methyl-1-{2-[4-(3-{2-methoxyphenyl}-ureido)-phenyl]-acetylamino}-butyl)-1H-1,2,3,4-tetrazol-1-yl]-propionic acid;

3-[4-(3-Methyl-1-{2-[4-(3-{pyrid-2-yl}-ureido)-phenyl]-acetylamino}-butyl)-1H-1,2,3,4-tetrazol-1-yl]-propionic acid;

4-[4-(3-Methyl-1-{2-[4-(3-{3-methoxypyrid-2-yl}-ureido)-phenyl]-acetylamino}-butyl)-1H-1,2,3,4-tetrazol-1-yl]-butyric acid;

2-[4-(3-Methyl-1-{2-[3-methyl-4-(3-o-tolyl-ureido)-phenyl]-acetylamino}-butyl)-1H-1,2,3,4-tetrazol-1-yl]-acetic acid;

3-[4-(3-Methyl-1-{2-[3-fluoro-4-(3-o-tolyl-ureido)-phenyl]-acetylamino}-butyl)-1H-1,2,3,4-tetrazol-1-yl]-acid;

3-[4-(3-Methyl-1-{2-[3-methoxy-4-(3-{pyrid-2-yl}-ureido)-phenyl]-acetylamino}-butyl)-1H-1,2,3,4-tetrazol-1-yl]-propionic acid;

4-[4-(3-Methyl-1-{2-[3-fluoro-4-(3-{3-methoxypyrid-2-yl}-ureido)-phenyl]-acetylamino}-butyl)-1H-1,2,3,4-tetrazol-1-yl]-butyric acid;

3-[4-(3-Methyl-1-{2-[3-methoxy-4-(3-{3-methylpyrid-2-yl}-ureido)-phenyl]-acetylamino}-butyl)-1H-1,2,3,4-tetrazol-1-yl]-propionic acid;

3-[4-(3-Methyl-1-{2-[3-cyclopentyl-4-(3-{3-methylpyrid-2-yl}-ureido)-phenyl]-acetylamino}-butyl)-1H-1,2,3,4-tetrazol-1-yl]-propionic acid;

3-[4-(3-Methyl-1-{2-[3-methoxy-4-(3-{3-cyclopentylpyrid-2-yl}-ureido)-phenyl]-acetylamino}-butyl)-1H-1,2,3,4-tetrazol-1-yl]-propionic acid;

3-[4-(3-Methyl-1-{2-[3-trifluoromethyl-4-(3-{3-cyclopentylpyrid-2-yl}-ureido)-phenyl]-acetylamino}-butyl)-1H-1,2,3,4-tetrazol-1-yl]-propionic acid.

Compounds which include the moiety of partial Formula (1.1.13):

3-(3-iso-butyl-2-oxo-4-{[4-(3-o-tolyl-ureido)-phenyl]-acetyl}-piperazin-1-yl)-propionic acid;

3-(3-iso-butyl-2-oxo-4-{[4-(3-{2-methoxyphenyl}-ureido)-phenyl]-acetyl}-piperazin-1-yl)-propionic acid;

3-(3-iso-butyl-2-oxo-4-{[4-(3-{pyrid-2-yl}-ureido)-phenyl]-acetyl}-piperazin-1-yl)-propionic acid;

4-(3-iso-butyl-2-oxo-4-{[4-(3-{3-methoxypyrid-2-yl}-ureido)-phenyl]-acetyl}piperazin-1-yl)-butyric acid;

2-(3-iso-butyl-2-oxo-4-{[3-methyl-4-(3-o-tolyl-ureido)-phenyl]-acetyl}-piperazin-1-yl)-acetic acid;

3-(3-iso-butyl-2-oxo-4-{[3-fluoro-4-(3-o-tolyl-ureido)-phenyl]-acetyl}-piperazin-1-yl)-propionic acid;

3-(3-iso-butyl-2-oxo-4-{[3-methoxy-4-(3-{pyrid-2-yl}-ureido)-phenyl]-acetyl}-piperazin-1-yl)-propionic acid;

4-(3-iso-butyl-2-oxo-4-{[3-fluoro-4-(3-{3-methoxypyrid-2-yl}-ureido)-phenyl]-acetyl}-piperazin-1-yl)-butyric acid;

3-(3-iso-butyl-2-oxo-4-{[3-methoxy-4-(3-{3-methylpyrid-2-yl}-ureido)-phenyl]-acetyl}-piperazin-1-yl)-propionic acid;

3-(3-iso-butyl-2-oxo-4-{[3-cyclopentyl-4-(3-{3-methylpyrid-2-yl}-ureido)-phenyl]-acetyl}-piperazin-1-yl)-propionic acid;

3-(3-iso-butyl-2-oxo-4-{[3-methoxy-4-(3-{3-cyclopentylpyrid-2-yl}-ureido)-phenyl]-acetylamino}-piperazin-1-yl)-propionic acid;

3-(3-iso-butyl-2-oxo-4-{[3-trifluoromethyl-4-(3-{3-cyclopentylpyrid-2-yl}-ureido)-phenyl]-acetyl}-piperazin-1-yl)-propionic acid.

Compounds which include the moiety of partial Formula (1.1.14):

3-(3-iso-butyl-6-oxo-4-{[4-(3-o-tolyl-ureido)-phenyl]-acetyl}-piperazin-1-yl)-propionic acid;

3-(3-iso-butyl-6-oxo-4-{[4-(3-{2-methoxyphenyl}-ureido)-phenyl]-acetyl}-piperazin-1-yl)-propionic acid;

3-(3-iso-butyl-6-oxo-4-{[4-(3-{pyrid-2-yl}-ureido)-phenyl]-acetyl}-piperazin-1-yl)-propionic acid;

4-(3-iso-butyl-6-oxo-4-{[4-(3-{3-methoxypyrid-2-yl}-ureido)-phenyl]-acetyl}-piperazin-1-yl)-butyric acid;

2-(3-iso-butyl-6-oxo-4-{[3-methyl-4-(3-o-tolyl-ureido)-phenyl]-acetyl}-piperazin-1-yl)-acetic acid;

3-(3-iso-butyl-6-oxo-4-{[3-fluoro-4-(3-o-tolyl-ureido)-phenyl]-acetyl}-piperazin-1-yl)-propionic acid;

3-(3-iso-butyl-6-oxo-4-{[3-methoxy-4-(3-{pyrid-2-yl}-ureido)-phenyl]-acetyl}-piperazin-1-yl)-propionic acid;

4-(3-iso-butyl-6-oxo-4-{[3-fluoro-4-(3-{3-methoxypyrid-2yl}-ureido)-phenyl]-acetyl}-piperazin-1-yl)-butyric acid;

3-(3-iso-butyl-6-oxo-4-{[3-methoxy-4-(3-{3-methylpyrid-2-yl}-ureido)-phenyl]-acetyl}-piperazin-1-yl)-propionic acid;

3-(3-iso-butyl-6-oxo-4-{[3-cyclopentyl-4-(3-{3-methylpyrid-2-yl}-ureido)-phenyl]-acetyl}-piperazin-1-yl)-propionic acid;

3-(3-iso-butyl-6-oxo-4-{[3-methoxy-4-(3-{3-cyclopentylpyrid-2-yl}-ureido)-phenyl]-acetylamino}-piperazin-1-yl)-propionic acid;

3-(3-iso-butyl-6-oxo-4-{[3-trifluoromethyl-4-(3-{3-cyclopentylpyrid-2-yl}-ureido)-phenyl]-acetyl}-piperazin-1-yl)-propionic acid.

Compounds which include the moiety of partial Formula (1.3.0):

3-[2-(1-{[4-(3-o-Tolyl-ureido)-phenyl]-acetyl}-pyrrolidin-2-yl)-thiazol-5-yl]-propionic acid;

3-[2-(5-Methyl-1-{[4-(3-o-tolyl-ureido)-phenyl]-acetyl}-pyrrolidin-2-yl)-thiazol-5-yl]-propionic acid;

3-[2-(5,5-Dimethyl-1-{[4-(3-o-tolyl-ureido)-phenyl]-acetyl}-pyrrolidin-2-yl)-thiazol-5-yl]-propionic acid;

3-[2-(3-Methyl-1-{[4-(3-o-tolyl-ureido)-phenyl]-acetyl}-pyrrolidin-2-yl)-thiazol-5-yl]-propionic acid;

3-[2-(3,3-Dimethyl-1-{[4-(3-o-tolyl-ureido)-phenyl]-acetyl}-pyrrolidin-2-yl)-thiazol-5-yl]-propionic acid;

3-[2-(4-Methyl-1-{[4-(3-o-tolyl-ureido)-phenyl]-acetyl}-pyrrolidin-2-yl)-thiazol-5-yl]-propionic acid;

3-[2-(4-Hydroxy-1-{[4-(3-o-tolyl-ureido)-phenyl]-acetyl}-pyrrolidin-2-yl)-thiazol-5-yl]-propionic acid;

3-[2-(4-Hydroxy-4-methyl-1-{[4-(3-o-tolyl-ureido)-phenyl]-acetyl}-pyrrolidin-2-yl)-thiazol-5-yl]-propionic acid;

3-[2-(1-{[4-(3-o-Tolyl-ureido)-phenyl]-acetyl}-azepan-2-yl)-thiazol-5-yl]-propionic acid;

3-[2-(4-Oxo-1-{[4-(3-o-tolyl-ureido)-phenyl]-acetyl}-pyrrolidin-2-yl)-thiazol-5-yl]-propionic acid;

3-[2-(4-Amino-1-{[4-(3-o-tolyl-ureido)-phenyl]-acetyl}-pyrrolidin-2-yl)-thiazol-5-yl]-propionic acid;

3-[2-(4-Methylamino-1-{[4-(3-o-tolyl-ureido)-phenyl]-acetyl}-pyrrolidin-2-yl)-thiazol-5-yl]-propionic acid;

3-[2-(4-(Ethyl-methyl-amino)-1-{[4-(3-o-tolyl-ureido)-phenyl]-acetyl}-pyrrolidin-2-yl)-thiazol-5-yl]-propionic acid;

3-[2-(2-Methyl-1-{[4-(3-o-tolyl-ureido)-phenyl]-acetyl}-pyrrolidin-2-yl)-thiazol-5-yl]-propionic acid;

3-[2-(3-{[4-(3-o-Tolyl-ureido)-phenyl]-acetyl}-oxazolidin-4-yl)-thiazol-5-yl]-propionic acid;

3-(3'-{[4-(3-o-Tolyl-ureido)-phenyl]-acetyl}-2',3',4',5'-tetrahydro-[2,4']bithiazolyl-5yl)-propionic acid;

3-[2-(1-{[4-(3-o-Tolyl-ureido)-phenyl]-acetyl}-1,2,3,6-tetrahydro-pyridin-2-yl)-thiazol-5-yl]-propionic acid;

3-[2-(1-{[4-(3-o-Tolyl-ureido)-phenyl]-acetyl}-piperidin-2-yl)-thiazol-5yl]-propionic acid;

3-[2-(2-{[4-(3-o-Tolyl-ureido)-phenyl]-acetyl}-1 2,3,4-tetrahydro-isoquinolin-3-yl)-thiazol-5-yl]-propionic acid;

3-[2-(1-{[4-(3-o-Tolyl-ureido)-phenyl]-acetyl}-azetidin-2-yl)-thiazol-5-yl]-propionic acid;

3-[2-(1-{[4-(3-o-Tolyl-ureido)-phenyl]-acetyl}-azetidin-2-yl)-oxazol-5-yl]-propionic acid;

3-[2-(1-{[4-(3-o-Tolyl-ureido)-phenyl]-acetyl}-pyrrolidin-2-yl)oxazol-5-yl]-propionic acid;

3-[2-(1-{[4-(3-o-Tolyl-ureido)-phenyl]-acetyl}-azepan-2-yl)-oxazol-5-yl]-propionic acid;

3-[2-(5-Methyl-1-{[4-(3-o-tolyl-ureido)-phenyl]-acetyl}-pyrrolidin-2-yl)oxazol-5-yl]-propionic acid;

3-[2-(5,5-Dimethyl-1-{[4-(3-o-tolyl-ureido)-phenyl]-acetyl}-pyrrolidin-2-yl)-oxazol-5-yl]-propionic acid;

3-[2-(3-Methyl-1-{[4-(3-o-tolyl-ureido)-phenyl]-acetyl}-pyrrolidin-2-yl)-oxazol-5-yl]-propionic acid;

3-[2-(3,3-Dimethyl-1-{[4-(3-o-totyl-ureido)-phenyl]-acetyl}-pyrrolidin-2-yl)oxazol-5-yl]-propionic acid;

3-[2-(4-Methyl-1-{[4-(3-o-tolyl-ureido)-phenyl]-acetyl}-pyrrolidin-2-yl)oxazol-5-yl]-propionic acid;

3-[2-(4-Hydroxy-1-{[4-(3-o-tolyl-ureido)-phenyl]-acetyl}-pyrrolidin-2-yl)-oxazol-5-yl]-propionic acid;

3-[2-(4-Hydroxy-4-methyl-1-{[4-(3-o-tolyl-ureido)-phenyl]-acetyl}-pyrrolidin-2-yl)-oxazol-5-yl]-propionic acid;

3-[2-(4-Oxo-1-{[4-(3-o-tolyl-ureido)-phenyl]-acetyl}-pyrrolidin-2-yl)-oxazol-5-yl]-propionic acid;

3-[2-(4-Amino-1-{[4-(3-o-tolyl-ureido)-phenyl]-acetyl}-pyrrolidin-2-yl)-oxazol-5-yl]-propionic acid;

3-[2-(4-Methylamino-1-{[4-(3-o-tolyl-ureido)-phenyl]-acetyl}-pyrrolidin-2-yl)-oxazol-5-yl]-propionic acid;

3-[2-(4-(Ethyl-methyl-amino)-1-{[4-(3-o-tolyl-ureido)-phenyl]-acetyl}-pyrrolidin-2-yl)-oxazol-5-yl]-propionic acid;

3-[2-(2-Methyl-1-{[4-(3-o-tolyl-ureido)-phenyl]-acetyl}-pyrrolidin-2-yl)-oxazol-5-yl]-propionic acid;

3-[2-(3-{[4-(3-o-Tolyl-ureido)-phenyl]-acetyl}-oxazolidin-4-yl)oxazol-5-yl]-propionic acid;

3-[2-(3-{[4-(3-o-Tolyl-ureido)-phenyl]-acetyl}-thiazolidin-4-yl)-oxazol-5yl]-propionic acid;

3-[2-(1-{[4-(3-o-Tolyl-ureido)-phenyl]-acetyl}-1,2,3,6-tetrahydro-pyridin-2-yl)-oxazol-5-yl]-propionic acid;

3-[2-(1-{[4-(3-o-Tolyl-ureido)-phenyl]-acetyl}-piperidin-2-yl)-oxazol-5-yl]-propionic acid;

3-[2-(2-{[4-(3-o-Tolyl-ureido)-phenyl]-acetyl}-1,2,3,4-tetrahydro-isoquinolin-3-yl)-oxazol-5-yl]-propionic acid;

3-[3-(1-{[4-(3-o-Tolyl-ureido)-phenyl]-acetyl}-pyrrolidin-2-yl)-isoxazol-5-yl]-propionic acid;

3-[3-(5-Methyl-1-{[4-(3o-tolyl-ureido)-phenyl]-acetyl}-pyrrolidin-2-yl)-isoxazol-5yl]-propionic acid;

3-[3-(5,5-Dimethyl-1-{[4-(3-o-tolyl-ureido)-phenyl]-acetyl}-pyrrolidin-2-yl)-isoxazol-5-yl]-propionic acid;

3-[3-(1-{[4-(3-o-Tolyl-ureido)-phenyl]-acetyl}-azepan-2-yl)-isoxazol-5-yl]-propionic acid;

3-[3-(3-Methyl-1-{[4-(3-o-tolyl-ureido)-phenyl]-acetyl}-pyrrolidin-2-yl)-isoxazol-5-yl]-propionic acid;

3-[3-(3,3-Dimethyl-1-{[4-(3-o-tolyl-ureido)-phenyl]-acetyl}-pyrrolidin-2-yl)-isoxazol-5-yl]-propionic acid;

3-[3-(4-Methyl-1-{[4-(3-o-tolyl-ureido)-phenyl]-acetyl}-pyrrolidin-2-yl)-isoxazol-5-yl]-propionic acid;

3-[3-(4-Hydroxy-1-{[4-(3-o-tolyl-ureido)-phenyl]-acetyl}-pyrrolidin-2-yl)-isoxazol-5-yl]-propionic acid;

3-[3-(4-Hydroxy-4-methyl-1-{[4-(3-o-tolyl-ureido)-phenyl]-acetyl}-isoxazol-2-yl)-thiazol-5-yl]-propionic acid;

3-[3-(4-Oxo-1-{[4-(3-o-tolyl-ureido)-phenyl]-acetyl}-pyrrolidin-2-yl)-isoxazol-5-yl]-propionic acid;

3-[3-(4-Amino-1-{[4-(3-o-tolyl-ureido)-phenyl]-acetyl}-pyrrolidin-2-yl)-isoxazol-5-yl]-propionic acid;

3-[3-(4-Methylamino-1-{[4-(3-o-tolyl-ureido)-phenyl]-acetyl}-pyrrolidin-2-yl)-isoxazol-5-yl]-propionic acid;

3-[3-(4-(Ethyl-methyl-amino)-1-{[4-(3o-tolyl-ureido)-phenyl]-acetyl}-pyrrolidin-2-yl)-isoxazol-5-yl]-propionic acid;

3-[3-(2-Methyl-1-{[4-(3-o-tolyl-ureido)-phenyl]-acetyl}-pyrrolidin-2-yl)-isoxazol-5-yl]-propionic acid;

3-[3-(3-{[4-(3-o-Tolyl-ureido)-phenyl]-acetyl}-oxazolidin-4-yl)-isoxazol-5-yl]-propionic acid;

3-[3-(3-{[4-(3-o-Tolyl-ureido)-phenyl]-acetyl}-thiazolidin-4-yl)-isoxazol-5-yl]-propionic acid;

3-[3-(1-{[4-(3-o-Tolyl-ureido)-phenyl]-acetyl}-1,2,3,6-tetrahydro-pyridin-2-yl)-isoxazol-5-yl]-propionic acid;

3-[3-(1-{[4-(3-o-Tolyl-ureido)-phenyl]-acetyl}-piperidin-2-yl)-isoxazol-5-yl]-propionic acid;

3-[3-(2-{[4-(3-o-Tolyl-ureido)-phenyl]-acetyl}-1,2,3,4-tetrahydro-isoquinolin-3-yl)-isoxazol-5-yl]-propionic acid; and 3-[3-(1-{[4-(3-o-Tolyl-ureido)-phenyl]-acetyl}-azetidin-2-yl)-isoxazol-5-yl]-propionic acid.

The above-described compounds of the present invention may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures well known in the art. Such well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such agents as ($C_1$–$C_4$)alkyl halides, e.g., methyl, ethyl, iso-propyl and tert-butyl chlorides, bromides and iodides; di($C_1$–$C_4$)alkyl sulfate, e.g., dimethyl, diethyl and diamyl sulfates; ($C_{10}$–$C_{18}$)alkyl halides, e.g., decyl, dodecyl, lauryl, myristyl and and stearyl chlorides, bromides and iodides; and aryl-($C_1$–$C_4$)alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described inhibitiory compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipient, adjuvants and vehicles. Pharmaceutically acceptable carriers that may be used in the pharmaceutical compositions of this invention include but are not limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the diluents, excipient, adjuvants and vehicles used in the pharmaceutical compositions of the present invention comprise members selected from the groups consisting essentially of the following: acidifying and alkalizing agents added to obtain a desired or predetermined pH comprise acidifying agents, e.g., acetic acid, glacial acetic acid, malic acid, and propionic acid, and alkalizing agents, e.g., edetol, potassium carbonate, potassium hydroxide, sodium borate, sodium carbonate, and sodium hydroxide; aerosol propellants required where the pharmaceutical composition is to be delivered as an aerosol under significant pressure, e.g., acceptable halogenated hydrocarbons; nitrogen; or a volatile hydrocarbon such as butane, propane, isobutane or mixtures thereof; antimicrobial agents including antibacterial, antifungal and antiprotozoal agents added where the pharmaceutical composition is topically applied, e.g, antimicrobial agents such as benzyl alcohol, chlorobutanol, phenylethyl alcohol, phenylmercuric acetate, potassium sorbate, and sorbic acid, and antifungal agents such as benzoic acid, butylparaben, ethylparaben, methylparaben, propylparaben, and sodium benzoate; antimicrobial preservatives added to the pharmaceutical compositions in order to protect them against the growth of potentially harmful microorganisms, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol; antioxidants added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols; buffering agents used to maintain a desired pH of a composition once established, e.g., calcium acetate, potassium metaphosphate, potassium phosphate monobasic, and tartaric acid; and chelating agents used to help maintain the ionic strength of the pharmaceutical composition and bind to and effectively remove destructive compounds and metals, e.g., edetate dipotassium, edetate disodium, and edetic acid.

Dermatologically active agents are added to the pharmaceutical compositions of the present invention to be applied topically, e.g., wound healing agents such as peptide derivatives, yeast, panthenol, hexylresorcinol, phenol, tetracycline hydrochloride, lamin and kinetin, glucocorticosteroids for treating inflammation, e.g., hydrocortisone, dexamethasone, betamethasone, triamcinolone, fluocinolone and methylprednisolone, retinoids for treating acne, psoriasis, cutaneous aging, and skin cancer, e.g., retinol, tretinoin, isotretinoin, etretinate, acitretin, and arotinoid, immunosuppressive agents for treating inflammation, e.g., dapsone and sulfasalazine; mild antibacterial agents, e.g., resorcinol, salicylic acid, benzoyl peroxide, erythromycin-benzoyl peroxide, erythromycin, clindamycin, and mupirocin, antifungal agents, e.g., griseofulvin, azoles such as miconazole, econazole, itraconazole, fluconazole, and ketoconazole, and allylamines such as naftifine and terfinafine, antiviral agents, e.g., acyclovir, famciclovir, and valacyclovir, antihistamines, e.g., diphenhydramine, terfenadine, astemizole, loratadine, cetirizine, acrivastine, and temelastine, topical anesthetics, e.g., benzocaine, lidocaine, dibucaine, and pramoxine hydrochloride, topical analgesics, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Further examples of diluents, excipient, adjuvants and vehicles used in the pharmaceutical compositions of the present invention comprise members selected from the groups consisting essentially of the following: dispersing and suspending agents, e.g., poligeenan, povidone, and silicon dioxide; emollients, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., a-dodecyl-ω-hydroxy-poly(oxy-1,2-ethanediyl) or polyethylene glycol monododecyl ether.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HClX or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective for preventing, inhibiting, suppressing or reducing cell adhesion and consequent or associated pathogenic processes subsequently mediated by VLA-4 will depend on a variety of factors, such as the nature of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of Formula (1.0.0) will be between about 1.0 $\mu$g and about 10.0 mg/kg body weight per day, preferably between about 5.0 $\mu$g and about 5.0 mg/kg body weight per day, more preferably between about 10.0 $\mu$g and about 1.0 mg/kg of body weight per day, and most preferably between about 20.0 $\mu$g and about 0.5 mg/kg of body weight per day of the active ingredient.

Where the dosage form is topically administered to the bronchia and lungs, e.g., by means of a powder inhaler or nebulizer, suitable dosage levels of the compounds of Formula (1.0.0) will be between about 0.1 $\mu$g and about 1.0 mg/kg body weight per day, preferably between about 0.5 $\mu$g and about 0.5 mg/kg body weight per day, more preferably between about 1.0 $\mu$g and about 0.1 mg/kg of body weight per day, and most preferably between about 2.0 $\mu$g and about 0.05 mg/kg of body weight per day of the active ingredient.

Using representative body weights of 10 kg and 100 kg in order to illustrate the range of daily topical dosages which might be used as described above, suitable dosage levels of the compounds of Formula (1.0.0) will be between about 1.0–10.0 $\mu$g and 10.0–100.0 mg per day, preferably between about 5.0–50.0 $\mu$g and 5.0–50.0 mg per day, more preferably between about 10.0–100.0 $\mu$g and 1.0–10.0 mg per day, and most perferably between about 20.0–200.0 $\mu$g and about 0.5–5.0 mg per day of the active ingredient comprising a compound of Formula (1.0.0). These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy.

Numerous other factors must also be considered in deciding upon the number of doses per day and the amount of active ingredient per dose which will be administered. Not the least important of such other factors is the individual respsonse of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered each day, each dose containing from about 50.0 $\mu$g to about 10.0 mg of active ingredient.

Included within the scope of the present invention are embodiments comprising compositions which contain, in addition to a compound of the present invention as active ingredient, additional therapeutic agent active ingredients selected from the group consisting essentially of anti-inflammatory corticosteroids; bronchodilators; antiasthmatics; non-steroidal anti-inflammatories; immunosuppressants; immunostimulants; antimetabolites; antipsoriatics and antidiabetics. Specific compounds within each of these classes may be selected from those listed under the appropriate headings in *Comprehensive Medicinal Chemistry,* Pergamon Press, Oxford, England, pp. 970–986 (1990); and *Goodman and Gilman's The Pharmacological Basis of Therapeutics,* 9th ed., Hardman, J. G. and Limbird, L. E., eds., McGraw-Hill, 1996, the disclosure of which are incorporated herein by reference in their entireties. Especially preferred active ingredients to be included for use in combination with the compounds of Formula (1.0.0) are anti-inflammatory compounds such as theophylline, sulfasalazine and aminosalicylates; immunosuppressants such as cyclosporin, FK-506, and rapamycin; antimetabolites such as cyclophosphamide and methotrexate; and immunomodulators such as the interferons.

Still further embodiments of the present invention relate to a method of treating or preventing an inflammatory, autoimmune or respiratory disease by inhibiting cell adhesion and consequent or associated pathogenic processes subsequently mediated by VLA-4. As already mentioned,. VLA-4-associated cell adhesion plays a central role in a variety of inflammatory, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

The above-described methods of treatment of the present invention may employ the compounds of Formula (1.0.0) in the form of monotherapy, but said methods may also be used in the form of multiple therapy in which one or more compounds of Formula (1.0.0) are coadministered in combination with a known anti-inflammatory, immunomodulating, immunostimulating or immunosuppressive agent. The terms "coadministered" or "coadministration" as used herein are intended to mean therapeutic utilization of one or more compounds of Formula (1.0.0) in combination with one or more additional therapeutic agents, including but not limited to, administration of the combination of therapeutic active agents in a single dosage form or in multiple dosage forms representing the same or different routes of administration, said multiple dosage forms being administered at substantially the same time or at different times.

Subsequent to synthesis of any of the above-recited preferred species of the present invention or any other compounds falling within the scope of the present invention, the biological activities relating to the VLA-4 specificities of said compounds may be determined using one or more of the numerous in vitro and in vivo assays which have been described heretofore in the technical literature pertinent to the art. For example, some of the now very-well established assay methods and models concern measurement of VLA-4 activity by determining the concentration of a test candidate inhibitor required to block the binding of VLA-4-expressing cells to fibronectin- or CS-1 coated plates. In this assay microtiter wells are coated with either fibronectin (containing the CS-1 sequence), CS-1 peptide or soluble VCAM-1. Once the wells are coated, varying concentrations of the test compound are then added together with appropriately labelled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound. However, the assay just described is less preferred than other assays mentioned further below in determining the VLA-4 activity of the compounds of Formula (1.0.0).

VLA-4-expressing cells that may be utilized in this assay include Ramos cells, Jurkat cells, A375 melanoma cells, as well as human peripheral blood lymphocytes (PBL). The cells used in this assay may be fluorescently or radioactively labelled.

In order to assess the VLA-4 inhibitory specificity of test compounds, assays for other major groups of integrins, i.e., $\beta_2$ and $\beta_3$, as well as other $\beta_1$ integrins, such as VLA-5, VLA-6 and $\alpha_4\beta_7$ may be performed. These assays may be similar to the adhesion inhibition and direct binding assays described above, substituting the appropriate integrin-expressing cell and corresponding ligand. For example, polymorphonuclear cells (PMNs) express $\beta_2$ integrins on their surface and bind to ICAM; while $\beta_3$ integrins are involved in platelet aggregation and inhibition may be measured in a standard platelet aggregation assay. VLA-5 binds specifically to Arg-Gly-Asp sequences, while VLA-6 binds to laminin. Further, $\alpha_4\beta_7$ is a recently discovered homologue of VLA-4, which also binds fibronectin and VCAM as well as MAdCAM-1. Specificity with respect to $\alpha_4\beta_7$ is determined in a binding assay that utilizes CS-1, VCAM or MAdCAM-1 and a cell line that expresses $\alpha_4\beta_7$, but not VLA-4, such as RPMI-8866 cells.

Once VLA-4-specific inhibitors are identified, they may be further characterized in in vivo assays. One such assay tests the inhibition of allergen induced airway hyperresponsiveness and cell influx, such as described by Henderson et al., "Blockade of CD49d ($\alpha_4$ integrin) on intrapulmonary but not circulating leukocytes inhibits airway inflammation and hyperresponsiveness in a mouse model of asthma", *J. Clin. Invest.*, 100(12), pp. 3083–92 (1997). In this assay, mice are sensitized by ip exposure to an irritant, such as ovalbumin. Following a recovery period, the mice are challenged by aerosol exposure to the allergen. Before aerosol exposure, the mice are given various doses of the VLA-4 inhibitor by intratracheal injection. In vivo inhibition of cell adhesion associated inflammation is assessed by measuring the number of cells and cytokines in the bronchial alveolar lavage fluid. In this manner, one may identify those inhibitors of this invention which are best suited for inhibiting inflammation.

Another in vivo assay that may be employed the primate asthma assay. This assay is performed essentially as described in Turner, C. R., et al., "Characterization of a primate model of asthma using anti-allergy/anti-asthma agents", *Inflammation Research*, 45(5), pp. 239–45 (1996), the disclosure of which is incorporated herein by reference in its entirety. This assay measures inhibition of Ascaris antigen-induced late phase airway responses and airway hyperresponsiveness in allergic primates following administration of anti-allergy/anti-asthma agents.

The compounds of the present invention may be formulated into pharmaceutical compositions that may be administered orally, parenterally, by inhalation (metered dose inhaler, dry powder inhaler or nebulizer), topically, rectally, nasally, intraocularly, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The compounds of Formula (1.0.0) may be prepared in accordance with well-known procedures for carrying out the synthesis of organic compounds which are non-peptidyl or semi-peptidyl in nature. A number of different procedures are available which are fully disclosed in the technical literature and with which the skilled artisan will be familiar. The description which follows of several such synthesis schemes is merely representative and not intended to be in any way limiting. A number abbreviations are used in said description in order to conserve space. Although these abbreviations are also well known to the artisan, they are set out immediately below for clarity and convenience:

| BOP | benzotriazol-1-yloxy-tris (dimethylamino) phosphonium hexafluorophosphate | EDCI | 1-(3-dimethylamino-propyl)-3-ethylcarbodiimide hydrochloride |
|---|---|---|---|
| DAST | diethylaminosulfur trifluoride | HOBT | 1-hydroxybenzotriazole |
| DIEA | diisopropylethyl amine | THF | tetrahydrofuran |
| DMF | Dimethylformamide | | |

A group of preferred A components of the compounds of Formula (1.0.0) have been described above and illustrated by partial formulas (IVb) through (IVu). The most basic of these components is that of Formula (IVc), i.e., 4-(N'-phenylurea)-phenylmethyl. The following schematic synthesis diagram illustrates a generalized preparation process for the compounds of Formulas (1.4.0)–(1.4.20):

Synthesis Scheme I—Step A

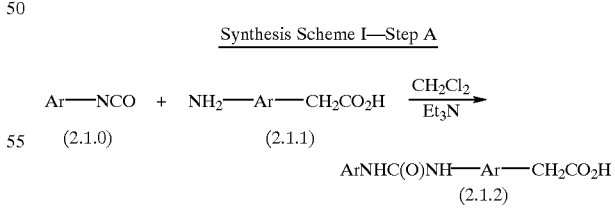

The starting material Ar-NCO is an isocyanate in which "Ar" has the same definition as the A component of Formula (1.0.0) regarding the aryl, heteroaryl and heterocyclyl moieties substituted with 0 to 3 $R^{10}$. Isocyanate starting materials for making component A as represented by partial Formulas (1.4.1) through (1.4.20) are commercially available, e.g., from Aldrich Chemical Company, Milwaukee, Wis. 53233, as follows:

| | | | |
|---|---|---|---|
| phenyl isocyanate | (1.4.1); (1.4.2) | 2-methoxyphenyl isocyanate | (1.4.4) |
| o-tolyl isocyanate | (1.4.3); (1.4.5); (1.4.7); (1.4.16); (1.4.20) | 2-fluorophenyl isocyanate | (1.4.12) |
| 2-chlorophenyl isocyanate | (1.4.13); (1.4.14) | 4-iso-propylphenyl isocyanate | (1.4.15) |

Pyridyl analogues of the above phenyl isocyanates can be used to prepare the corresponding compounds of Formula (1.0.0) where the A component contains a pyridyl group.

One of the above-described isocyantes is reacted with an aryl-, heteroaryl- or heterocyclyl-acetic acid having an amine group at the 4-position. The addition of amines to isocyanates is a well-known reaction which provides substituted ureas in a facile manner. The reaction can be carried out in a solvent such as methylene chloride with triethylamine at slightly elevated temperatures. The reactant used to produce the majority of the A components illustrated as partial Formulas (1.4.1)–(1.4.20) is 4-aminophenylacetic acid, commercially available from the above-mentioned Aldridge Chemical Company.

The disubstituted urea (2.1.2) prepared as in the above-indicated reaction scheme, which forms the reactant eventually resulting in component A of the compounds of Formula (1.0.0), is next reacted with the reactant eventually resulting in component B, one of the partial Formulas (1.1.0)–(1.1.14). For example, the B component reactant may be that of partial Formula (1.7.0) illustrated below in Formula (IIIo-a):

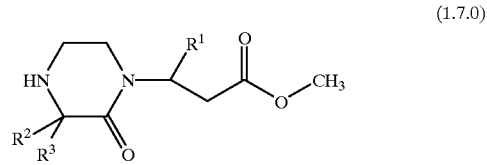

Component B reactants of the type illustrated in Formula (IIIo-a) may be prepared in accordance with procedures well-known in the technical literature of the relevant art. For example, see Bhatt, U.; Mohamed, N.; Just, G.; *Tetrahedron Lett.,* 1997, 38(21), 3679–3682; and Sugihara, H. et al., *J. Med. Chem.,* 1998, 41, 489–502.

The reaction between the component A forming reactant and the component B forming reactant will be recognized by the artisan as one involving the acylation of an amine by a carboxylic acid which can be made to proceed in good yield at room temperature or slightly above by the use of coupling agents such as 1-(3-dimethylaminopropyl)-3-ethylcarbodiimide hydrochloride (EDCI) and 1-hydroxybenzotriazole (HOBT); dicyclohexylcarbodiimide (DCCI); N,N'-carbonyldiimidazole; $POCl_3$; $TiCl_4$; $SO_2ClF$; $Ti(OBu)_4$; $P_2I_4$; $BU_3N$; benzotriazol-1-yl diethyl phosphate; N,N,N',N'-tetramethyl(succinimido)uronium tetrafluoroborate; and preferably di-iso-propylethyl amine (DIEA) and benzotriazol-1-yloxy-tris(dimethylamino) phosphonium hexafluorophosphate (BOP). This reaction may be illustrated in the following schematic synthesis diagram which provides a generalized preparation process for the compounds of Formulas (1.0.0):

Synthesis Scheme I-Step B

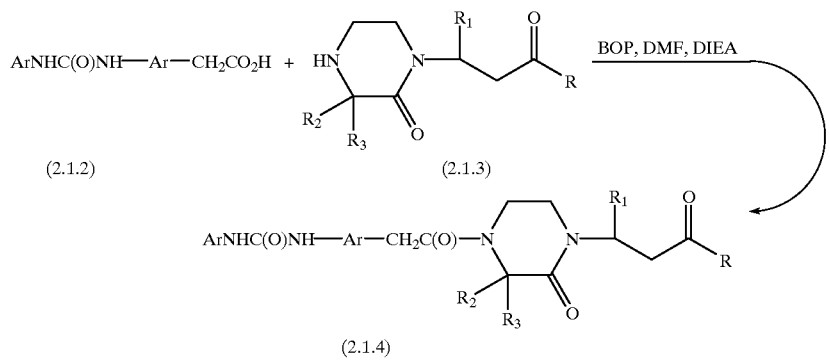

The piperazinyl reactant (2.1.3) for component B is used in the form of the $(C_1-C_4)$alkyl ester of the acid, which serves as a blocking group to prevent reaction of the carboxylic acid group with the secondary amine group forming part of the piperazinyl moiety of other reactants (2.1.3) present in the reaction mixture. The coupling agents promote condensation of reactants (2.1.2) and (2.1.3) to provide intermediate (2.1.4), which is a compound of Formula (1.0.0) where R is defined as $O(C_1-C_6)$alkyl. To prepare the final product of Formula (1.0.0) in the form of the acid, an additional step is required, as is shown in the following reaction scheme:

Synthesis Scheme I-Step C

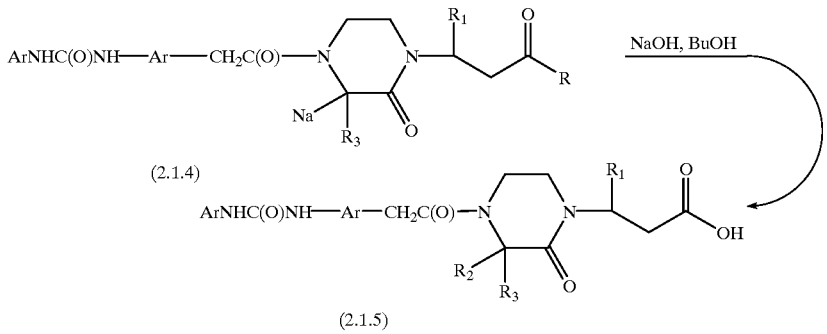

The aqueous hydroxide saponification is carried out in an alcohol solvent, preferably tert-butanol as indicated. Subsequent neutralization is preferably carried out using 1N HCl as the aqueous mineral acid, and the reaction is conveniently carried out at room temperature.

The above-described synthesis is broadly applicable to the compounds of Formula (1.0.0). In order to make said synthesis even more clear, there is set out below Synthesis Scheme 1-α, Steps A through C with reference to a particular compound of the present invention:

Synthesis Scheme I-α

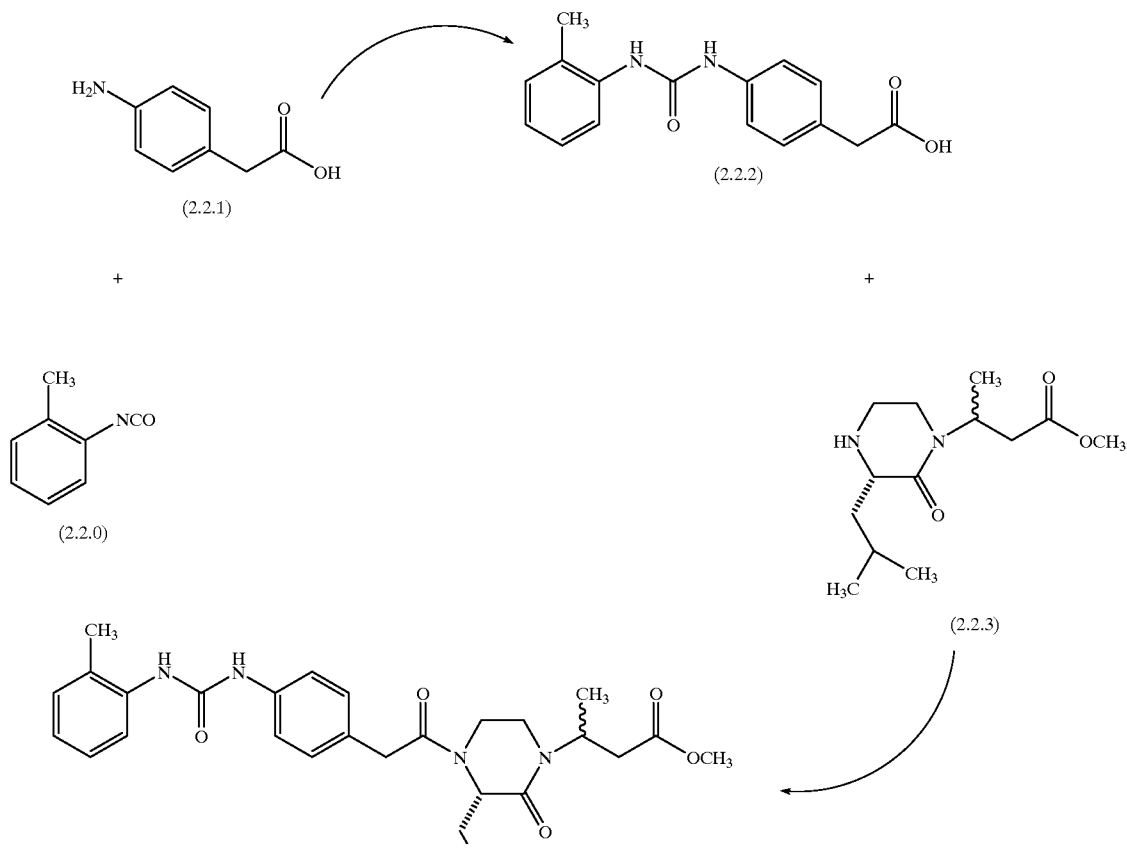

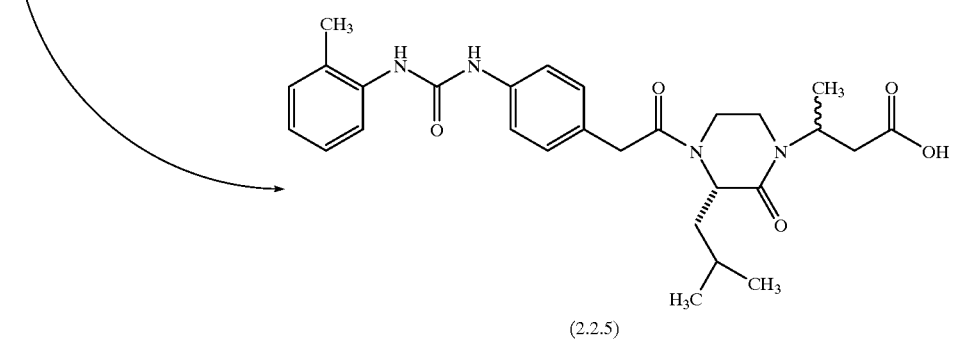

(2.2.5)

Compounds of Formula (1.0.0) in which the B component is a moiety of partial Formula (1.1.4), i.e., an isoxazolyl group, may be prepared by a method in which the final two steps are similar to the final two steps, Steps B and C, of the method illustrated in Synthetic Scheme I. Preparation of the amine reactant which produces component B of partial Formula (1.4.4) is illustrated generally for the compounds of Formula (1.0.0) in the following Synthesis Scheme II—Step A:

Synthesis Scheme II—Step A (2.1.6)

(2.1.7)

In Step A of this synthesis, the starting material is a 1-formyl derivative of a carbamic acid having a protecting group R, and having the desired $R^2$ and $R^3$ substituents, of the formula: $ROC(=O)NHC(R^2)(R^3)CH(=O)$. This aldehyde starting material is reacted with hydroxylamine hydrochloride and sodium acetate in a suitable solvent such as water and methanol to prepare the corresponding oxime in accordance with a well-known procedure involving carbonyl addition and elimination of water in which an optimal pH of about 4 is maintained.

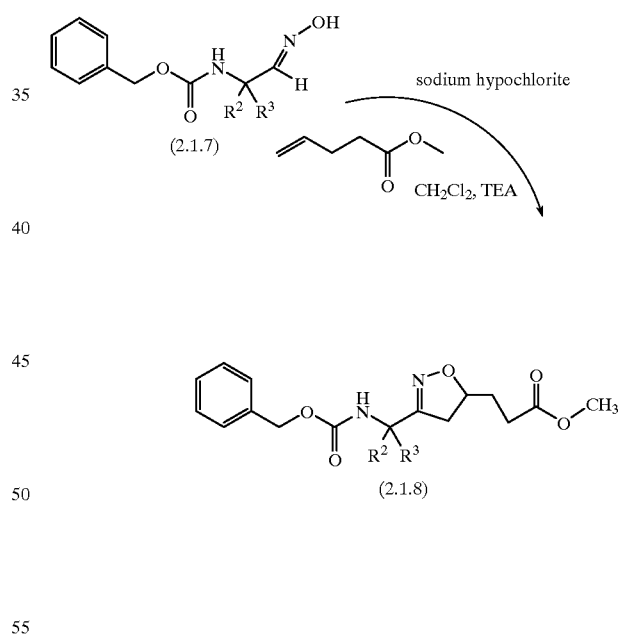

Synthesis Scheme II—Step B (2.1.7)

(2.1.8)

The oxime (hydroxyiminomethyl) intermediate (2.1.7) is converted to the desired isoxazolyl-containing B component of partial Formula (IIIe), intermediate (2.1.8), by oxidizing (2.1.7) to its corresponding nitrile N-oxide with sodium hypochlorite in a suitable solvent such as THF or methylene chloride; and reacting the nitrile N-oxide in situ with an appropriate terminal alkyl alkenoate. This [2+3] cycloaddition reaction is well known in the literature as a method for preparing the isoxazoline ring structure. See, e.g., *Synthesis*, 508–9, 1982.

Synthesis Scheme II-C
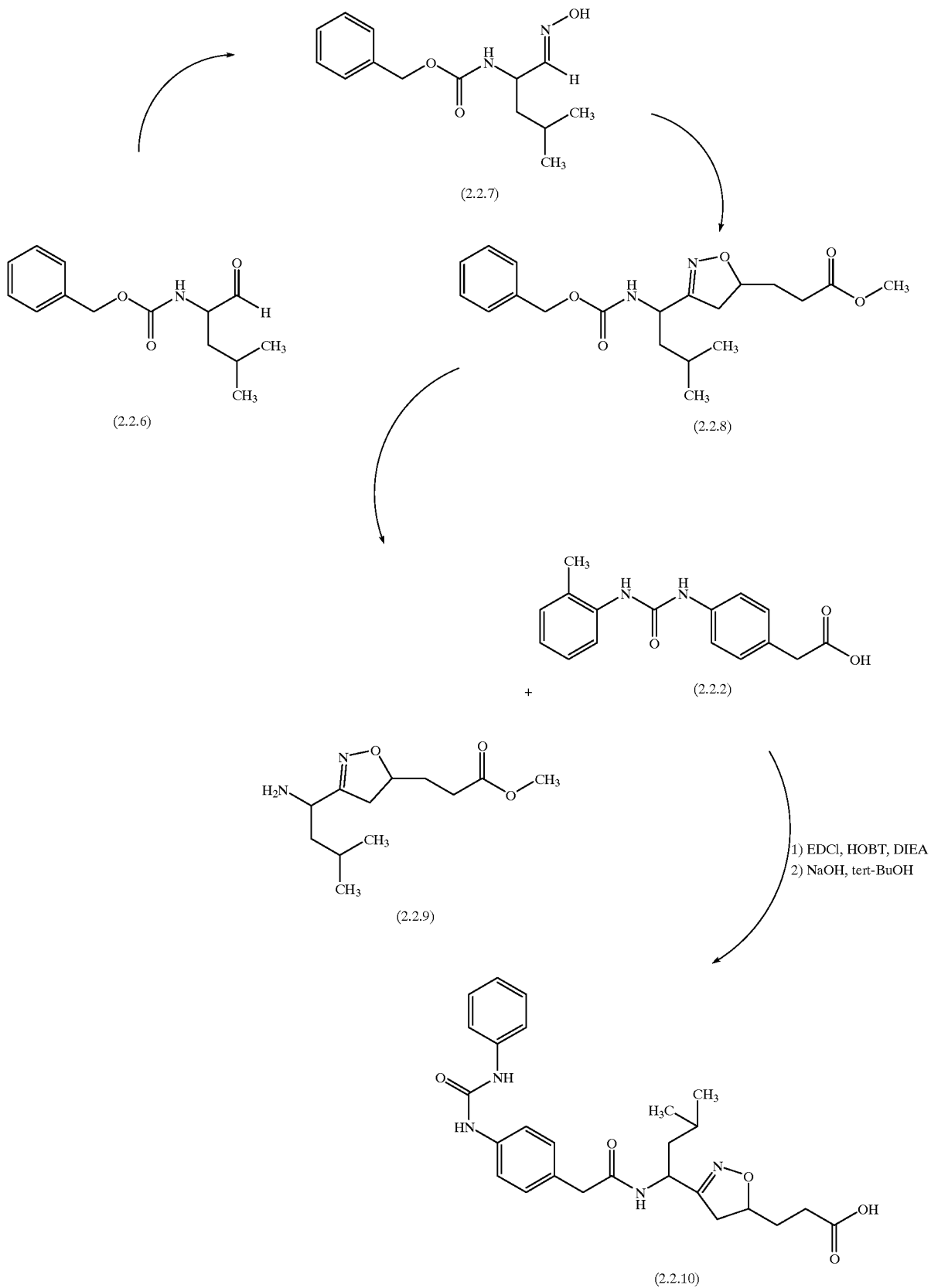

The benzyl carbamate (2.1.8) is converted to the primary amine (2.1.9) by utilizing one of the following reagents using the published literature procedures: H₂/Pd-C (*Ber.*, 65, p. 1192, 1932); HBr, AcOH (*J. Org. Chem.*, 17, p. 1564, 1952); 70% HF, pyridine (*J. Chem. Soc., Chem. Commun.*, p. 451, 1976) or CF₃SO₃H (*J. Chem. Soc., Chem. Commun.*, p. 107, 1974).

The above described synthesis is broadly applicable to the compounds of Formula (1.0.0). In order to make said synthesis even more clear, there is set out below Synthesis Scheme II, Steps A through D with reference to a particular compound of the present invention (where Step D is analogous to Steps B and C in Scheme I):

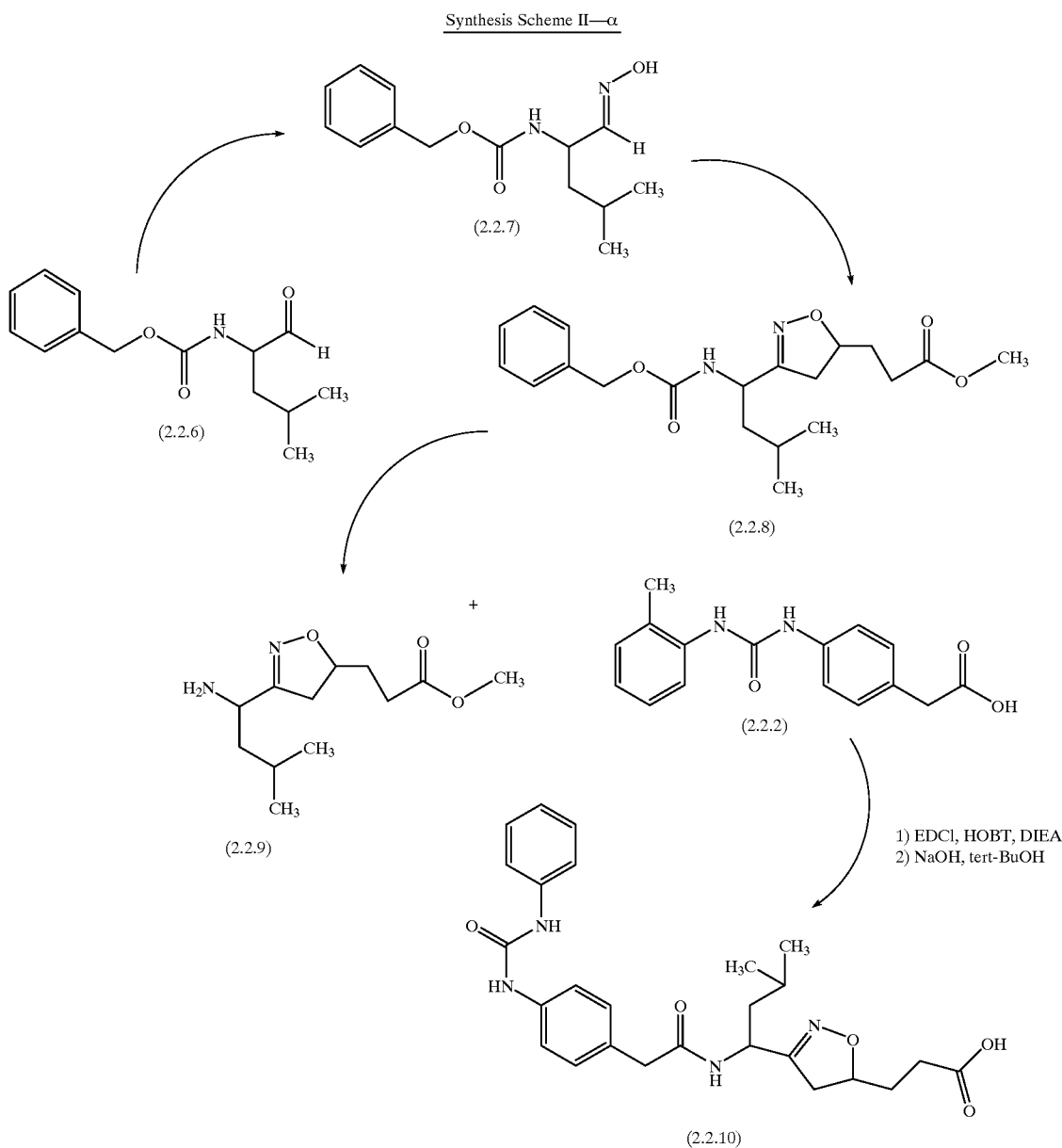

Synthesis Scheme II—α

Compounds of Formula (1.0.0) in which the B component is a moiety of partial Formula (1.1.6), i.e., an isoxazole group, may be prepared by a method in which the final two steps are similar to Steps B and C of the method illustrated in Synthetic Scheme I. Preparation of the amine reactant which produces component B of partial Formula (1.1.6) is illustrated generally for the compounds of Formula (1.0.0) in the following synthesis scheme:

Synthesis Scheme III—Step A

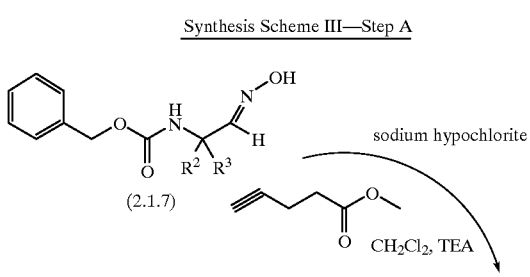

(2.1.7)

sodium hypochlorite

CH₂Cl₂, TEA

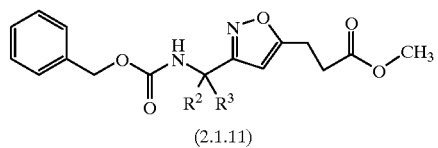

(2.1.11)

The oxime (hydroxyiminomethyl) intermediate (2.1.7) is converted to the desired isoxazole-containing B component of partial Formula (1.1.6), intermediate (2.1.11), by oxidizing (2.1.7) to its corresponding nitrile N-oxide with sodium hypochlorite in a suitable solvent such as THF or methylene chloride; and reacting the nitrile N-oxide in situ with an appropriate terminal alkyl alkynoate. This [2+3] cycloaddition reaction is well known in the literature as a method for preparing the isoxazole ring structure. See, e.g., *Synthesis*, 508–9, 1982.

Synthesis Scheme III - Step B

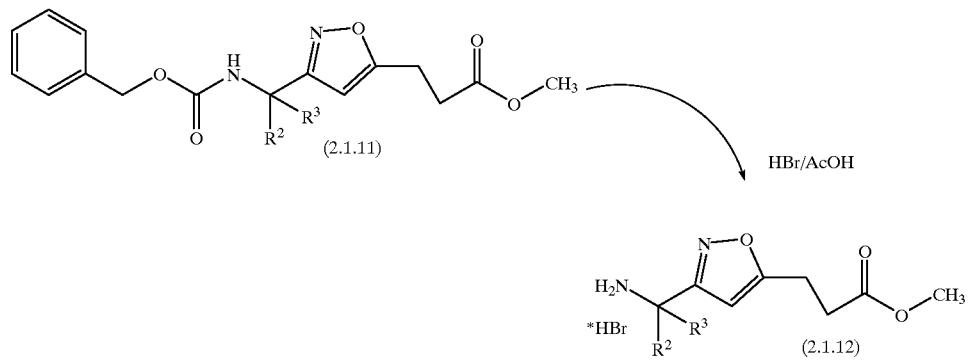

HBr/AcOH

The benzyl carbamate (2.1.11) is converted to the primary amine (2.1.12) by utilizing one of the following reagents using the published literature procedures: $H_2$/Pd-C (*Ber.*, 65, p. 1192, 1932); HBr, AcOH (*J. Org. Chem.*, 17, p. 1564, 1952); 70% HF, pyridine (*J. Chem. Soc., Chem. Commun.*, p. 451, 1976) or $CF_3SO_3H$ (*J. Chem. Soc., Chem. Commun.*, p. 107, 1974).

The above described synthesis is broadly applicable to the compounds of Formula (1.0.0). In order to make said synthesis even more clear, there is set out below Synthesis Scheme III, Steps A through C with reference to a particular compound of the present invention (where Step C is analogous to Steps B and C in Scheme I):

Synthesis Scheme III-α

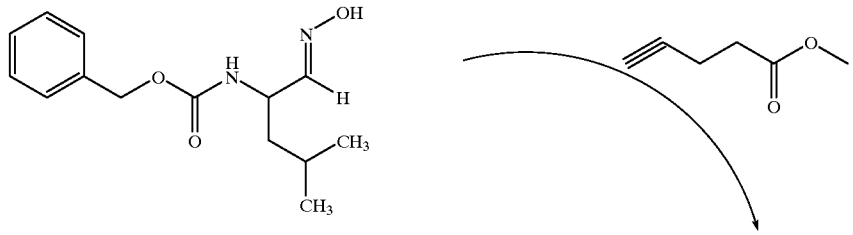

-continued
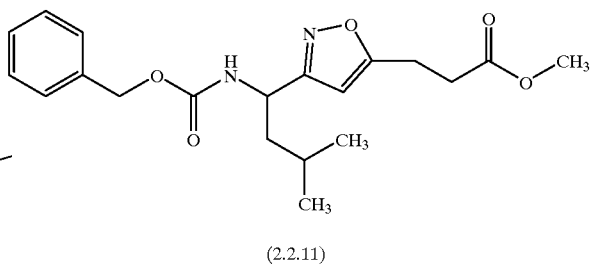
(2.2.11)
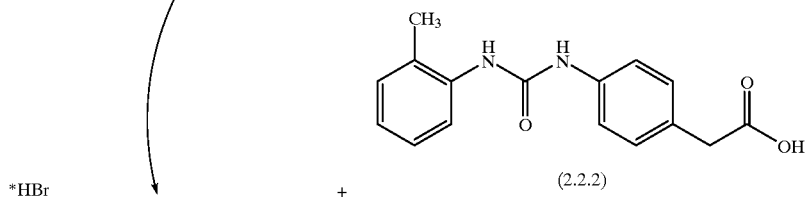
(2.2.2)
*HBr +
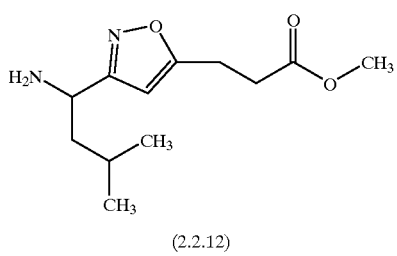
(2.2.12)
1) EDCl, HOBT, DIEA
2) NaOH, tert-BuOH
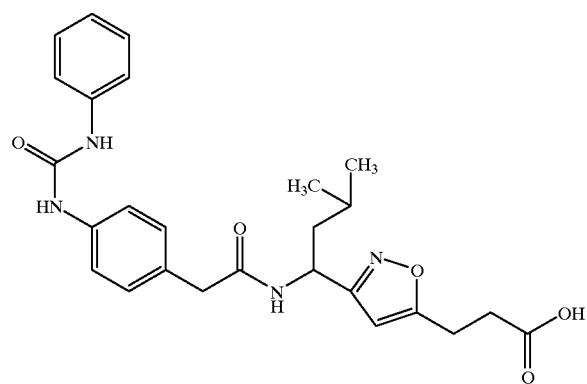
(2.2.13)
Compounds of Formula (1.0.0) in which the B component is a moiety of partial Formula (1.1.0)), i.e., an oxazoline group, may be prepared by a method illustrated generally in the following synthesis scheme:
Synthesis Scheme IV - Step A
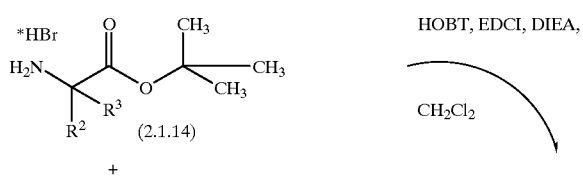
(2.1.14)
+
HOBT, EDCI, DIEA,
CH$_2$Cl$_2$

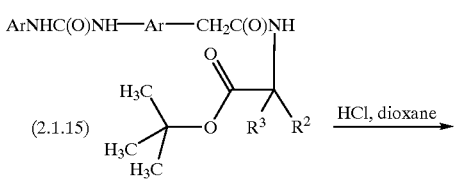

(2.1.2)

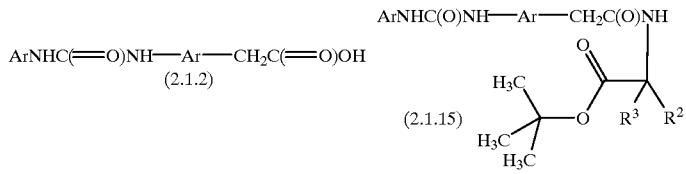

(2.1.15)

The condensation of carboxylic acid (2.1.2) and amine (2.1.14) to give the tert-butyl ester (2.1.15) is shown in Step A, and is analogous to the reaction in Synthesis Scheme 1, Step B. The tert-butyl ester is converted to its corresponding acid, (2.1.16), by subjecting it to acidic conditions such as HCl in a solvent such as dioxane at or near room temperature. The transformation of (2.1.15) to (2.1.16) is shown in Step B below.

Synthesis Scheme IV - Step B

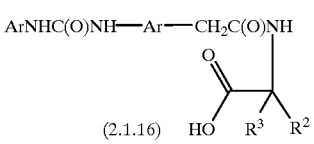

Intermediate acid (2.1.16) is condensed with amine (2.1.17) to give amide (2.1.18) as shown is Step C below, and is analogous to the reaction in Synthesis Scheme 1, Step B. Intermediate amide 19(2.1.18) is cyclized to oxazoline (2.1.19) in the presense of diethylaminosulfur trifluoride (DAST) as shown below in Step D using literature procedures (Pinto et al., *Tetrahedron Lett.* 30, p. 3349, 1989; Jones et al. *Tetrahedron Lett.* 31, p. 3649, 1989).

Synthesis Scheme IV-Step C

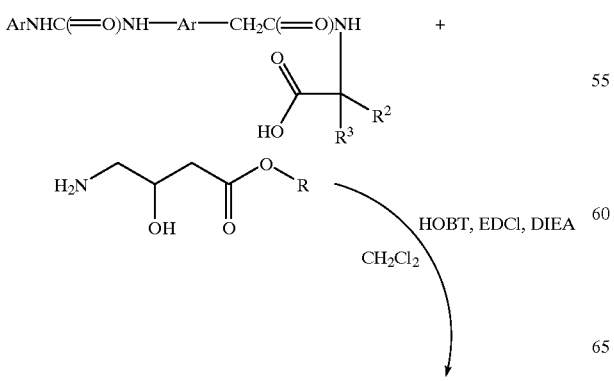

-continued

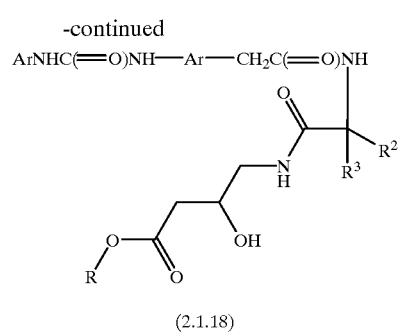

(2.1.18)

Synthesis Scheme IV-Step D

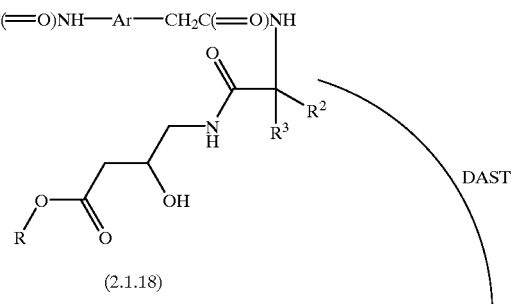

(2.1.18)

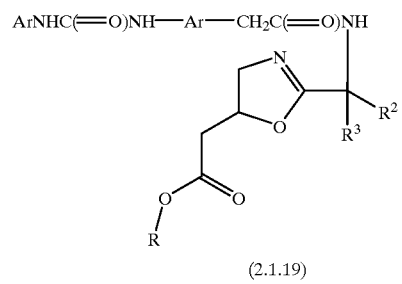

(2.1.19)

Finally, the desired acid (2.1.20) is obtained from ester (2.1.19) in the presence of aqueous base as shown is Step E below and is analogous to the reaction in Synthesis Scheme 1, Step C.

Synthesis Scheme IV - Step E
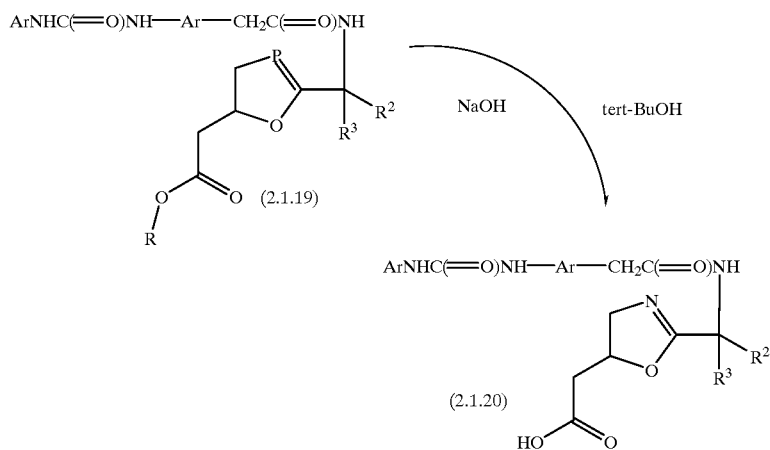
The above described synthesis is broadly applicable to the compounds of Formula (1.0.0). In order to make said synthesis even more clear, there is set out below Synthesis Scheme IV, Steps A through E with reference to a particular compound of the present invention:
Synthesis Scheme IV-α
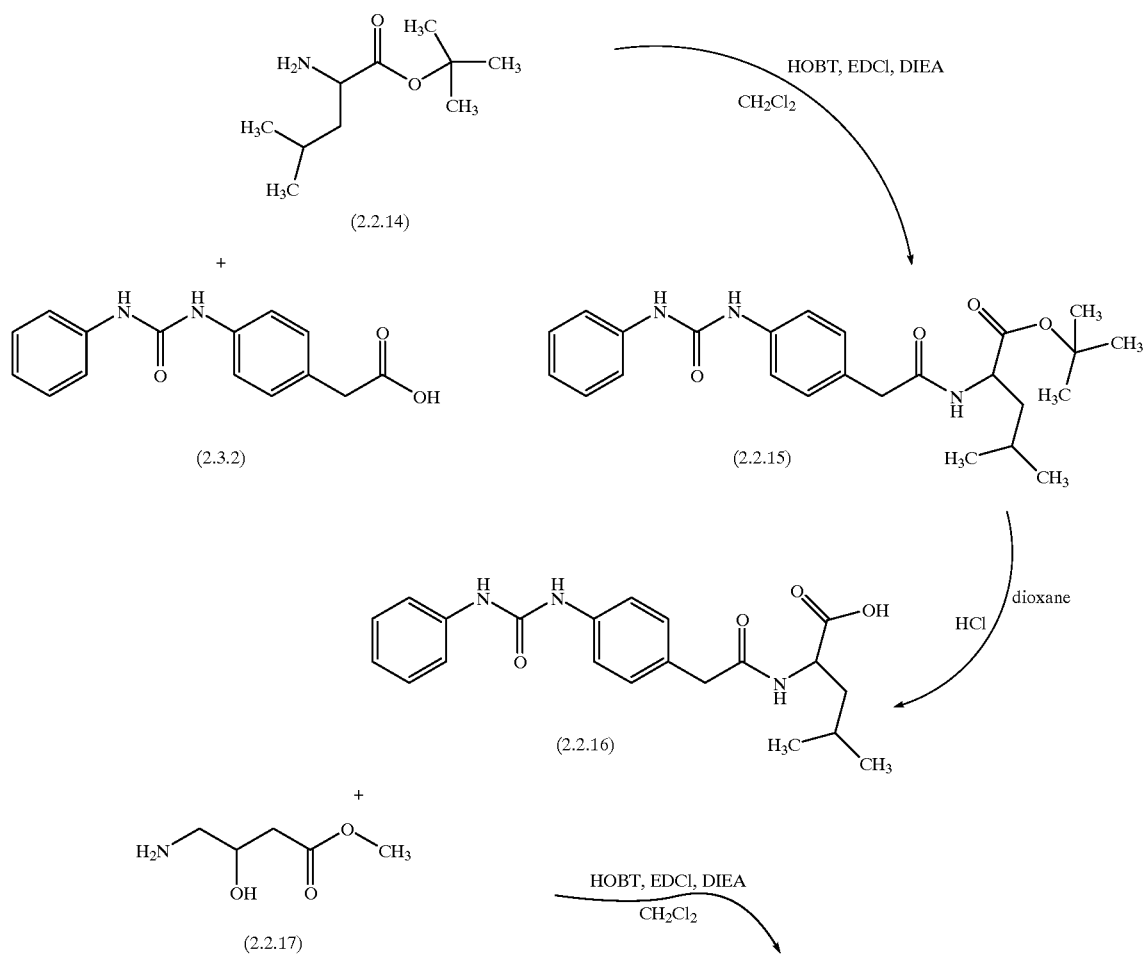

-continued

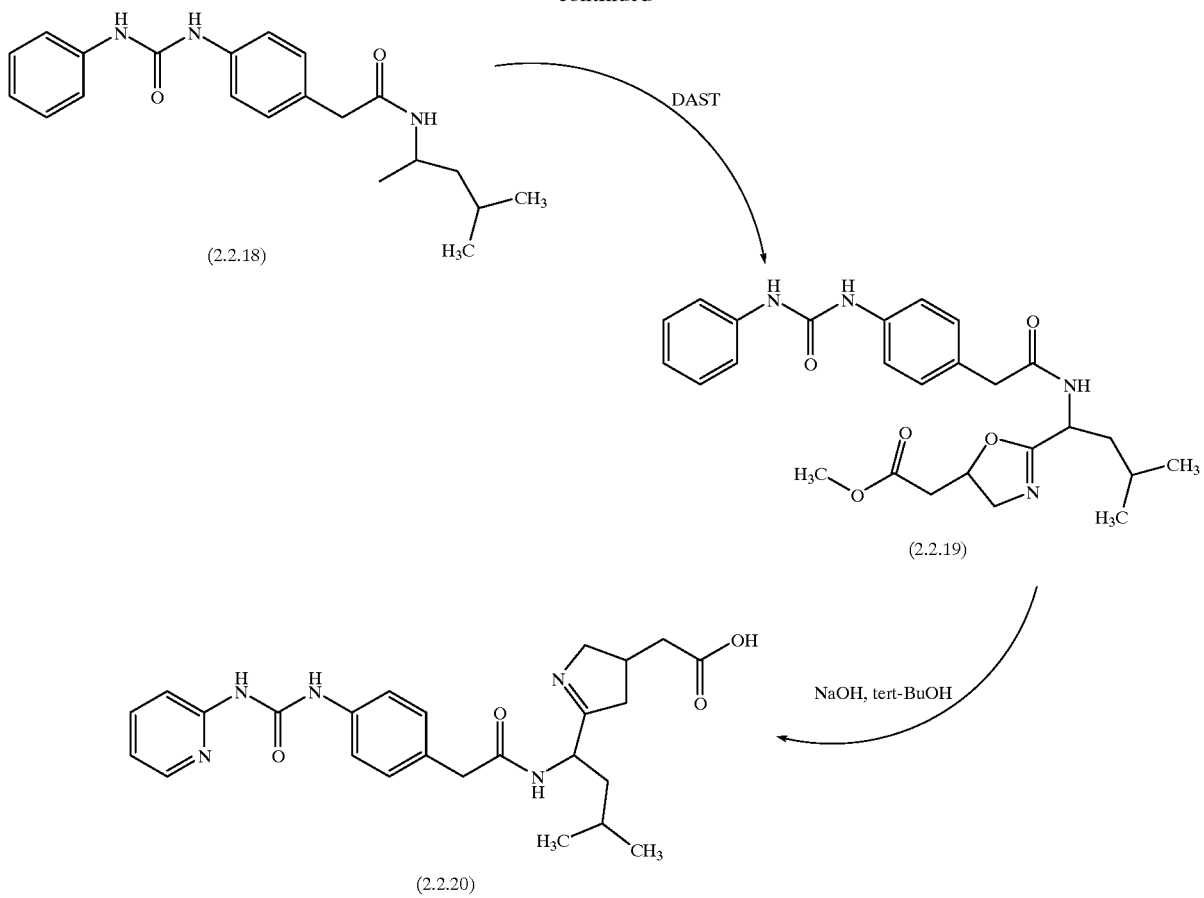

Compounds of Formula (1.0.0) in which the B component is a moiety of partial Formula (1.1.2), i.e., an oxazole group, may be prepared by a method illustrated generally in the following synthesis scheme:

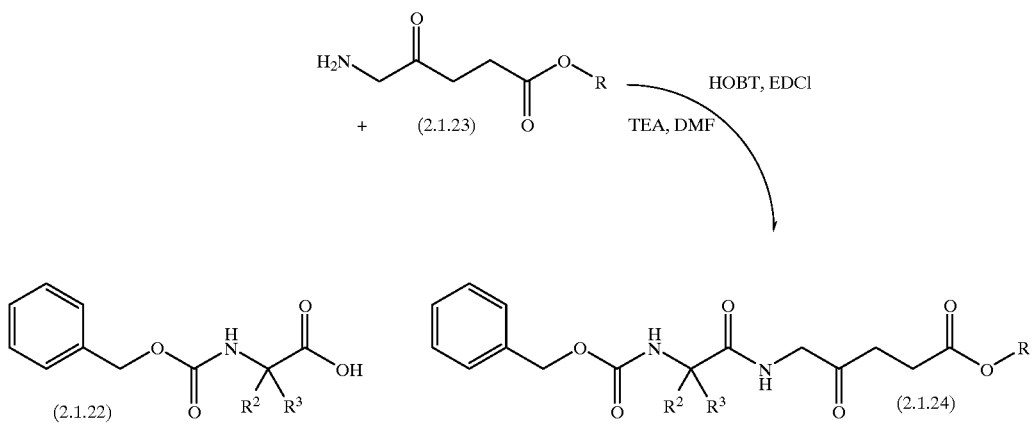

Intermediate acid (2.1.22) is condensed with amine (2.1.23) to give amide (2.1.24) as shown is Step A, and is analogous to the reaction in Synthesis Scheme I, Step B. Intermediate amide (2.1.24) is cyclized to oxazole (2.1.25) in the presense of phosphorous oxychloride in a solvent such as toluene at temperatures between room temperature and 110° C. as shown in Step B below (*J. Org. Chem.* 55, p.386, 1990).

Synthesis Scheme V - Step B

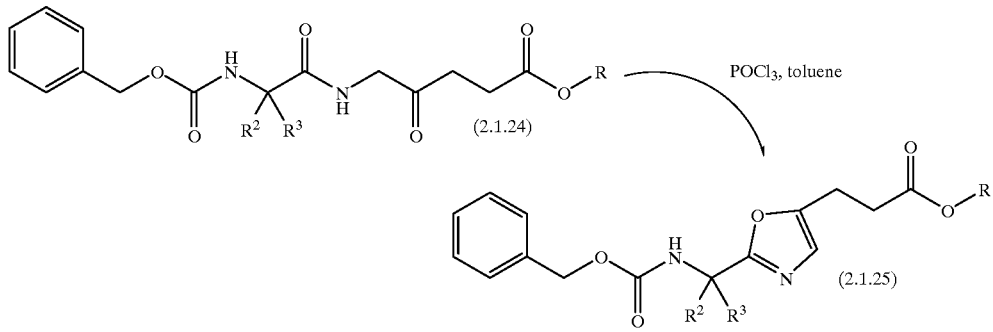

The benzyl carbamate (2.1.25) is converted to the primary amine (2.1.26) by utilizing one of the following reagents using the published literature procedures: $H_2$/Pd-C (*Ber.*, 65, p. 1192, 1932); HBr, AcOH (*J. Org. Chem.*, 17, p. 1564, 1952); 70% HF, pyridine (*J. Chem. Soc., Chem. Commun.*, p. 451, 1976) or $CF_3SO_3H$ (*J. Chem. Soc., Chem. Commun.*, p. 107, 1974). Amine intermediate (2.1.26) is converted to compounds of Formula (1.0.0) by using reactions analogous to Synthesis Scheme I, Steps B and C.

-continued

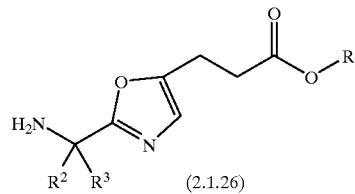

Synthesis Scheme V - Step C

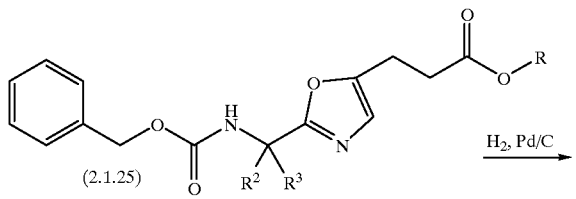

The above described synthesis is broadly applicable to the compounds of Formula (1.0.0). In order to make said synthesis even more clear, there is set out below Synthesis Scheme V, Steps A through C with reference to a particular intermediate compound of the present invention:

Synthesis Scheme V-α

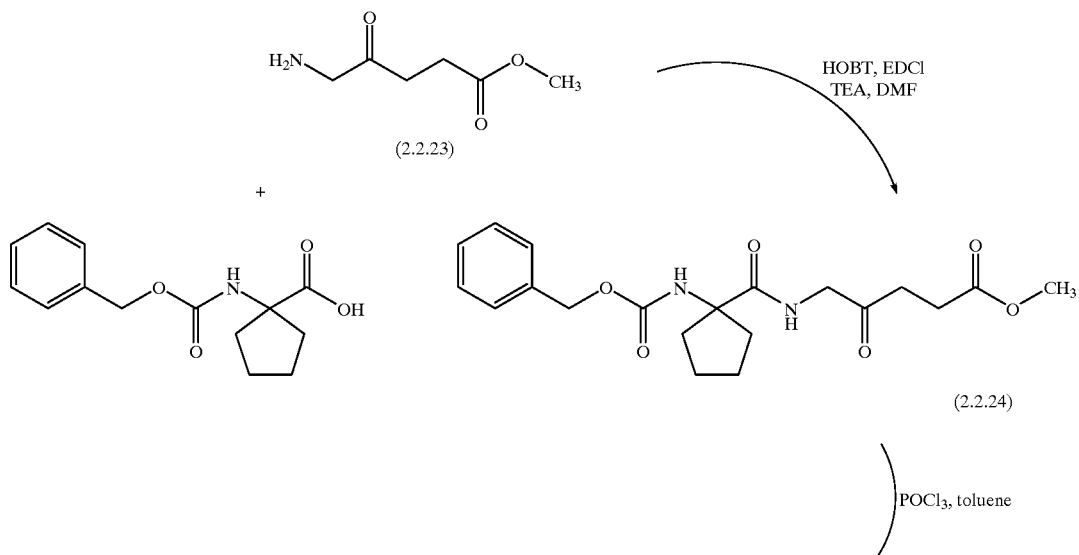

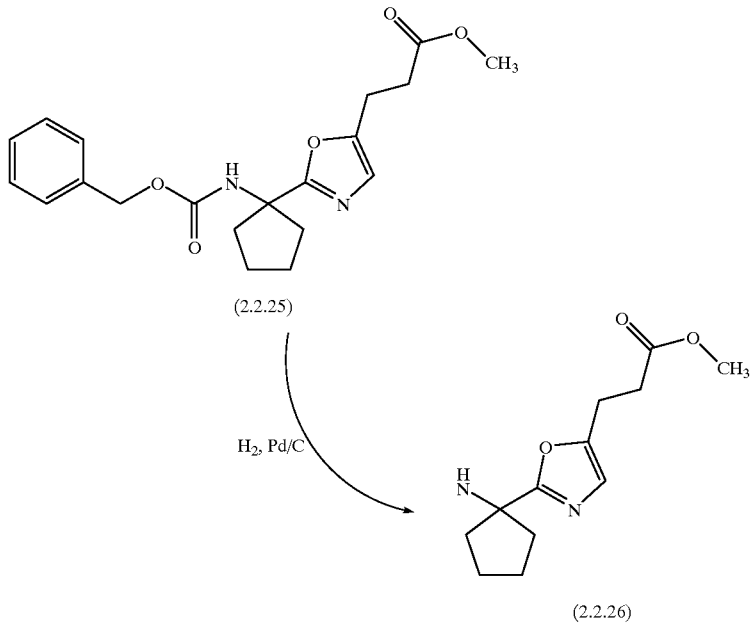

(2.2.25)

(2.2.26)

Compounds of Formula (1.0.0) in which the B component is a moiety of partial Formula (1.1.2), i.e., a thiazole group, may be prepared by a method illustrated generally in the following synthesis scheme:

Synthesis Scheme VI-Step A

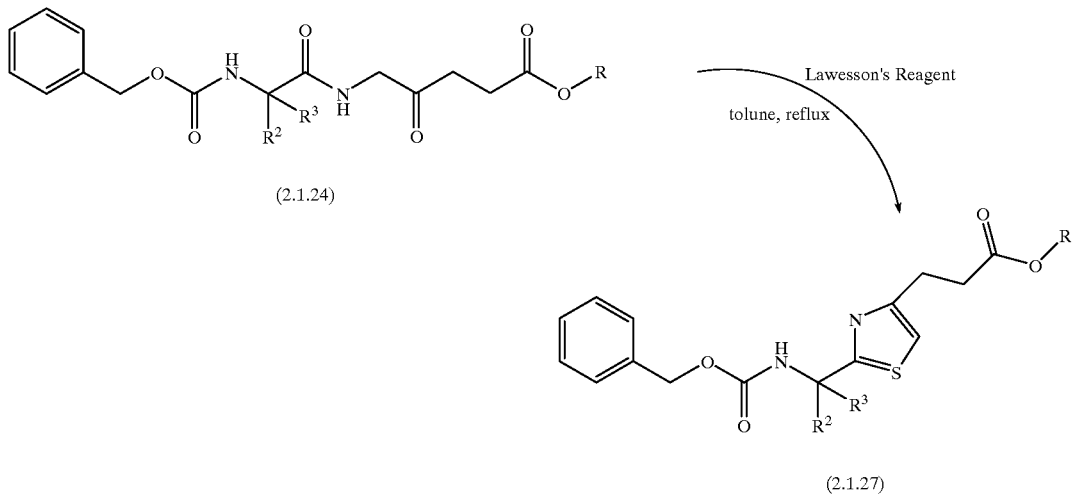

(2.1.24)

(2.1.27)

Intermediate amide (2.1.24) is cyclized to thiazole (2.1.27) using the literature conditions of Lawesson's Reagent [2,4-bis(4-methoxyphenyl)-1,3-dithia-2,4-diphosphetane-2,4-disulfide] in a solvent such as toluene at temperatures between room temperature and 110° C. as shown in Step A. The benzyl carbamate (2.1.27) is converted to the primary amine (2.1.28) as shown in Step B by utilizing one of the following reagents using the published literature procedures: $H_2$/Pd-C (*Ber.*, 65, p. 1192, 1932); HBr, AcOH (*J. Org. Chem.*, 17, p. 1564, 1952); 70% HF, pyridine (*J. Chem. Soc., Chem. Commun.*, p. 451, 1976) or $CF_3SO_3H$ (*J. Chem. Soc., Chem. Commun.*, p. 107, 1974). Amine intermediate (2.1.28) is converted to compounds of Formula (1.0.0) by using reactions analogous to Synthesis Scheme I, Steps B and C.

Synthesis Scheme IV - Step B

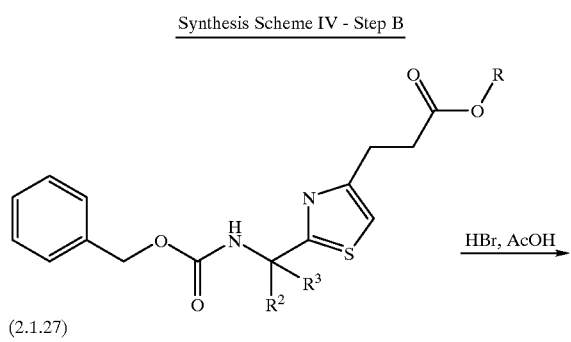

(2.1.27)

HBr, AcOH →

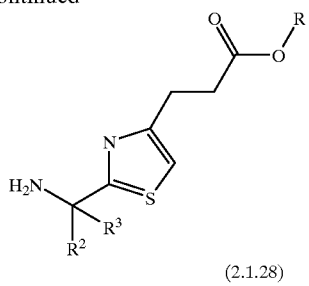

(2.1.28)

The above described synthesis is broadly applicable to the compounds of Formula (1.0.0). In order to make said synthesis even more clear, there is set out below Synthesis Scheme VI, Steps A and B with reference to a particular intermediate compound of the present invention:

Synthesis Scheme VI-α

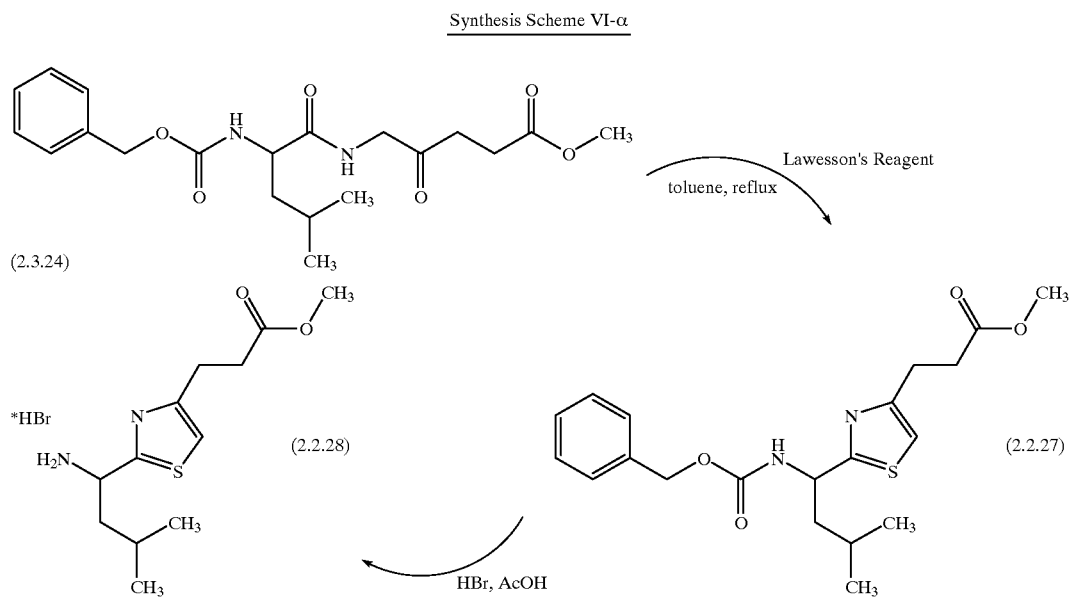

Compounds of Formula (1.0.0) in which the B component is a moiety of partial Formula (1.3.0), e.g., a pyrrolidin-2-yl-thiazol-5-yl group, may be prepared by a method illustrated generally in the following synthesis scheme:

Synthesis Scheme VII - Step A

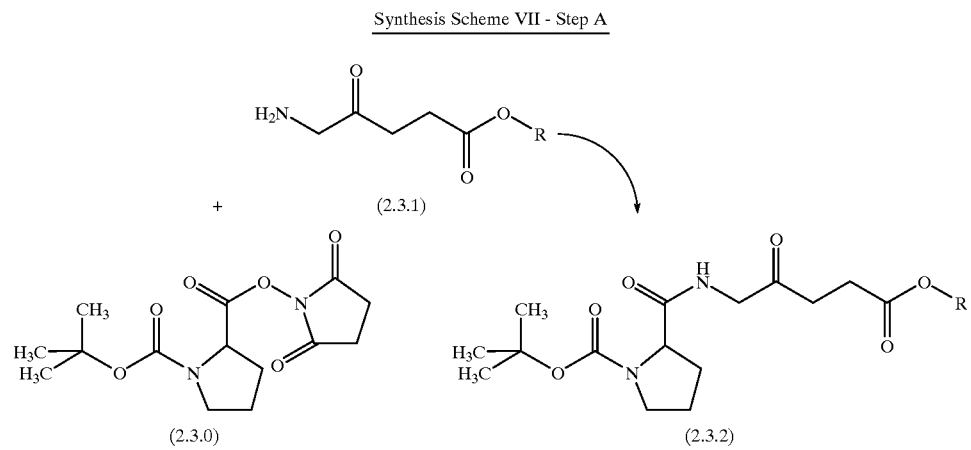

The pyrrolidine dicarboxylic acid (2.3.0) as a protected diester is condensed with amine (2.3.1) to give amide (2.3.2) under reaction conditions which are analogous to those above-described in Synthesis Scheme I, Step B. The amide (2.3.2) is next cyclized to the thiazole (2.3.3) using Lawesson's Reagent under conditions well known in the art and described in detail further herein. This reaction is illustrated in Synthesis Scheme VII, Step B as follows:

Synthesis Scheme VII - Step B

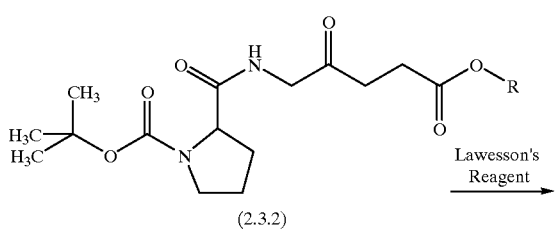

-continued

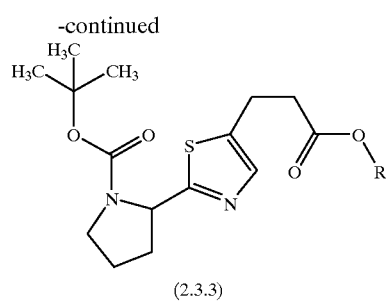

The thiazole (2.3.3) prepared as above described now contains the pyrrolidin-2-yl-thiazol-5-yl component which is a key part of the compounds of Formula (1.0.0) in which the B component is a moiety of partial Formula (1.3.0). The remaining components of a compound of Formula (1.0.0) are prepared in the succeeding steps illustrated below. The nitrogen atom of the pyrrolidinyl group is deprotected to form the pyrrolidinyl-thiazole (2.3.4), followed by condensation of (2.3.4) with an o-tolyl-ureido-phenyl acetic acid reactant (2.3.5) which provides the left-hand portion of a compound of the present invention. There is thereby formed an "R" ester of a compound of Formula (1.0.0), (2.3.6), as shown in Synthesis Scheme VII, Step C as follows:

Synthesis Scheme VII - Step C

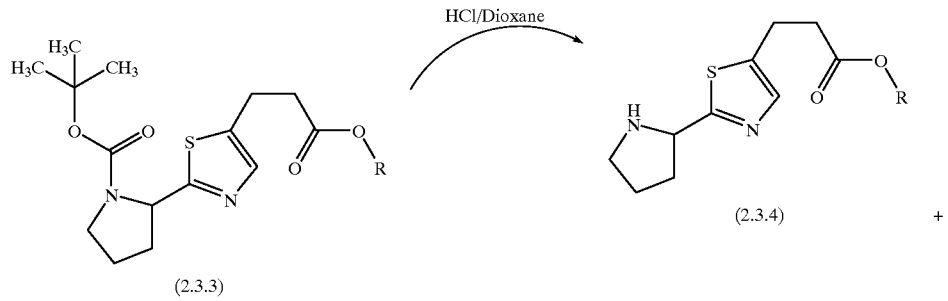

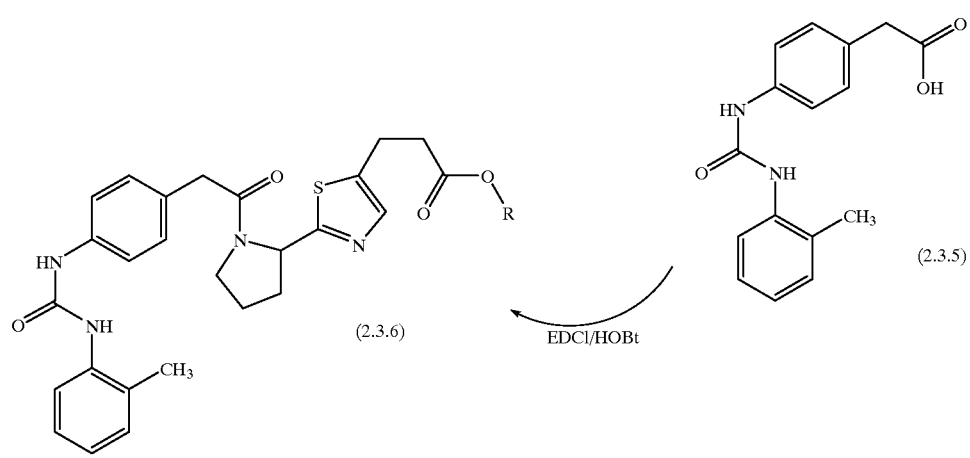

In a final step the ester (2.3.6) is reduced to give the corresponding catboxylic acid (2.3.7) in accordance with well-known procedures. This step is illustrated as Synthesis Scheme VII, Step D, as follows:

Synthesis Scheme VII - Step D

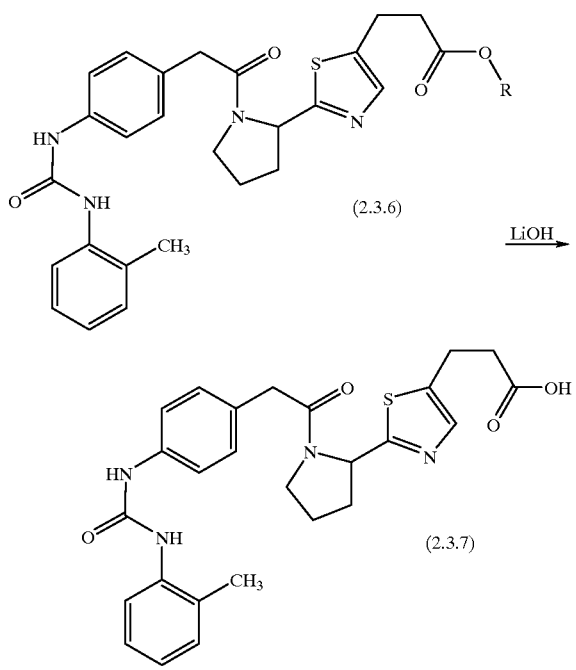

Exemplification of Preferred Embodiments

The examples which follow further illustrate the compounds, compositions and methods of treatment of the present invention, but are not intended to thereby limit the scope of the present invention. A number abbreviations are used in the following examples in order to conserve space. Although these abbreviations are well known to the artisan, they are set out immediately below for clarity and convenience of the reader:

| | |
|---|---|
| BOP | benzotriazol-1-yloxy-tris(dimethylamino) phosphonium hexafluorophosphate |
| DAST | diethylaminosulfur trifluoride |
| DIEA | diisopropylethyl amine |
| DMF | dimethylformamide |
| EDCI | 1-(3-dimethylaminopropyl)-3-ethylcarbodiimide hydrochloride |
| HOBT | 1-hydroxybenzotriazole |
| THF | tetrahydrofuran |

EXAMPLE 1

A. 3-(3-Isobutyl-2-oxo-4-{[4-(3-o-tolyl-ureido)-phenyl]-acetyl}-piperazin-1-yl)-butyric acid

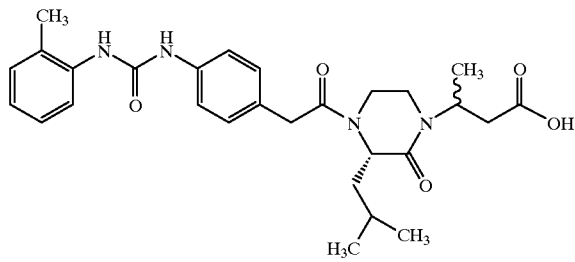

A solution of 3-(3-isobutyl-2-oxo-4-{[4-(3-o-tolyl-ureido)-phenyl]-acetyl}-piperazin-1-yl)-butyric acid methyl ester (20 mg, 0.038 mmol) in a mixture of 1 ml of 0.1 N NaOH and 1 ml of tert-butanol was stirred for 16 hrs at room temperature. The reaction mixture was then concentrated under reduced pressure, dissolved in water (5 ml) and extracted with ether (5 ml×2). The aqueous portion was then acidified to pH<3 with 1N HCl and extracted with ethyl acetate. The combined organics were washed with brine, dried over Na$_2$SO$_4$, filtered and concentrated under reduced pressure to give 16 mg of the title compound as a yellow sticky oil. MS [M+1]+509.3; $^1$H nmr (400 MHz, CD$_3$OD) δ0.88–1.70 (m, 12H), 2.25 (s, 3H), 2.34–4.96 (m, 10H), 6.98 (t, J=7.4 Hz, 1H), 7.11–7.40 (m, 6H), 7.59 (d, J=7.5 Hz, 1).

B. 3-(3-isobutyl-2-oxo-4-{[4-(3-o-tolyl-ureido)-phenyl]-acetyl}-piperazin-1-yl)-butyric acid methyl ester

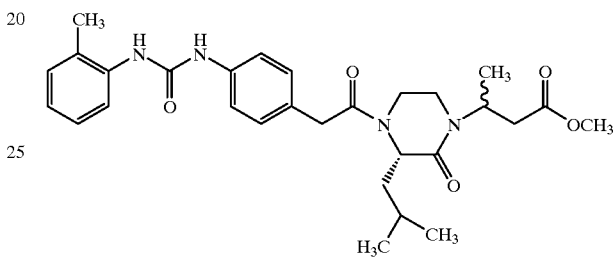

To a stirred mixture of [4-(3-o-tolyl-ureido)-phenyl]-acetic acid (55 mg, 0.19 mmol), diisopropyl ethyl amine (0.17 ml), BOP (86 mg, 0.19 mmol) in DMF (1 ml) was added 3-(3-isobutyl-2-oxo-piperazin-1-yl)-butyric acid methyl ester (50 mg, 0.19 mmol). After stirring 16 h at room temperature the solution was diluted with water and extracted into ethyl acetate. The combined organics were washed with 5% citric acid, saturated NaHCO$_3$, and brine; dried over MgSO$_4$, filtered, and concentrated under reduced pressure. Column chromatography on silica gel eluting with 2% MeOH/CH$_2$Cl$_2$ gave 20 mg of the title compound as a yellow amorphous solid. MS [M+1]+523.3.

C. [4-(3-o-tolyl-ureido)-phenyl]-acetic acid

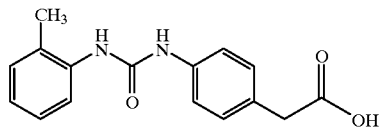

To a stirred mixture of 4-aminophenylacetic acid (15.0 g) and o-tolylisocyanate (10.2 ml) in CH$_2$Cl$_2$ (200 ml) was added triethylamine (13.8 ml). After 1 h the resulting homogeneous solution was concentrated under reduced pressure, dissolved in water (100 ml) and acidified to pH 2 with 1N HCl. The off-white ppt was filtered, suspended in THF (200 ml) and 10 ml conc. HCl was added. The resulting homogeneous solution was concentrated under reduced pressure and recrystallized from EtOAc (800 ml) to give 22 g of the title compound as a white solid. MP 221–20° C.; MS [M+1]+285.2; Analysis calcd. for C16H16N2O3: C (67.59), H (5.67), N (9.85). Found: C (67.22), H (5.78), N (9.69).

D. -(3-isobutyl-2-oxo-piperazin-1-yl)-butyric acid methyl ester: MS [M+1]+257.3.

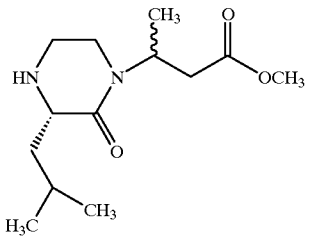

The title compound may be prepared by those skilled in the art using one of the following literature references: (a) Bhatt, U.; Mohamed, N.; Just, G. *Tetrahedron Lett.* 1997, 38 (21), 3679–82; or (b) Sugihara, H. et al. *J. Med. Chem.* 1998, 41, 489–502.

EXAMPLE 2

A. 3-[3-(3-Methyl-1-{2-[4-(3-o-tolyl-ureido)-phenyl]-acetylamino}-butyl)-isoxazol-5-yl]-propionic acid

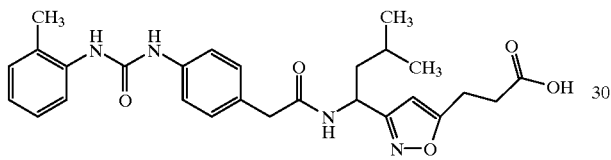

A mixture of 3-[3-(3-methyl-1-{2-[4-(3-o-tolyl-ureido)-phenyl]-acetylamino}-butyl)-isoxazol-5-yl]-propionic acid methyl ester (17 mg) in tert-BuOH (1 ml) and 0.1 N NaOH (1 ml) was stirred at room temperature. After 20 h the mixture was concentrated under reduced pressure, dissolved in water (5 ml) and extracted with EtOAc (5 ml×3). The aqueous layer was then acidified to pH 3 with 1N HCl and extracted with EtOAc. The combined organics were washed with brine; dried over $Na_2SO_4$; filtered and concentrated under reduced pressure to give the title compound as a white amorphous solid. MP=?; MS [M+1]+493.2; $^1$H nmr (400 MHz, $CD_3OD$) δ0.87 (d, 3H), 0.91 (d, 3H), 1.53–1.66 (m, 3H), 2.26 (s, 3H), 2.64 (t, J=7.4 Hz, 2H), 2.97 (t, J=7.5 Hz, 2H), 3.44 (s, 2H), 5.08 (m, 1H), 6.00 (s, 1H), 6.99 (t, 1H), 7.11–7.36 (m, 6H), 7.59 (d, J=7.9 Hz,1H).

B. 3-[3-(3-Methyl-1-{2-[4-(3-o-tolyl-ureido)-phenyl]-acetylamino}-butyl)-isoxazol-5-yl]-propionic acid methyl ester

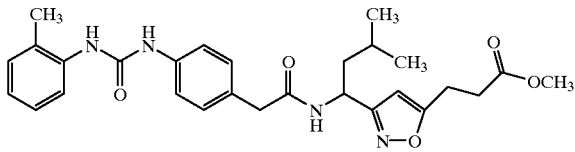

To a stirred solution of [4-(3-o-tolyl-ureido)-phenyl]-acetic acid (305 mg, 1.07 mmol), DIEA (1.3 ml), HOBT (120 mg, 0.89 mmol) and EDCI (170 mg, 0.89 mmol) in $CH_2Cl_2$ (8 ml) at room temperature was added a solution of 3-[3-(1-amino-3-methyl-butyl)-isoxazol-5-yl]-propionic acid methyl ester hydrobromide (272 mg, 0.85 mmol) in $CH_2Cl_2$ (12 ml). After stirring for 16 h at room temperature the mixture was diluted with $CH_2Cl_2$ (20 ml) and poured into water. The layers were separated and the aqueous layer was extracted with $CH_2Cl_2$ (20 ml×3). The combined organics were dried over MgSO4; filtered; and concentrated under reduced pressure. The residue was purified by Flash 40 chromatography using a silica gel column and eluting with 65% EtOAc/hexane to give 220 mg of the title compound as a white amorphous solid. MP 153–4° C.; MS [+1]+507.2; $^1$H nmr (400 MHz, $CDCl_3$) δ0.88 (d, J=6.4 Hz, 6H), 1.53–1.66 (m, 3H), 2.21 (s, 3H), 2.66 (t, J=7.6 Hz, 2H), 3.00 (t, J=7.6 Hz, 2H), 3.49 (s, 2H), 3.68 (s, 3H), 5.15 (dt, J=6.2 and 8.7 Hz, 1H), 5.85 (s, 1H), 6.11 (d, J=8.5 Hz, 1H), 6.65 (s, 1H), 7.00 (s, 1H), 7.05–7.24 (m, 7H), 7.53 (d, 1H); Anal. calcd. for $C_{28}H_{34}N_4O_5$: C (66.39), H (6.76), N (11.05). Found: C (66.29), H (7.11), N (11.11).

C. -[3-(1-amino-3-methyl-butyl)-isoxazol-5-yl]-propionic acid methyl ester hydrobromide

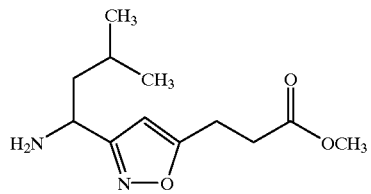

A stirred suspension of 3-[3-(1-benzyloxycarbonylamino-3-methyl-butyl)-isoxazol-5-yl]-propionic acid methyl ester (320 mg, 0.85 mmol) in 30% HBr/AcOH (3 ml) was gently heated until homogeneous. After 4 h at room temperature the orange solution was concentrated to give 275 mg of the title compound as a bright orange amorphous solid. MS [M+1]+ 241.2

D. 3-[3-(1-benzyloxycarbonylamino-3-methyl-butyl)-isoxazol-5-yl]-propionic acid methyl ester

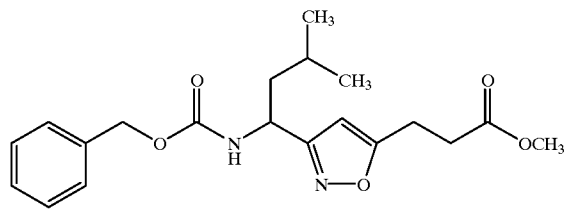

To a stirred solution of [1-(hydroxyimino-methyl)-3-methyl-butyl]-carbamic acid benzyl ester (6.0 g, 22.7 mmol) and pent-4-ynoic acid methyl ester (3.8 g, 34 mmol) in $CH_2Cl_2$ (80 ml) was added triethylamine (0.2 ml) followed by Clorox bleach (80 ml). After 4 h at room temperature the organic phase was separated and the aqueous phase was extracted with $CH_2Cl_2$ (25 ml×3). The combined organics were dried over $MgSO_4$; filtered and concentrated under reduced pressure to give a yellow oil. Purification by Flash 40 chromatography using a silica gel column and eluting with 10–20% EtOAc/hexane gave 2.5 g of the title compound as a waxy pale yellow solid. MS [M+1]+375.3; $^1$H nmr (400 MHz, $CDCl_3$) δ0.91 (m, 6H), 1.51–1.76 (m, 3H), 2.67 (t, J=7.5 Hz, 2H), 3.02 (t, J=7.5 Hz, 2H), 3.67 (s, 3H), 4.89 (m,1H), 5.08 (m, 3H), 5.92 (s, 1H), 7.31 (m, 5H).

E. 1-(hydroxyimino-methyl)-3-methyl-butyl]-carbamic acid benzyl ester

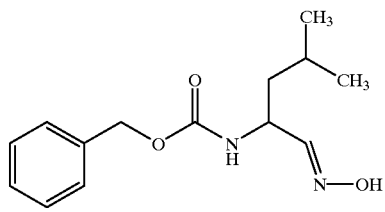

A mixture of (1-formyl-3-methyl-butyl)-carbamic acid benzyl ester (2.13 g, 8.5 mmol), hydroxylamine hydrochloride (0.71 g, 10.2 mmol) and NaOAc (2 g, 24.4 mmol) in MeOH (20 ml) and water (20 ml) was stirred vigorously. After 24 h the mixture was diluted with water (60 ml) and extracted with EtOAc (50 ml×3). The combined organics were washed with water and brine; dried over MgSO4; filtered and concentrated under reduced pressure. Purification by Flash 40 chromatography using a silica gel column and eluting with 15–25% EtOAc/hexane gave 1.5 g of the title compound as a white waxy solid. MS [M+1]+265

EXAMPLE 3

A. [2-(3-Methyl-1-{2-[4-(3-o-tolyl-ureido)-phenyl]-acetylamino}-butyl)-4,5-dihydro-oxazol-5-yl]-acetic acid

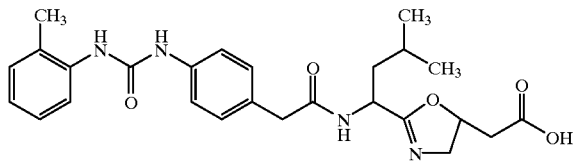

A mixture of [2-(3-methyl-1-{2-[4-(3-o-tolyl-ureido)-phenyl]-acetylamino}-butyl)-4,5-dihydro-oxazol-5-yl]-acetic acid benzyl ester (120 mg) and palladium hydroxide (40 mg) in 10 ml of THF and 10 ml of MeOH was shaken on a Parr Apparatus under 30 p.s.i. H$_2$ for 2 h. The mixture was filtered through Celite and the filtrate concentrated under reduced pressure. The residue was suspended in EtOAc and concentrated under reduced pressure. Trituration with hot EtOAc gave 93 mg of the title compound as a light pink solid. MS [M+1]+481.3; $^1$H nmr (400 MHz, DMSO-d$_6$) δ0.77–0.87 (m, 6H), 1.39–1.59 (m, 3H), 2.10–2.33 (m, 4H, including s at 2.21, 3H), 2.40–5.08 (m, 7H, including q at 3.36, J=14.2 Hz, 2H), 6.90 (t, J=7.4 Hz, 1H), 7.08–7.14 (m, 4H), 7.35 (d, J=6.8 Hz, 2H), 7.79 (d, J=8.1 Hz, 1H), 7.95–8.45 (m, 2H), 9.13–9.23 (m, 1H).

B. [2-(3-methyl-1-{2-[4-(3-o-tolyl-ureido)-phenyl]-acetylamino}-butyl)-4,5-dihydro-oxazol-5-yl]-acetic acid benzyl ester

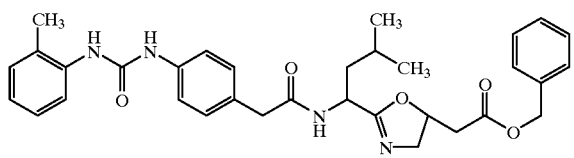

To a stirred suspension of 3-hydroxy-4-(4-methyl-2-{2-[4-(3-o-tolyl-ureido)-phenyl]-acetylamino}-pentanoylamino)-butyric acid benzyl ester (0.73 g) in CH$_2$Cl$_2$ (100 ml) and THF (100 ml) at room temperature was added DAST (0.245 ml). After 2 h an additional 0.245 ml of DAST was added. After 2 h the resulting homogeneous solution was diluted with CH$_2$Cl$_2$ (600 ml), washed with 100 ml of saturated NaHCO$_3$, dried over MgSO$_4$, filtered and concentrated under reduced pressure. Purification by flash chromatography using a silica gel column and elution with 5% MeOH/CH$_2$Cl$_2$ gave a solid which was recrystallized from EtOAc to give 0.255 g of the title compound as a light yellow solid. MS [M+1]+571.2; $^1$H nmr (400 MHz, DMSO-d$_6$) δ0.73–0.81 (m, 6H), 1.42–1.51 (m, 3H), 2.18 (s, 3H), 2.59–2.70 (m, 2H), 3.26–3.42 (m, 3H), 3.81 (m, 1H), 4.44 (m, 1H), 4.85 (m, 1H), 5.08 (s, 2H), 6.88 (t, 1H), 7.06–7.13 (m, 4H), 7.27–7.33 (m, 6H), 7.79 (d, 1H), 7.83 (s, 1H), 8.27–8.30 (m, 1H), 8.91 (s, 1H).

C. 3-Hydroxy-4-(4-methyl-2-{2-[4-(3-o-tolyl-ureido)-phenyl]-acetylamino}-pentanoylamino)-butyric acid benzyl ester

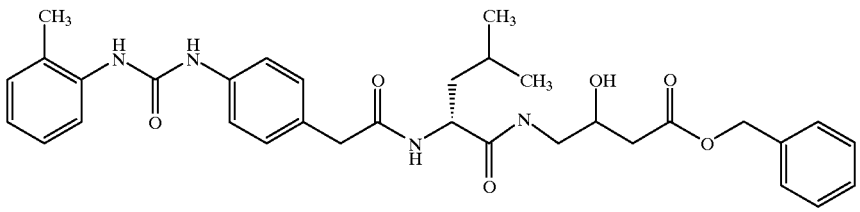

To a stirred solution of 4-methyl-2-{2-[4-(3-o-tolyl-ureido)-phenyl]-acetylamino}-pentanoic acid (3.6 g), 4-amino-3-hydroxy-butyric acid benzyl ester hydrochloride (1.6 g), triethylamine (1 ml) and HOBT (1.06 g) in DMF (50 ml) at room temperature was added EDCI (1.63 g). After stirring 16 h the mixture was poured into 1500 ml ice-water and stirred for 20 min. The resulting ppt was filtered and dried to give a creme colored solid. Recrystallization from EtOAc gave 2.1 g of the title compound as a white solid. MS [M+1]+589.2; $^1$H nmr (400 MHz, DMSO-d$_6$) δ0.73–0.81 (m, 6H), 1.37–1.49 (m, 3H), 2.19 (s, 3H), 2.20–2.28 (m, 1H), 2.46–2.49 (m, 1H), 2.99–3.09 (m, 2H), 3.33 (q, J=13.8 Hz, 2H), 3.90 (m, 1H), 4.19–4.23 (m, 1H), 5.05 (s, 2H), 6.88 (t, 1H), 7.06–7.12 (m, 4H), 7.26–7.34 (m, 6H), 7.75 (d, J=8.1 Hz, 1H), 7.92 (dt, 1H), 8.06 (s, 1H), 8.10 (d, J=8.1 Hz, 1H), 9.13 (s, 1H).

D. Amino-3-hydroxy-butyric acid benzyl ester hydrochloride

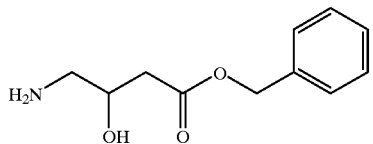

A mixture of 4-tert-butoxycarbonylamino-3-hydroxy-butyric acid benzyl ester (2.1 g) in 4 N HCl/dioxane was stirred at room temperature for 1 h. The mixture was concentrated under reduced pressure to give 1.6 g of the title compound as a white amorphous solid. MS [M+1]+210.1; $^1$H nmr (400 MHz, DMSO-d$_6$) δ2.44–2.50 (m, 1H), 2.61–2.74 (m, 2H), 2.88 (dd, 1H), 4.11 (m, 1H), 5.09 (s, 2H), 5.59 (d, J=5.6 Hz, 1H), 7.35 (m, 5H), 8.01 (broad s, 3H).

E. tert-Butoxycarbonylamino-3-hydroxy-butyric acid benzyl ester

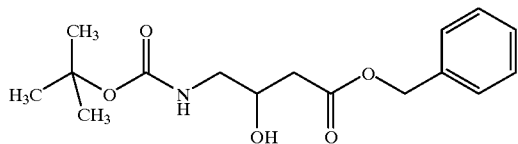

To a stirred solution of 4-tert-butoxycarbonylamino-3-hydroxy-butyric acid (2.0 g) in dry DMF (30 ml) at room temperature was added K$_2$CO$_3$ (2.8 g). After 15 min. benzyl bromide (1.7 g) was added. After 16 h the mixture was poured into 200 ml of water and extracted into EtOAc (200 ml×2). The combined organics were washed with 1 N NaOH (40 ml); water (40 ml×2); brine (40 ml); dried over MgSO$_4$; filtered, and concentrated under reduced pressure to give an oil. Purification by Flash 40 chromatography using a silica gel column and eluting with 30% EtOAc/hexane gave 2.1 g of the title compound as a colorless oil. $^1$H nmr (400 MHz, CDCl$_3$) δ1.43 (s, 9H), 2.53 (m, 2H), 3.07–3.14 (m, 1H), 3.30–3.34 (m, 1H), 4.09–4.13 (m, 1H), 4.95 (broad s, 1H), 5.14 (s, 2H), 7.34 (m, 5H).

F. tert-Butoxycarbonylamino-3-hydroxy-butyric acid

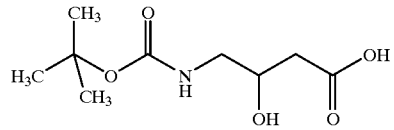

A mixture of 4-amino-3-hydroxy-butyric acid (2.9 g), 1N NaOH (72 ml) and di-tert-butyl dicarbonate (6.6 g) in dioxane (72 ml) was stirred at room temperature. After 16 h the mixture was poured into 200 ml of water and extracted with EtOAc (200 ml×2). The aqueous layer was acidified to pH 4 with 3N HCl and extracted with CH2Cl2 (200 ml×2). The combined organics were washed with water (40 ml);

dried over MgSO4; filtered and concentrated under reduced pressure to give 2.05 g of the title compound as a colorless oil. MS (M-1) 218.2; $^1$H nmr (400 MHz, DMSO-d$_6$) δ1.33 (s, 9H), 2.07 (dd, 1H), 2.30 (dd, J=4.1 and 15.3 Hz,1H), 2.87 (t, J=5.9 Hz, 2H), 3.79 (m, 1H), 6.70 (broad t, 1H).

G. Methyl-2-{2-[4-(3-o-tolyl-ureido)-phenyl]-acetylamino}-pentanoic acid

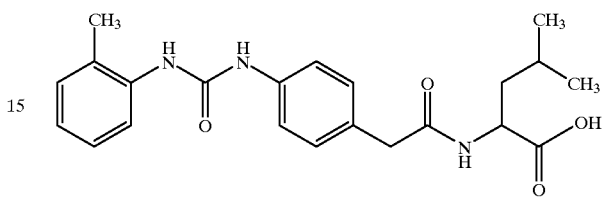

A mixture of 4-methyl-2-{2-[4-(3-o-tolyl-ureido)-phenyl]-acetylamino}-pentanoic acid benzyl ester (4.0 g) and palladium hydroxide on carbon (1.0 g) in 200 ml of MeOH and 200 ml of THF was shaken on a Parr apparatus under 30 p.s.i. of H$_2$. After 2 h the mixture was filtered through celite and the filtrate was concentrated under reduced pressure to give 3.6 g of the title compound as a white solid. MS [M+1]+398.3; $^1$H nmr (400 MHz, DMSO-d$_6$) δ0.79 (d, J=6.4 Hz, 3H), 0.86 (d, J=6.4 Hz, 3H), 1.44–1.63 (m, 3H), 2.21 (s, 3H), 3.36–3.40 (m, 2H), 4.15–4.20 (m, 1H), 6.91 (t, 1H), 7.09–7.14 (m, 4H), 7.33 (d, 2H), 7.81 (d, 1H), 7.89 (s, 1H), 8.26 (d, 1H), 8.97 (s, 1H).

H. Methyl-2-{2-[4-(3-o-tolyl-ureido)-phenyl]-acetylamino}-pentanoic acid benzyl ester

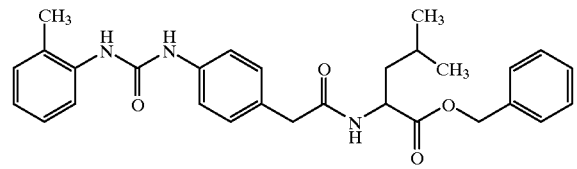

To a stirred solution of [4-(3-o-tolyl-ureido)-phenyl]-acetic acid (3.0 g), L-leucine benzyl ester (4.2 g), triethylamine (1.6 ml), and HOBT (1.6 g) in dry DMF (50 ml) at room temperature was added EDCI (2.4 g). After 16 h the mixture was poured into water (400 ml) and extracted with EtOAc (400 ml×2). The combined organics were washed with 5% citric acid (100 ml); saturated NaHCO$_3$ (100 ml); water (100 ml), brine (100 ml); dried over MgSO$_4$; filtered, and concentrated under reduced pressure to about 100 ml. The resulting suspension was filtered to give 4.0 g of the title compound as a white solid. MS [M+1]+488.2; $^1$H nmr (400 MHz, DMSO-d$_6$) δ0.79 (d, J=6.4 Hz, 3H), 0.86 (d, J=6.4 Hz, 3H), 1.45–1.63 (m, 3H), 2.21 (s, 3H), 3.37 (s, 2H), 4.26–4.31 (m, 1H), 5.07 (s, 2H), 6.91 (t, 1H), 7.09–7.15 (m, 4H), 7.29–7.37 (m, 7H), 7.81 (d, 1H), 7.86 (s, 1H), 8.44 (d, 1H), 8.93 (s, 1H).

EXAMPLE 4

A. (3-Benzyl-2-oxo-4-{[4-(3-o-tolyl-ureido)-phenyl]-acetyl}-piperazin-1-yl)-propionic acid

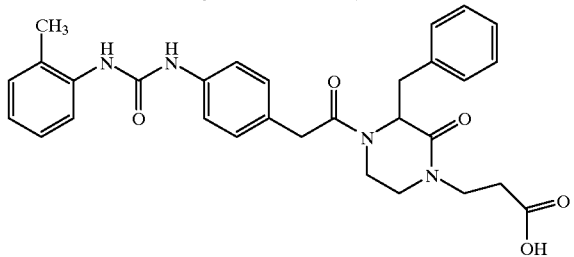

A solution of 3-(3-benzyl-2-oxo-4-{[4-(3-o-tolyl-ureido)-phenyl]-acetyl}-piperazin-1-yl)-propionic acid tert-butyl ester (0.7 g) in 10 ml of 4N HCl/dioxane was stirred at room temperature. After 2 h the solution was concentrated under reduced pressure and the residue was dissolved in 1N NaOH (50 ml) and extracted with EtOAc (20 ml×2). The aqueous phase was acidified to pH 2 with 6N HCl and extracted with EtOAc (20 ml×3). The combined organics were washed with brine; dried over Na2SO4; filtered and concentrated under reduced pressure to give 0.54 g of the title compound as a white amorphous solid. MP=103–5° C.; MS (M-1) 527.

B. (3-Benzyl-2-oxo-4-{[4-(3-o-tolyl-ureido)-phenyl]-acetyl}-piperazin-1-yl)-propionic acid tert-butyl ester

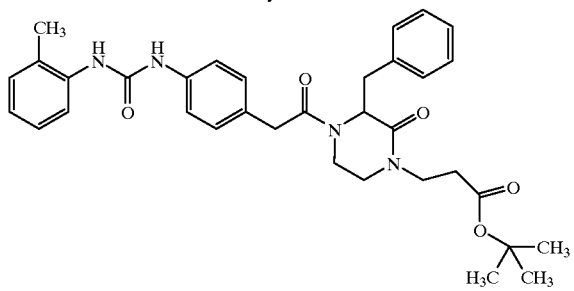

The title compound (white amporphous solid; MS (M-1) 583.4) was prepared in an analogous fashion to Example 1B, utilizing 3-(3-benzyl-2-oxo-piperazin-1-yl)-propionic acid tert-butyl ester as the amine reagent, which can be prepared by those skilled in the art utilizing the procedure referenced in Example 1 D.

EXAMPLE 5

3-Benzo[1,3]dioxol-5-yl-3-(3-isobutyl-2-oxo-4-{[4-(3-o-tolyl-ureido)-phenyl]-acetyl}-piperazin-1-yl)-propionic acid

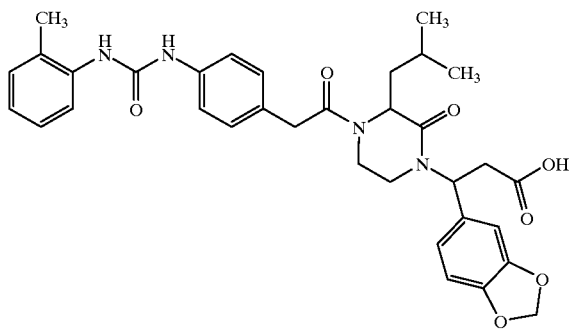

The title compound (white amorphous solid; MS [M+1]+ 615) was prepared in an analogous fashion to Example 4, utilizing 3-benzo[1,3]dioxol-5-yl-3-(3-isobutyl-2-oxo-piperazin-1-yl)-propionic acid tert-butyl ester as the amine reagent in part B, which can be prepared by those skilled in the art utilizing the procedure referenced in Example 1 D.

EXAMPLE 6

3-[5-(2-Carboxy-ethyl)-3-(3-methyl-1-{2-[4-(3-o-tolyl-ureido)-phenyl]-acetylamino}-butyl)-4,5dihydro-isoxazol-5-yl]-propionic acid

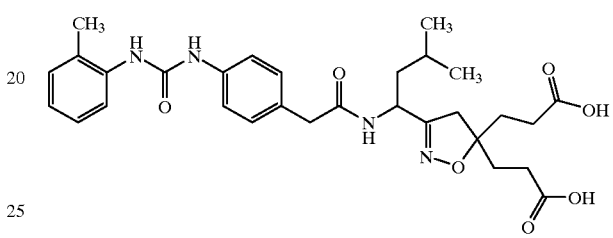

The title compound [M+1]+was prepared in an analogous fashion to Example 2, utilizing [1-(hydroxyimino-methyl)-3-methyl-butyl]-carbamic acid benzyl ester and 4-methylene-heptanedioic acid diethyl ester as the starting materials in part D. White amorphous solid; MP 173–5° C.; MS [M+1]+567.2; Anal. calcd. for $C_{30}H_{38}N_4O_7$: C (63.59), H (6.76), N (9.88). Found: C (63.07), H (7.21), N (9.70).

EXAMPLE 7

3-[3-(3-Methyl-1-{2-[4-(3-o-tolyl-ureido)-phenyl]-acetylamino}-butyl)-4,5-dihydro-isoxazol-5-yl]-propionic acid

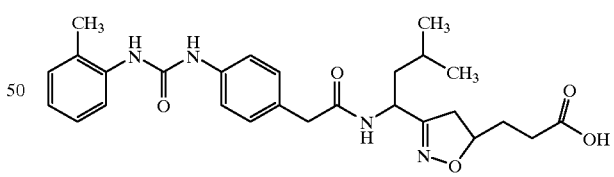

The title compound was prepared in an analogous fashion to Example 2, utilizing [1-(hydroxyimino-methyl)-3-methyl-butyl]-carbamic acid benzyl ester and methyl 4-pentenoate as the starting materials in part D. Light amber solid. $^1H$ nmr (400 MHz, DMSO-$d_6$) δ0.79 (d, J=6.0 Hz, 3H), 0.84 (d, J=5.8 Hz, 3H), 1.48–1.67 (m, 5H), 2.19–2.24 (m, 2H), 2.20 (s, 3H), 2.46–2.54 (m, 1H), 2.93 (dt, J=10.6 and 17.1 Hz, 1H), 3.32 (s, 2H), 4.43 (m, 1H), 4.62 (m, 1H), 6.90 (t, J=7.5 Hz, 1H), 7.08–7.13 (m, 4H), 7.33 (d, J=8.1 Hz, 2H), 7.80 (d, J=8.3 Hz, 1H), 7.85 (s, 1H), 8.22–8.25 (m, 1H), 8.93 (s, 1H); MS (M+) 495.2.

EXAMPLE 8

A. [2-(3-Methyl-1-{2-[4-(3-o-tolyl-ureido)-phenyl]-acetylamino}-butyl)oxazol-5-yl]-propionic acid

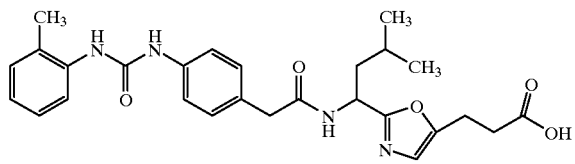

The title compound was prepared in an analogous fashion to Example 2 A–C, using 3-[2-(1-benzyloxycarbonylamino-3-methyl-butyl)-oxazol-5-yl]-propionic acid methyl ester as starting material. White solid; MP 168–170° C.; $^1$H nmr (400 MHz, DMSO-d$_6$) δ0.77 (d, J=6.4 Hz, 3H), 0.83 (d, J=6.6 Hz, 3H), 1.44–1.63 (m, 3H), 2.19 (s, 3H), 2.50 (t, J=7.4 Hz, 2H), 2.79 (t, J=7.3 Hz, 2H), 3.34 (d, 2H), 4.92 (q, J=8.0 Hz, 1H), 6.72 (s, 1H), 6.89 (t, J=7.4 Hz, 1H), 7.07–7.13 (m, 4H), 7.32 (d, J=8.5 Hz, 2H), 7.79 (d, J=8.1 Hz, 1H), 7.84 (s, 1H), 8.54 (d, J=8.3 Hz, 1H), 8.91 (s, 1H); MS (M+) 493.2.

B. 2-(1-Benzyloxycarbonylamino-3-methyl-butyl)-oxazol-5-yl]-propionic acid methyl ester

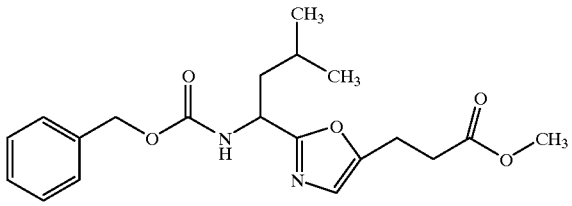

A mixture of 5-(2-benzyloxycarbonylamino-4-methyl-pentanoylamino)4-oxo-pentanoic acid methyl ester (300 mg) and POCl$_3$ (351 mg) in toluene (10 ml) was heated at reflux for 3 h. An additional 351 mg of POCl$_3$ was then added and the mixture was heated at reflux for and additional 2 h. The mixture was cooled to room temperature, poured into aqueous bicarbonate and extracted with EtOAc (2×100 ml). The combined organics were washed with water (20 ml) and brine (20 ml), and dried over MgSO$_4$. The resulting mixture was filtered and concentrated under reduced pressure to give an oil. Purification by flash chromatography using a silica gel column and eluting with 2.5% MeOH in CH$_2$Cl$_2$ gave 100 mg of the title compound as an oil. MS (M+) 375.

C. 2-Benzyloxycarbonylamino-4-methyl-pentanoylamino)-4-oxo-pentanoic acid methyl ester

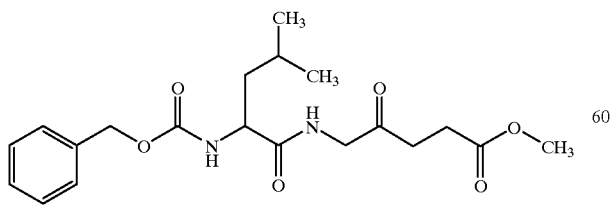

To a stirred solution of 2-benzyloxycarbonylamino-4-methyl-pentanoic acid (1.3 g), 5-amino-4-oxo-pentanoic acid methyl ester hydrochloride (0.90 g) and HOBT (0.67 g) in DMF (15 ml) at room temperature was added TEA (0.7 ml) followed by EDCI (1.05 g). After stirring for 16 h the mixture was poured into water (100 ml) and extracted with EtOAc (2×100 ml). The combined organics were washed with 5% citric acid (20 ml), saturated aqueous bicarbonate (20 ml) and water (20 ml); dried over MgSO$_4$; filtered; and concentrated under reduced pressure to give an oil. Purification by flash chromatography using a silica gel column and eluting with 2.5% MeOH/CH$_2$Cl$_2$ gave 0.53 g of the title compound as an oil. MS [M+1]+393.

EXAMPLE 9

3-[3-(1-{2-[4-(3-o-Tolyl-ureido)-phenyl]-acetylamino}-cyclopentyl)-isoxazol-5-yl]-propionic acid

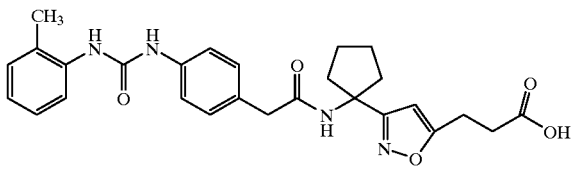

The title compound was prepared in an analogous fashion to Example 2, utilizing [1-(hydroxyimino-methyl)-cyclopentyl]-carbamic acid benzyl ester and methyl pent-4-ynoate as the starting materials in part D. White solid; MP 195–7° C.; MS [M+1]+491.3; Anal. calcd. for C$_{27}$H$_{30}$N$_4$O$_5$: C (66.11), H (6.16), N (11.42). Found: C (65.85), H (6.22), N (11.24).

EXAMPLE 10

A. [3-(3-Methyl-1-{2-[4-(3-pyridin-2-yl-ureido)-phenyl]-acetylamino}-butyl)-isoxazol-5-yl]-propionic acid

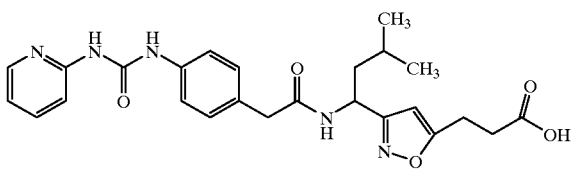

The title compound was prepared in an analogous fashion to Example 2, utilizing [4-(3-pyridin-2-yl-ureido)-phenyl]-acetic acid in part B. White solid; MP 159–161° C.; $^1$H nmr (400 MHz, CD$_3$OD) δ0.87 (d, J=6.0 Hz, 3H), 0.91 (d, J=6.2 Hz, 3H), 1.56–1.73 (m, 3H), 2.64 (t, J=7.3 Hz, 2H), 2.98 (t, J=7.3 Hz, 2H), 3.47 (s, 2H), 5.06–5.10 (m, 1H), 6.01 (s, 1H), 6.96–6.99 (m, 1H), 7.14 (d, 1H), 7.22 (d, 2H), 7.45 (d, 2H), 7.67–7.72 (m, 1H), 8.25 (m, 1H): MS [M+1]$^+$480.3.

B. (3-Pyridin-2-yl-ureido)-phenyl]-acetic acid

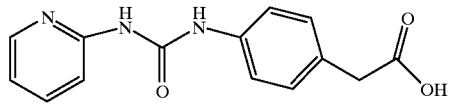

The title compound was prepared in an analogous fashion to Example 1C, using 2-pyridyl isocyanate and 4-aminophenylacetic acid as starting materials. MS [M+1]$^+$ 272.2.

EXAMPLE 11

A. [2-(3-Methyl-1-{2-[4-(3-pyridin-2-yl-ureido)-phenyl]-acetylamino}-butyl)-thiazol-5-yl]-propionic acid

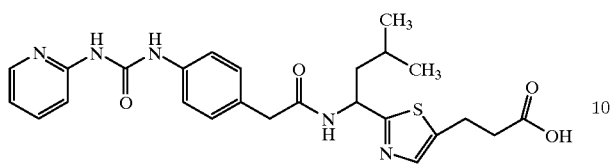

The title compound was prepared in an analogous fashion to Example 2 A–C, using [4-(3-pyridin-2-yl-ureido)-phenyl]-acetic acid in 2B and 3-[2-(1-benzyloxycarbonylamino-3-methyl-butyl)-thiazol-5-yl]-propionic acid methyl ester in 2C. Off-white solid; MP 173–5° C.; $^1$H nmr (400 MHz, CD$_3$OD) δ0.88 (d, J=6.6 Hz, 3H), 0.92 (d, J=6.6 Hz, 3H), 1.60–1.77 (m, 3H), 2.59 (t, J=7.3 Hz, 2H), 3.05 (t, J=7.3 Hz, 2H), 3.50 (s, 2H), 5.19 (q, 1H), 6.69–6.99 (m, 1H), 7.14 (d, 1H), 7.24 (d, 2H), 7.38 (s, 1H), 7.46 (d, 2H), 7.67–7.71 (m, 1H), 8.25 (d, 1H), 8.69 (d, 1H); MS [M+1]$^+$496.2.

B. [2-(1-Benzyloxycarbonylamino-3-methyl-butyl)-thiazol-5-yl]-propionic acid methyl ester

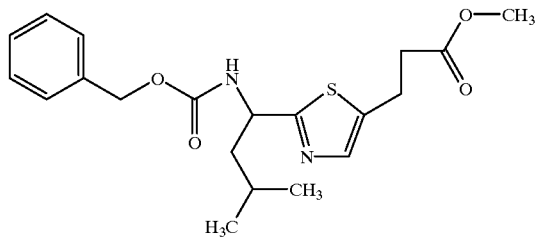

A mixture of 5-(2-benzyloxycarbonylamino-4-methyl-pentanoylamino)-4-oxo-pentanoic acid methyl ester (0.96 g) and Lawesson's Reagent [2,4-bis(4-methoxyphenyl)-1,3-dithia-2,4-diphosphetane-2,4-disulfide] (2.4 g) in 20 ml of anhydrous toluene was heated at reflux. After 5 h the mixture was poured into water (200 ml) and extracted with EtOAc (2×200 ml). The combined organics were washed with water (40 ml) and brine (40 ml), dried over MgSO$_4$, filtered and concentrated under reduced pressure to an oil. Purification by flash chromatography using a silica gel column and eluting with 2.5% MeOH/CH$_2$Cl$_2$ gave 0.39 g of the title compound as a colorless oil. MS [M+1]+391.

EXAMPLE 12

4-[3-(3-Methyl-1-{2-[4-(3-o-tolyl-ureido)-phenyl]-acetylamino}-butyl)-isoxazol-5-yl]-butyric acid

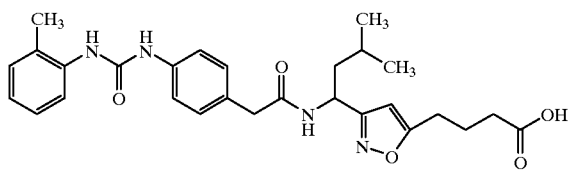

The title compound was prepared in an analogous fashion to Example 2, utilizing [1-(hydroxyimino-methyl)-3-methyl-butyl]-carbamic acid benzyl ester and methyl hex-5-ynoate as starting materials in step D. White solid; $^1$H nmr (400 MHz, DMSO-d$_6$) δ0.81 (d, J=5.8 Hz, 3H), 0.85 (d, J=5.8 Hz, 3H), 1.50–1.82 (m, 5H), 2.21 (s, 3H), 2.25 (t, J=7.3 Hz, 2H), 2.70 (t, J=7.5 Hz, 2H), 3.35 (s, 2H), 4.92–4.98 (m, 1H), 6.10 (s, 1H), 6.91 (t, 1H), 7.09–7.15 (m, 4H), 7.34 (d, 2H), 7.81 (d, 1H), 7.86 (s, 1H), 8.43 (d, 1H), 8.94 (s, 1H); MS [M+1]$^+$507.3.

EXAMPLE 13

3-[2-(3-Methyl-1-{2-[4-(3-o-tolyl-ureido)-phenyl]-acetylamino}-butyl)-thiazol-5-yl]-propionic acid

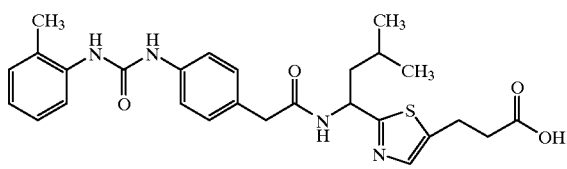

The title compound was prepared in an analogous fashion to Example 11 using the appropriate starting materials and reagents. White solid; $^1$H nmr (400 MHz, DMSO-d$_6$) δ0.81 (d, J=6.4 Hz, 3H), 0.87 (d, J=6.4 Hz, 3H), 1.56–1.74 (m, 3H), 2.21 (s, 3H), 2.53 (t, J=7.3 Hz, 2H), 2.96 (t, J=7.3 Hz, 2H), 3.36 (d, J=14 Hz, 1H), 3.41 (d, J=14 Hz, 1H), 5.03 (q, 1H), 6.91 (t, 1H), 7.09–7.15 (m, 4H), 7.35 (d, 2H), 7.39 (s, 1H), 7.81 (d, 1H), 7.87 (s, 1H), 8.69 (d, 1H), 8.95 (s, 1H); MS [M+1]$^+$509.2.

EXAMPLE 14

3-{3-[3-Methyl-1-(2-{4-[3-(4-methyl-pyridin-3-yl)-ureido]-phenyl}-acetylamino)-butyl]-isoxazol-5-yl}-propionic acid

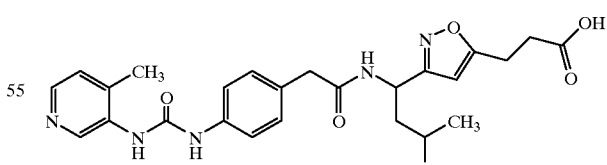

The title compound was prepared in an analogous fashion to Example 2, utilizing {4-[3-(4-methyl-pyridin-3-yl)-ureido]-phenyl}-acetic acid in part B. White solid; MS [M−1]$^+$492.

EXAMPLE 15

3-{2-[1-(2-{4-[3-(2-Chloro-phenyl)-ureido]-phenyl}-acetylamino)-3-methyl-butyl]-thiazol-5-yl}-propionic acid

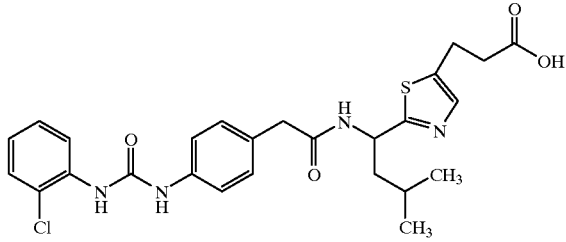

The title compound was prepared in an analogous fashion to Example 11 using the appropriate starting materials and reagents. White solid; MP 173–5° C.; MS [M−1]⁺527; Anal. calcd. for $C_{26}H_{29}ClN_4O_4S$: C (59.03), H (5.52), N (10.59). Found: C (58.89), H (5.60), N (10.49).

EXAMPLE 16

3-{2-[1-(2-{4-[3-(2-Methoxy-phenyl)-ureido]-phenyl}-acetylamino)-3-methyl-butyl]-thiazol-5-yl}-propionic acid

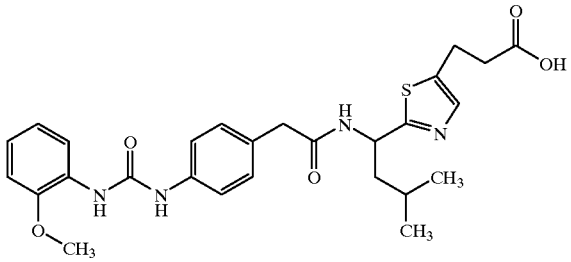

The title compound was prepared in an analogous fashion to Example 11 using the appropriate starting materials and reagents. White solid; MP 197–198° C.; MS [M−1]⁺523; Anal. calcd. for $C_{27}H_{32}N_4O_5S$: C (62.90), H (6.26), N (10.87). Found: C (62.09), H (6.33), N (9.91).

EXAMPLE 17

3-{2-[1-(2-{4-[3-(2-Fluoro-phenyl)-ureido]-phenyl}-acetylamino)-3-methyl-butyl]-thiazol-5-yl}-propionic acid

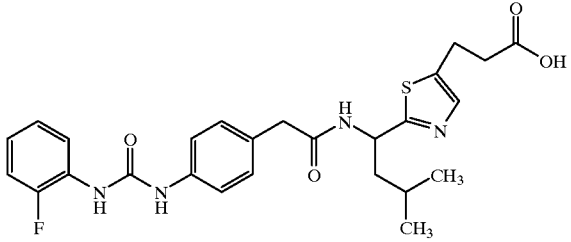

The title compound was prepared in an analogous fashion to Example 11 using the appropriate starting materials and reagents. White solid; MP 83–85° C.; MS [M−1]⁺511.1.

EXAMPLE 18

A. 3-[3-(3-Methyl-1-{2-[4-(3-o-tolyl-ureido)-phenyl]-acetylamino}-butyl)-isoxazol-5-yl]-acrylic acid

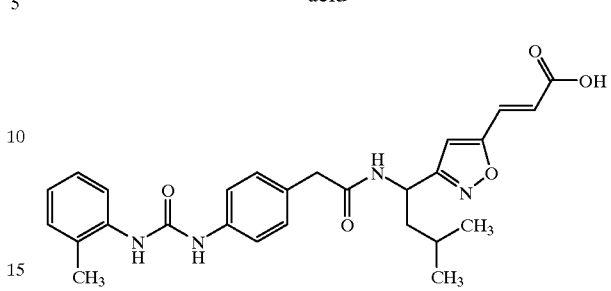

The title compound was prepared in an analogous fashion to Example 2 using 3-[3-(1-benzyloxycarbonylamino-3-methyl-butyl)-isoxazol-5-yl]-acrylic acid ethyl ester as the starting material in part C. White solid; MP 136–8° C.; MS [M−1]⁺489.

B. 3-[3-(1-Benzyloxycarbonylamino-3-methyl-butyl)-isoxazol-5-yl]-acrylic acid ethyl ester

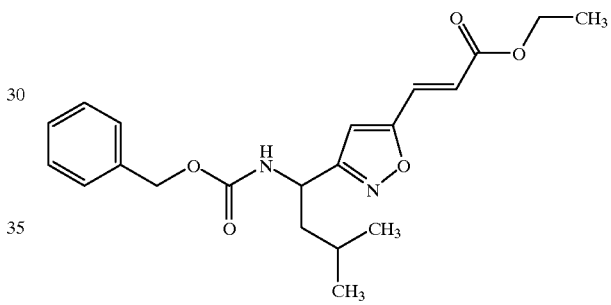

A stirred mixture of [1-(5-formyl-isoxazol-3-yl)-3-methyl-butyl]-carbamic acid benzyl ester (407 mg, 1.3 mmol), pyridine (10 ml) and ethyl hydrogen malonate (255 mg, 1.9 mmol) was warmed to 550° C. After 2 days the mixture was cooled to room temperature, poured into water and extracted into EtOAc (3×). The combined organics were washed with 1N HCl, water, and brine; dried over NaSO4, filtered and concentrated under reduced pressure to give 480 mg of a yellow oil. Purification by Flash 40(small) chromatography eluting with 1:3 EtOAc/hexane gave 220 mg of the title compound as a light yellow oil. MS [M+1]⁺387.

C. [1-(5-Formyl-isoxazol-3-yl)-3-methyl-butyl]-carbamic acid benzyl ester

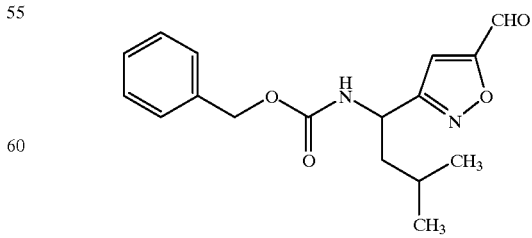

A stirred mixture of [1-(5-diethoxymethyl-isoxazol-3-yl)-3-methyl-butyl]-carbamic acid benzyl ester (920 mg, 2.4 mmol), acetone (50 ml) and H2SO4 (10 drops) was heated to reflux. After 35 min. the mixture was cooled to room temperature, neutralized with solid NaHCO3 and concentrated under reduced pressure. The resulting paste was taken up in EtOAc; washed with water and brine; dried over Na$_2$SO$_4$; filtered; and concentrated under reduced pressure to give a light yellow oil. Purification by Flash 40(small) chromatography eluting with 1:3 EtOAc/hexane gave 407 mg of the title compound as a light yellow oil. MS [M+1]$^+$ 317.

D. [1-(5-Diethoxymethyl-isoxazol-3-yl)-3-methyl-butyl]-carbamic acid benzyl ester

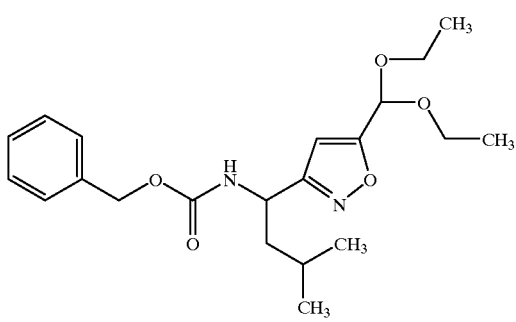

A mixture of [1-(hydroxyimino-methyl)-3-methyl-butyl]-carbamic acid benzyl ester (1.2 g, 4.5 mmol), 3,3-diethoxy-propyne (1.5 g, 11.4 mmol), CH$_2$Cl$_2$ (40 ml) and TEA (6 drops) was stirred until homogeneous, then Clorox bleach (20 ml) was added. After stirring vigorously for 12 h the layers were separated and the aqueous layer was extracted with CH$_2$Cl$_2$ (3×). The combined organics were dried over Na$_2$SO$_4$; filtered; and concentrated under reduced pressure to give a yellow oil. Purification by Flash 40(small) chromatography eluting with 10% EtOAc in hexanes gave 920 mg of the title compound as a colorless oil. MS [M+1]$^+$391.

EXAMPLE 19

3-{2-[1-(2-{4-[3-(2,6-Dichloro-phenyl)-ureido]-phenyl}-acetylamino)-3-methyl-butyl]-thiazol-5-yl}-propionic acid

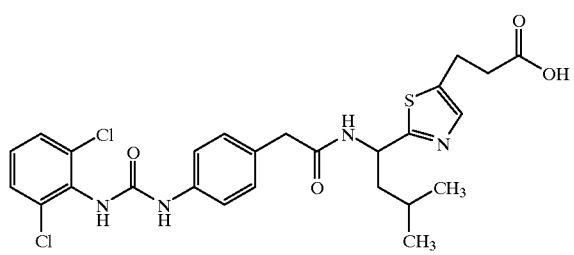

The title compound was prepared in an analogous fashion to Example 11 using the appropriate starting materials and reagents. White solid; MP 148–50° C.; MS [M−1]$^+$561.

EXAMPLE 20

3-{2-[1-(2-{4-[3-(2,6-Dimethyl-phenyl)-ureido]-phenyl}-acetylamino)-3-methyl-butyl]-thiazol-5-yl}-propionic acid

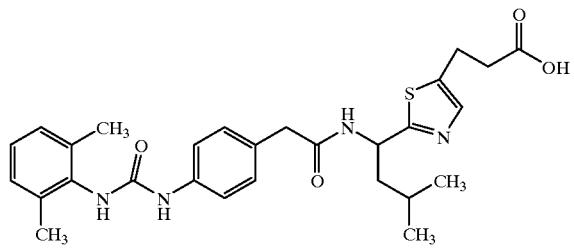

The title compound was prepared in an analogous fashion to Example 11 using the appropriate starting materials and reagents. White solid; MP 125–7° C.; MS [M−1]$^+$521.

EXAMPLE 21

3-{2-[1-(2-{4-[3-(2-Chloro-6-methyl-phenyl)-ureido]-phenyl}-acetylamino)-3-methyl-butyl]-thiazol-5-yl}-propionic acid

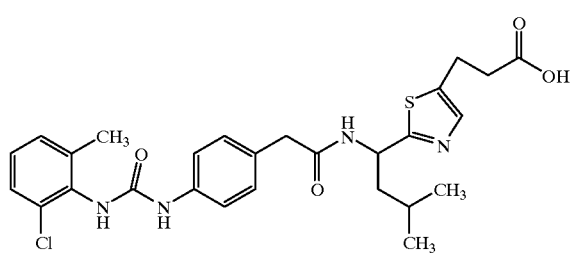

The title compound was prepared in an analogous fashion to Example 11 using the appropriate starting materials and reagents. White solid; MP 160–2° C.; MS [M−1]$^+$541.

EXAMPLE 22

3-[2-(3-Methyl-1-{2-[4-(3-phenyl-ureido)-phenyl]-acetylamino}-butyl)-thiazol-5-yl]-propionic acid

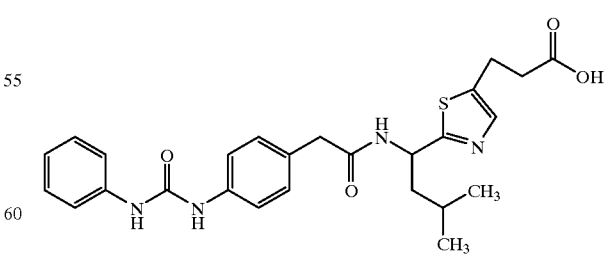

The title compound was prepared in an analogous fashion to Example 11 using the appropriate starting materials and reagents. White solid; MP 146–8° C.; MS [M+1]$^+$495.3.

EXAMPLE 23

N-Hydroxy-3-[2-(3-methyl-1-{2-[4-(3-o-tolyl-ureido)-phenyl]-acetylamino}-butyl)-thiazol-5-yl]-propionamide

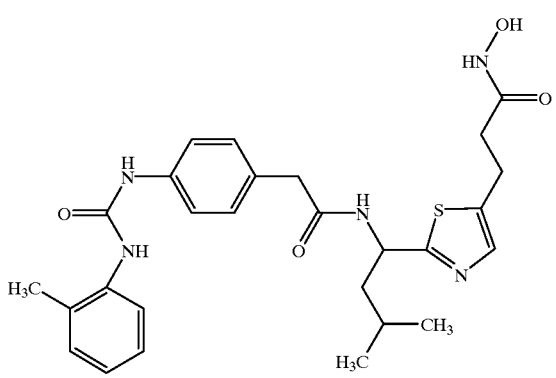

Hydroxylamine hydrochloride (6.96 g) was suspended in methanol (35 mL) and heated to 90° C. This solution was added to potassium hydroxide (8.34 g) dissolved in methanol (21mL) After 15 minutes of stirring, the solution was filtered and 3-[2-(3-methyl-1-{2-[4-(3-o-tolyl-ureido)-phenyl]-acetylamino}-butyl)-thiazol-5-yl]-propionic acid methyl ester (0.80 g, 1.53 mmol) was added. The reaction was stirred at room temperature for 15 minutes, 1N HCl (50 mL) was added, and the methanol was removed in vacuo. The residue was partitioned between ethyl acetate and hydrochloric acid (1N). The organic portion was dried over sodium sulfate and the solvent removed in vacuo. The title compound (0.175 g, 17%) was isolated by crystallization from a mixture of ethyl acetate and methanol. MS [M+1] 524.1.

EXAMPLE 24

3-{3-[1-(2-{4-[3-(2-Chloro-phenyl)-ureido]-phenyl}-acetylamino)-3-methyl-butyl]-isoxazol-5-yl}propionic acid

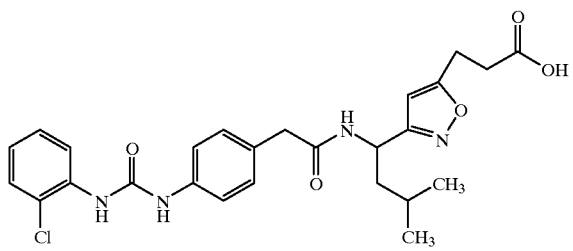

The title compound was prepared in an analogous fashion to Example 2 using the appropriate starting materials and reagents. White solid; MP 143–5° C.; MS [M–1]$^+$511.2.

EXAMPLE 25

3-[2-(1-{2-[4-(3-o-Tolyl-ureido)-phenyl]-acetylamino}-but-3-enyl)-thiazol-5-yl]-propionic acid

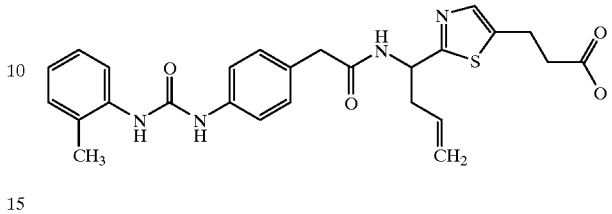

The title compound was prepared in an analogous fashion to Example 11 using the appropriate starting materials and reagents. White amorphous solid; MS [M+1]$^+$493.

EXAMPLE 26

A. 3-{3-[1-(2-{4-[3-(2-Chloro-phenyl)-ureido]-phenyl}-acetylamino)-3-methyl-butyl]-isoxazol-5-yl}-3-oxo-propionic acid ethyl ester

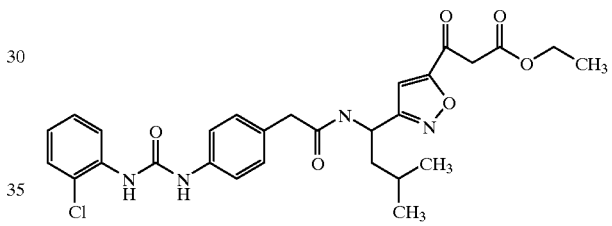

The title compound was prepared in an analogous fashion to Example 2 using 3-[3-(1-amino-3-methyl-butyl)-isoxazol-5-yl]-3-oxo-propionic acid ethyl ester hydrochloride in step B. White solid; MP 150–2° C.; MS [M+1]$^+$555.5.

B. 3-[3-(1-Amino-3-methyl-butyl)-isoxazol-5-yl]-3-oxo-propionic acid ethyl ester hydrochloride

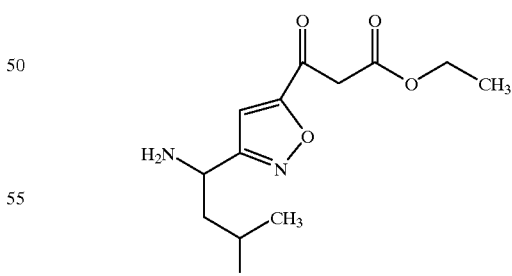

A solution of 3-[3-(1-tert-butoxycarbonylamino-3-methyl-butyl)-isoxazol-5-yl]-3-oxo-propionic acid ethyl ester (1.4 g, 3.9 mmol) in 4M HCl in dioxane (5 ml) was stirred at room temperature. After 3 h the mixture was concentrated under reduced pressure to give the title compound as a pale yellow solid. MS [M+1]$^+$269.0.

C. 3-[3-(1-tert-Butoxycarbonylamino-3-methyl-butyl)-isoxazol-5-yl]-3-oxo-propionic acid ethyl ester

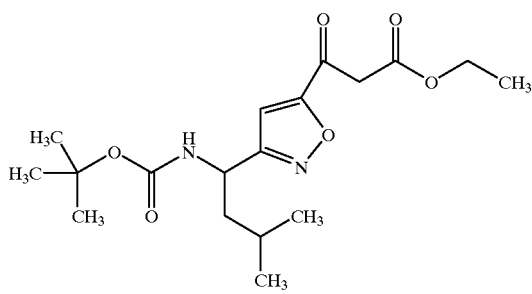

The title compound was prepared from 3-(1-tert-butoxycarbonylamino-3-methyl-butyl)-isoxazole-5-carboxylic acid by treatment with carbonyldiimidazole followed by the magnesium salt of mono-ethyl malonate as described in *Angew. Chem. Int Ed. Eng.*, 18 (1979), p. 72.

EXAMPLE 27

3-[2-(1-{2-[4-(3-o-Tolyl-ureido)-phenyl]-acetylamino}-butyl)-thiazol-5-yl]-propionic acid

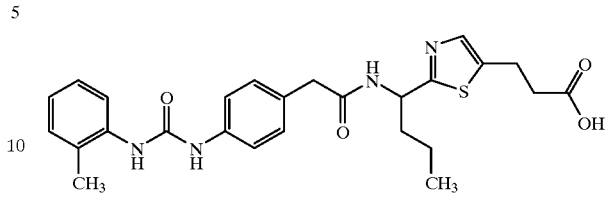

The title compound was prepared in an analogous fashion to Example 11 using the appropriate starting materials and reagents. White solid; MS [M−1]$^{+}$493.

EXAMPLE 28

N-{1-[5-(3-Methanesulfonylamino-3oxo-propyl)-thiazol-2-yl]-3-methyl-butyl}-2-[4-(3-o-tolyl-ureido)-phenyl]-acetamide

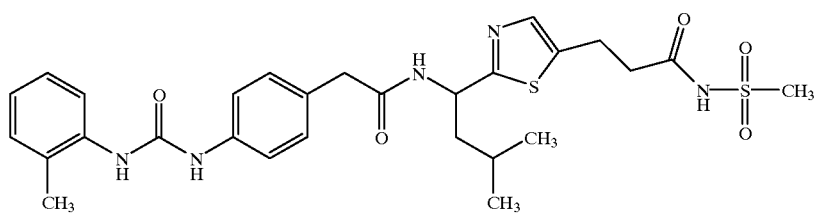

A mixture of 3-[2-(3-methyl-1-{2-[4-(3-o-tolyl-ureido)-phenyl]-acetylamino}-butyl)-thiazol-5-yl]-propionic acid (Example 13) (91 mg, 0.2 mmol), DMF (5 ml), EDCI (48 mg, 0.2 mmol) and DMAP (26 mg, 0.2 mmol) was stirred at room temperature. After 10 min. methane sulfonamide (51 mg, 0.5 mmol) was added. After stirring 16 h the solution was diluted with EtOAc and washed with 1N HCl (2×). The organic layer was dried over Na$_2$SO$_4$; filtered; and concentrated under reduced pressure. The resulting solid was purified by Flash 12 chromatography eluting with 10% AcOH in EtOAc to give 30 mg of the title compound as a white amorphous solid. MS [M−1]$^{+}$584.

EXAMPLE 29

2-{4-[3-(2-Chloro-phenyl)-ureido]-phenyl}-N-{1-[5-(3-methanesulfonylamino-3-oxo-propyl)-thiazol-2-yl]-3-methyl-butyl}-acetamide

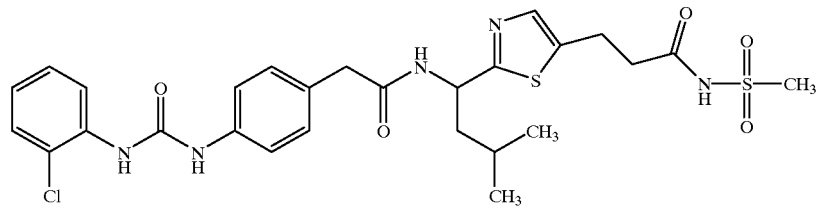

The title compound was prepared in the analogous fashion to Example 28 from 3-{2-[1-(2-{4-[3-(2-chloro-phenyl)-ureido]-phenyl}-acetylamino)-3-methyl-butyl]-thiazol-5-yl}-propionic acid. Colorless oil; MS [M+1]⁺607.

EXAMPLE 30

3-[2-({2-[4-(3-o-Tolyl-ureido)-phenyl]-acetylamino}-methyl)-thiazol-5-yl]-propionic acid

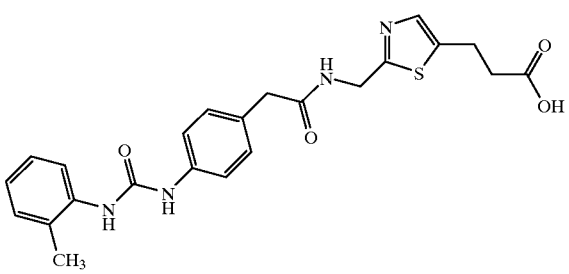

The title compound was prepared in an analogous fashion to Example 11 using the appropriate starting materials and reagents. White solid; MS [M+1]⁺453.

EXAMPLE 31

3-{2-[(2-{4-[3-(2-Chloro-phenyl)-ureido]-phenyl}-acetylamino)-methyl]-thiazol-5-yl}-propionic acid

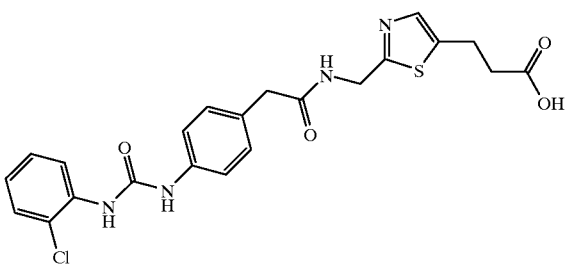

The title compound was prepared in an analogous fashion to Example 11 using the appropriate starting materials and reagents. White solid; MS [M+1]⁺473.

EXAMPLE 32

A. 3-[2-(1-{[4-(3-o-Tolyl-ureido)-phenyl]-acetyl}-pyrrolidin-2-yl)-thiazol-5-yl]-propionic acid

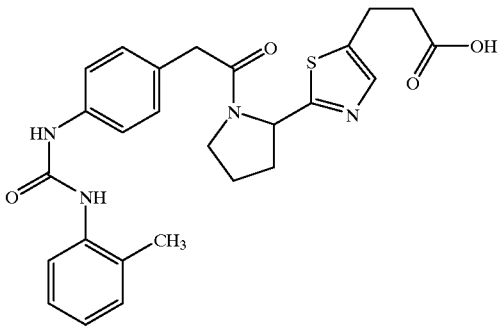

A solution was prepared of 3-[2-(1-{[4-(3-o-Tolyl-ureido)-phenyl]-acetyl}-pyrrolidin-2-yl)-thiazol-5-yl]-propionic acid methyl ester (0.33 g, 0.65 mmol) in methanol (4 mL), tetrahydrofuran (8 mL) and aqueous lithium hydroxide (2M, 4 mL). The solution was stirred for 4 h and partitioned between aqueous hydrochloric acid (1N, 30 mL) and ethyl acetate (100 mL). The aqueous portion was extracted with ethyl acetate (50 mL). The combined organic portions were extracted with brine (20 mL) and the solvent removed in vacuo to give the title compound (0.3 g, 94%). $^1$HNMR (400 MHz, CD$_3$OD): δ7.60 (d, J=7.3 Hz, 1H), 7.46 (s, 0.3H), 7.39 (d, J=8.5 Hz, 2.7H), 7.29 (d, J=8.5 Hz, 0.6), 7.18 (m, 3H), 6.99 (m, 1.4H), 5.40 (d, J=7.0 Hz, 0.3H), 5.34 (d, J=6.0 Hz, 0.7H) 3.4–3.8 (m, 4H), 3.05 (m, 2H), 2.60 (m, 2H), 2.27 (s, 3H), 1.9–2.2 (m, 4H). MS: Calc'd for C$_{25}$H$_{26}$N$_4$O$_4$S: 492.18. Found: (M+1) 492.9.

B. 3-[2-{[4-(3-o-Tolyl-ureido)-phenyl]-acetyl}-pypyrrolidin-2-yl)-thiazol-5-yl]-propionic acid methyl ester

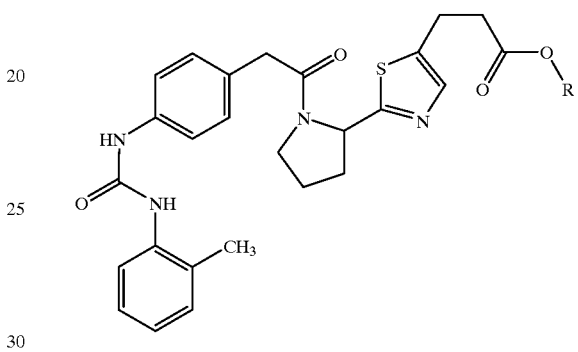

A solution of 3-(2-Pyrrolidin-2-yl-thiazol-5-yl)-propionic acid methyl ester (ca. 1.09 mmol) in dimethyl formamide was prepared. To this solution [4-(3-o-tolyl-ureido)-phenyl]-acetic acid (0.38 g, 1.3 mmol), 1-(3-dimethylaminopropyl)-3-ethylcarbodiimide hydrochloride (0.33 g, 1.7 mmol) and 1-hydroxybenzotriazole (0.24 g, 1.8 mmol) were added. The reaction was stirred 1 hour and triethylamine (0.15 g, 1.46 mmol) was added. After the reaction stirred overnight (ca. 16 h), it was poured into water (100 mL) and extracted with ethyl acetate (3×50 mL). The combined organic portion was extracted with saturated sodium bicarbonate (30 mL), water (2×15 mL) and brine (20 mL), then dried over magnesium sulfate. The solvent was removed in vacuo and the residue chromatographed on a silica gel column with methanol: acetic acid: ethyl acetate (1:1:98) to give the title compound (0.33 g, 65%). MS: Calc'd for C$_{26}$H$_{28}$N$_4$O$_4$S: 506.20. Found: (M+1) 507.2 and (M−1) 505.3.

C. 3-(2-Pyrrolidin-2-yl-thiazol-5-yl)-propionic acid methyl ester

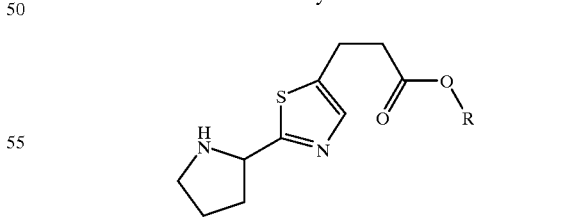

A solution of 2-[5-(2-Methoxycarbonyl-ethyl)-thiazol-2-yl]-pyrrolidine-1-carboxylic acid tert-butyl ester (0.37 g, 1.09 mmol) in a solution of hydrochloric acid in dioxane (4N, 10 mL) was stirred at room temperature for 1 h. The solvent was removed in vacuo and the residue dissolved in methylene chloride. The methylene chloride was removed in vacuo and the residue dissolved again in methylene chloride. The solvent was removed in vacuo and the residue used without purification. MS: Calc'd for $C_{11}H_{16}N_2O_2S$: 240.09. Found (M+1): 241.2.

D. 2-[5-(2-Methoxycarbonyl-ethyl)-thiazol-2-yl]-pyrrolidine-1-carboxylic acid tert-butyl ester

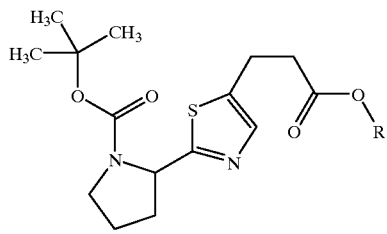

A solution of 2-(4-Methoxycarbonyl-2oxo-butylcarbamoyl)-pyrrolidine-1-carboxylic acid tert-butyl ester (0.57 g, 1.66 mmol) in toluene (15 mL) was prepared and Lawesson's reagent (0.405 g, 1.0 mmol) then added. The reaction was heated at reflux for 3 h and poured into water (150 mL). This mixture was extracted with ethyl acetate (3×50 mL). The combined organic portion was extracted with saturated sodium bicarbonate (2×30 mL) and brine (30 mL), then dried over magnesium sulfate. The solvent was removed in vacuo and the residue chromatographed on a Biotage 40s column with ethyl acetate: hexanes (1:1) to give the title compound (0.37 g, 65%). $^1$HNMR (400 MHz, CDCl$_3$): δ7.37 (s, 1H, thiazole), 5.18 (m, 0.4H), 5.05 (m, 0.6H), 3.67 (s, 3H), 3.35–3.60 (m, 2H), 3.10 (m, 2H), 2.64 (t, J=7.5 Hz, 2H), 2.20 (m, 2H), 1.90 (m, 2H), 1.62 (bs, 1H), 1.46 (bs, 4H), 1.31 (bs, 5H). MS: Calc'd for $C_{16}H_{24}N_2O_4S$: 340.15. Found (M+1): 341.0.

E. 2-(4-Methoxycarbonyl-2-oxo-butylcarbamoyl)-pyrrolidine-1-carboxylic acid tert-butyl ester

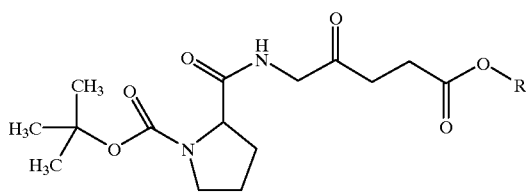

Pyrrolidine-1,2-dicarboxylic acid 2-tert-butyl ester 1-(2, 5-dioxo-pyrrolidin-1-yl) ester (1.03 g, 3.3 mmol) was dissolved in DMF (30 mL) and 5-amino-4-oxo-pentanoic acid methyl ester hydrochloride salt (0.60 g, 3.3 mmol) was added. The reaction mixture was stirred at room temperature for 1 h. Triethylamine was added and stirring continued overnight (ca. 16 h). The reaction was poured into water (300 mL) and extracted with ethyl acetate (3×70 mL). The combined organic portion was extracted with saturated aqueous sodium bicarbonate (60 mL), water (2×30 mL), and brine (50 mL). The organic portion was dried over magnesium sulfate and the solvent removed in vacuo. The resulting yellow oil was chromatographed on a Biotage 40S column with ethyl acetate: hexanes (4:1) to give the title compound (0.57 g, 50%). $^1$HNMR (400 MHz, CDCl$_3$): δ4.2 (m, 3H), 3.65 (s, 3H), 3.43 (m, 1.5H), 3.35 (m, 0.5H), 2.70 (m, 2H), 2.62 (m, 2H), 2.25 (bs, 0.25H), 2.15 (bs, 0.75H), 1.88 (m, 2H), 1.70 (bs, 1H), 1.25 (bs, 9H). MS: Calc'd for $C_{11}H_{18}N_2O_4$ (M-BOC): 242.13. Found (M-BOC+1): 243.0.

EXAMPLE 33

Binding of Biotinylated CS-1 to Isolated VLA-4

The VLA-4/bCS-1 receptor ligand binding assay described herein tests the ability of a compound to specifically inhibit VLA-4 dependent binding.

A. Preparation of VLA-4 Coated Plates

VLA-4 coated plates were prepared the day before the assay was carried out. The VLA-4-expressing stock was isolated from Jurkat cells according to the protocol of Makarem et al., *J. Biol. Chem.*, 269, 4005–4011 (1994) and was diluted in 50 mM NaHCO$_3$ (pH 8.8) to a final concentration of 0.4 mg/ml. Aliquots of 100 ml of this stock solution were then added to each well of a 96 well Microfluor "B" U-bottom plate (Dynatech No. 0010107205) and incubated overnight at 40° C. The coating solution was removed by aspiration and the wells were quenched for 0.5 hour with PBS plus 1 mM MnCl containing 1% non-fat dry milk (200 ml/well, 37° C.). The dry milk was removed by aspiration immediately before addition of the biotinylated CS-1.

B. Binding of Biotinylated CS-1 to Isolated VLA-4

The biotinylated CS-1 peptide (bCS-1) was prepared. This peptide was diluted with PBS plus 1 mM MnCl containing 0.1% non-fat dry milk (PBSB) to a final concentration of 5 mg/ml. Aliquots of 200 ml are added to the wells of a 96 well polypropylene transfer plate containing compounds (32, 10, 3.2, 1, 0.32 and 0.1 mM), vehicle or antibodies (0.5 mg/ml) in PBSB containing 0.1% DMSO for 60 min (37° C.). The plate is washed three times with 200 ml/well of PBSB to remove unbound bCS-1. Following this, 100 ml of a 1:5000 dilution of streptavidin poly-HRP in PBSB was added to each well for 60 min (37° C.). Unbound streptavidin poly-HRP was removed by aspiration and the plate was washed three times with PBSB (200 ml/well). Following the final wash, 100 ml of TMB substrate waas added to each well to react with the bound streptavidin poly-HRP and the OD of each well on the plate was determined on the Emax plate reader (650). The results were based on the mean of duplicate determinations.

EXAMPLE 34

VLA-4 Dependent THP1 Cell Binding to Baculovirus sVCAM

The THP1 baculovirus sVCAM cell binding assay tests the ability of a compound to inhibit VLA-4 dependent binding to sVCAM.

A Preparation of sVCAM Coated Plates

The baculovirus sVCAM coated plates were prepared the day before the experiment was carried out. The baculovirus sVCAM stock from PanVera was diluted in 50 mM NaHCO$_3$ (pH 8.8) to a final concentration of 5 mg/ml. Aliquots of 50 ml of this stock solution were then added to each well of a 96 well Microfluor "B" U bottom plate (Dynatech No. 0010107205) and incubated overnight (4° C.). The coating solution was removed by aspiration and the wells were quenched for 1 hour with PBS containing 5% non-fat dry milk (150 ml/well, 4° C.). The dry milk is removed by shock dumping immediately before addition of the biotinylated CS-1.

B. Labeling and Binding of THP1 Cells

THP1 cells were obtained from the American Type Culture Collection (ATCC, Rockville, Md.) and grown in RPMI 1640 media containing 10% 1 mM MnCl$_2$ for 20 min (37° C.). Following MnCl$_2$ activation, the cells were spun down (approximately 500 g for 5 min) and resuspended twice in serum free basal media (EBM, 37° C.). The cells in serum free media (2×10⁶/ml) were then incubated with 5 mM Calcein AM for 30 min at 37° C. Following labeling, all cells are spun down (approximately 500 g for 5 min) and resuspended twice in RPMI 1640 containing 10% FBS to cleave any free calcein AM. The cells were then resuspended twice in DPBS (+1 mM CaCl₂ and 1 mM MgCl₂) containing 1 mg/ml BSA (DPBSB) and diluted to 667,000 cells/ml. Aliquots Of 200 ml were added to the wells of a 96 well polypropylene transfer plate containing test compounds (10, 5, 1 and 0.1 mM), vehicle or antibodies (0.5 mg/ml) in DPBSB containing 0.1% DMSO for 30 min (37° C.). The next 150 ml (100,000 cells) were removed from each well and transferred into appropriate wells of a quenched baculovirus sVCAM coated plate for 45 min (37° C.). Unbound cells were removed by aspiration and the plate was washed three times with DPBSB (100 ml/well). Following the final wash, 100 ml of DPBSB was added to each well and the plate was read on a Cytoflour II fluorescent plate reader. Three readings were taken per well at an excitation of 480 and emission of 530. The results were based on the mean of duplicate determinations. The average background fluorescence of blank wells was subtracted from each sample to give a corrected fluorescence intensity value for each sample.

What is claimed is:

1. A compound of Formula (1.0.0):

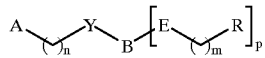

(1.0.0)

and pharmaceutically acceptable salts thereof, wherein:

A is phenyl, substituted with 0 to 3 $R^{10}$; or is a member selected from the group consisting of —$A^1$—NHC(=O)NH—$A^2$—, —$A^1$—NHC(=O)O—$A^2$—, and —$A^1$—NH(NCN)NH—$A^2$—, where $A^1$ and $A^2$ is each independently selected from the group consisting of hydrogen, provided that $A^1$ and $A^2$ may not both be hydrogen, pyridyl, and phenyl substituted with 0 to 3 $R^{10}$;

B is a group of partial Formula (1.1.2):

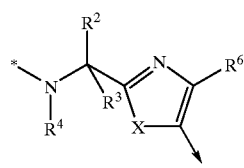

(1.1.2)

where the symbol "*" indicates the point of attachment of the moiety represented by partial Formula (1.1.2) to the moiety "Y" in Formula (1.0.0); and the symbol "→" indicates the point of attachment of the moiety represented by partial Formula (1.1.2) to the moiety "E" in Formula (1.0.0);

E is a single bond; —O—; —CH=CH—; or a moiety of Formula (1.9.0):

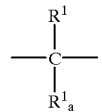

(1.9.0)

where $R^1_a$ is hydrogen when $R^1$ has the meaning of a mono-valent substituent; and $R^1_a$ is a single bond when $R^1$ has the meaning of a di-valent substituent;

X is —O—; —S(=O)$_q$—; or —N($R^{14}$)—;

Y is —C(=O)—; —C(=S)—; —S(=O)₂—; or —CH($R^a$)—;

m is an integer independently selected from 0, 1 and 2;

n is an integer independently selected from 1 and 2;

p is 1;

q is an integer independently selected from 0 and 2;

R is independently selected from the group consisting of -tetrazolyl; —C(=O)OR⁵; —C(=O)(CH₂)$_k$C(=O)OR⁵; —C(=O)NO•; —C(=O)NH—S(=O)₂R⁵; —S(=O)₂—NR¹⁴R⁵; —C(=O)NHS(=O)₂R⁶; and a moiety of partial Formulas (3.0.0):

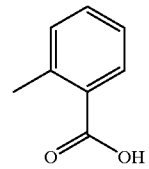

(3.0.0)

where:

k is an integer independently selected from 0, 1 and 2;

$R^1$ is independently selected from the group consisting of hydrogen; =O; =S; F; (C₁–C₆) alkyl substituted with 0 to 3 $R^{10}$; (C₂–C₆) alkenyl substituted with 0 to 3 $R^{10}$; phenyl substituted with 0 to 3 $R^{12}$; and phenyl(C₁–C₄) alkyl wherein said phenyl and alkyl are substituted with 0 to 3 $R^{12}$; C(=O)NR⁸R⁹; and C(=O)R⁸;

$R^2$ and $R^3$ are each independently selected from the group consisting of hydrogen; (C₁–C₄) alkyl substituted with 0 to 3 $R^{13}$; (C₂–C₆) alkenyl substituted with 0 to 3 $R^{13}$; (C₁–C₄) alkoxycarbonylamino-(C₁–C₄)alkyl-; (C₁–C₄) alkylthio-(C₁–C₄)alkyl-; (C₁–C₄) alkylsulfonyl-(C₁–C₄)alkyl-; hydroxy(C₁–C₄) alkylthio-(C₁–C₄) alkyl-; (C₁–C₄) alkylcarbonylamino-(C₁–C₄)alkyl-; (C₁–C₄) alkylsulfonylamino-(C₁–C₄) alkyl-; and (C₁–C₄) alkylsulfonylaminocarbonyl-(C₁–C₄) alkyl-; provided that $R^2$ and $R^3$ are each defined as above; or they are taken together as defined below; or one of them is taken together with $R^4$ as defined below, in which case the other has the meaning of hydrogen or methyl;

$R^2$ and $R^3$ are taken together to form a spirocyclic (C₃–C₁₄) carbocyclic ring substituted with 0 to 3 $R^{13}$; or $R^2$ or $R^3$ is taken together with $R^4$ and the carbon and nitrogen atoms to which they are respectively attached to form a pyrrolidinyl group substituted with 0 to 3 $R^{12}$;

$R^5$ is hydrogen; (C₁–C₄) alkyl; (C₃–C₆) cycloalkyl; or aryl;

$R^6$ is hydrogen; (C₁–C₄) alkyl; (CH₂)$_r$—(C₃–C₆) cycloalkyl; or (CH₂)$_s$-aryl; where:

r and s are each independently an integer selected from 0, 1, and 2;

$R^8$ and $R^9$ are each independently selected from the group consisting of hydrogen; $(C_1-C_4)$ alkyl substituted with 0 to 3 $R^{10}$; phenyl substituted with 0 to 3 $R^{12}$; and phenyl-$(C_1-C_4)$ alkyl wherein said phenyl and alkyl are substituted with 0 to 3 $R^{12}$;

$R^{10}$ is independently selected from the group consisting of F; Cl; —C(=O)$OR^{14}$; —OH; nitro; cyano; amino; di$(C_1-C_4)$ alkylamino; $(C_1-C_4)$ alkyl; $(C_1-C_4)$ alkoxy; $(C_1-C_4)$ alkylthio; and $(C_1-C_4)$ alkyl and $(C_1-C_4)$ alkoxy each substituted with 1 to 3 substituents independently selected from F and Cl;

$R^{12}$ when a substituent on a carbon atom, is independently selected from the group consisting of F; Cl; $(C_1-C_4)$ alkyl; $(C_3-C_6)$ cycloalkyl; $(C_1-C_4)$ alkoxy; —C(=O)$OR^{14}$; —OH; and $(C_1-C_4)$ alkyl and $(C_1-C_4)$ alkoxy each substituted with 1 to 3 substituents independently selected from F and Cl; or $R^{12}$ when $R^{12}$ is attached to a saturated carbon atom, may be =O or =S; or when $R^{12}$ is attached to a sulfur atom, may be =O; or $R^{12}$ when a substituent on a nitrogen atom, is independently selected from the group consisting of hydroxy; hydroxy$(C_1-C_4)$ alkyl; $(C_1-C_4)$ alkoxy; $(C_3-C_6)$ cycloalkyl; $(C_1-C_4)$ alkylcarbonyl; and phenyl;

$R^{13}$ is $(C_1-C_4)$ alkoxy; and $R^{14}$ is hydrogen; hydroxy; $(C_1-C_4)$ alkyl; $(C_3-C_6)$ cycloalkyl; or phenyl.

2. A compound according to claim 1 wherein A is selected from the group consisting of —$A^1$—NHC(=O)NH—$A^2$—, —$A^1$—NHC(=O)O—$A^2$—, and —$A^1$—NH(NCN)NH—$A^2$—, where $A_1$ and $A^2$ is each independently selected from the group consisting of hydrogen, provided that $A^1$ and $A^2$ may not both be hydrogen, and phenyl substituted with 0 or 1 substituent $R^{10}$.

3. A compound according to claim 2 wherein $R^{10}$ is a member selected from the group consisting of F, Cl, $F_3C$—, methyl, methoxy, hydroxyl, and iso-propyl.

4. A compound according to claim 3 wherein n is the integer 1 resulting in a methylene bridge.

5. A compound according to claim 4 wherein said component A and said methylene bridge attached thereto comprise a member selected from the group consisting of 4-hydroxyphenyl-; 3-methoxy-4-(N'-phenylurea)-phenylmethyl-; 4-(N'-phenylurea)-phenylmethyl-; 4-(N'-(2-methylphenyl)urea)-phenylmethyl-; 4-(N'-(2-methoxyphenyl)urea)-phenylmethyl-; 3-methoxy-4-(N'-(2-methylphenyl)urea)-phenylmethyl-; 4-(N'-(2-pyridyl)urea)-phenylmethyl-; 4-(N'-(2-fluorophenyl)urea)-phenylmethyl-; 4-(N'-(2-chlorophenyl)urea)-phenylmethyl-; 4-(N'-(2-chlorophenyl)urea)-3-methoxyphenylmethyl-; 4-(N'-(4-isopropylphenyl)urea)-phenylmethyl-; 6-methoxy-5-(N'-(o-toluyl)urea-2-pyridylmethyl-; and 4-(N'-(2-cyclopentyl)urea)-phenylmethyl-.

6. A compound according to claim 3 wherein Y is —C(=O)—.

7. A compound according to claim 6 wherein one of $R^2$ and $R^3$ is hydrogen and the other is selected from the group consisting essentially of iso-propyl, sec-butyl, iso-butyl, and tert-butyl; E- and Z-iso-butenyl, and E- and Z-pentenyl; 2-(methylthio)ethyl; 3-(hydroxypropylthio)methyl; 2-(methylsulfonyl)ethyl; 4-(acetylamino)butyl; 4-(methylsulfonylamino)butyl; and 4-ethoxycarbonylamino)butyl.

8. A compound according to claim 6 wherein p is 1; m is 1 or 2; and E is a bridging moiety of partial Formula (1.9.0):

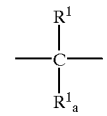

where $R^1_a$ is hydrogen when $R^1$ has the meaning of a mono-valent substituent; and $R^1_a$ is a single bond when $R^1$ has the meaning of a di-valent substituent; and wherein $R^1$ is a member selected from the group consisting essentially of methyl; ethyl; iso-propyl; tert-butyl; 2-propenyl; 1-, 2-, or 3-butenyl; phenyl; phenylmethyl; and phenylethyl.

9. A compound according to claim 8 wherein $R^1$ is independently substituted by 1 or 2 substituents $R^{12}$.

10. A pharmaceutical composition comprising a compound of Formula (1.0.0) as defined in claim 1 together with a pharmaceutically acceptable carrier for said compound, wherein the amount of said compound present is effective for treating asthma.

11. A pharmaceutical composition according to claim 10 additionally comprising one or more therapeutic agents.

12. A pharmaceutical composition according to claim 11 wherein said one or more therapeutic agent or agents is or are selected from the group consisting essentially of anti-inflammatory corticosteroids; nonsteroidal anti-inflammatory agents; bronchodilators; anti-asthmatic agents; immunosuppressant agents; immunostimulants; antimetabolites; antipsoriatics; and antidiabetics.

13. A pharmaceutical composition according to claim 12 wherein said therapeutic agent is a member selected from the group consisting essentially of theophylline, sulfasalazine, aminosalicylates; cyclosporin, FK-506, rapamycin, clophosphamide, methotrexate, and the interferons.

14. A method of treating asthma, comprising administering to a mammal in need of such treatment a therapeutically effective amount of a compound of Formula (1.0.0) as defined in claim 1 or a pharmaceutical composition as defined in claim 10.

* * * * *